(12) United States Patent
Edwardson et al.

(10) Patent No.: US 12,410,213 B2
(45) Date of Patent: Sep. 9, 2025

(54) POLYPEPTIDES SELF-ASSEMBLING INTO NANOPARTICLES

(71) Applicant: ETH ZÜRICH, Zürich (CH)

(72) Inventors: Thomas George Watt Edwardson, Zürich (CH); Donald Hilvert, Zürich (CH)

(73) Assignee: ETH ZÉRICH, Zürich (CH)

( * ) Notice: Subject to any disclaimer, the term of this patent is extended or adjusted under 35 U.S.C. 154(b) by 1101 days.

(21) Appl. No.: 17/265,765

(22) PCT Filed: Aug. 6, 2019

(86) PCT No.: PCT/EP2019/071143
§ 371 (c)(1),
(2) Date: Feb. 3, 2021

(87) PCT Pub. No.: WO2020/030654
PCT Pub. Date: Feb. 13, 2020

(65) Prior Publication Data
US 2021/0163540 A1    Jun. 3, 2021

(30) Foreign Application Priority Data
Aug. 7, 2018 (EP) ..................................... 18187862

(51) Int. Cl.
*A61K 38/00* (2006.01)
*C07K 14/00* (2006.01)
*C12N 15/113* (2010.01)
*C12N 15/88* (2006.01)

(52) U.S. Cl.
CPC .......... *C07K 14/001* (2013.01); *C12N 15/113* (2013.01); *C12N 15/88* (2013.01); *C07K 2319/21* (2013.01); *C12N 2310/14* (2013.01); *C12N 2310/3513* (2013.01)

(58) Field of Classification Search
CPC ...... B82Y 5/00; C07K 14/001; C07K 14/255; C07K 2319/21; C12N 15/113; C12N 15/88; C12N 2310/14; C12N 2310/3513
See application file for complete search history.

(56) References Cited

U.S. PATENT DOCUMENTS

| | | | | |
|---|---|---|---|---|
| 2013/0274441 A1* | 10/2013 | Baker | ..................... | G16B 15/00 703/11 |
| 2016/0122392 A1 | 5/2016 | Baker et al. | | |
| 2018/0318218 A1 | 11/2018 | Kamrud et al. | | |
| 2023/0080270 A1* | 3/2023 | Hilvert | ................... | A61K 47/42 424/450 |

FOREIGN PATENT DOCUMENTS

| | | | |
|---|---|---|---|
| CN | 103694317 A | 4/2014 | |
| WO | 2010/035009 A1 | 4/2010 | |
| WO | WO-2015054639 A1 * | 4/2015 | ............. A61K 39/12 |
| WO | 2016/138525 A1 | 9/2016 | |

OTHER PUBLICATIONS

Lilavivat, S., Sardar, D., Jana, S., Thomas, G. C., & Woycechowsky, K. J. In vivo encapsulation of nucleic acids using an engineered nonviral protein capsid. Journal of the American Chemical Society, 134(32), 13152-13155. (Year: 2012).*
Azuma, Y., Edwardson, T. G., & Hilvert, D. Tailoring lumazine synthase assemblies for bionanotechnology. Chemical Society Reviews, 47(10), 3543-3557. (Year: 2018).*
Azuma et al., "Tailoring Lumazine Synthase Assemblies for Bionanotechnology," Chemical Society Reviews 47 (10):3543-3557 (2018).
Cai et al., "Polypeptide Self-Assemblies: Nanostructures and Bioapplications," Chemical Society Reviews 45 (21): 5985-6012 (2016).
Edwardson et al., "Rational Engineering of a Designed Protein Cage for siRNA Delivery," Journal of the American Chemical Society 140(33):10439-10442 (2018).
King et al., "Computational Design of Self-Assembling Protein Nanomaterials with Atomic Level Accuracy," Science 336(6085):1171-1174 (2012).
Lilavivat et al., "In Vivo Encapsulation of Nucleic Acids Using an Engineered Nonviral Protein Capsid," Journal of the American Chemical Society 134(32):13152-13155 (2012).
International Search Report issued in Int'l Appl. No. PCT/EP2019/071143, mailed Sep. 23, 2019.
Heinze et al., "Protein Nanocontainers from Nonviral Origin: Testing the Mechanics of Artificial and Natural Protein Cages by AFM", The Journal of Physical Chemistry B 120(26):5945-5952 (2016).
Bayburt et al., "Self-Assembly of Discoidal Phospholipid Bilayer Nanoparticles with Membrane Scaffold Proteins," Nano Letters 2(8):853-85 (2002).

(Continued)

*Primary Examiner* — Lianko G Garyu
*Assistant Examiner* — Mercy H Sabila
(74) *Attorney, Agent, or Firm* — MEDLER FERRO WOODHOUSE & MILLS PLLC

(57) ABSTRACT

The present invention relates to polypeptides self-assembling into nanoparticles. In particular, the invention relates to a polypeptide comprising an amino acid sequence I (SEQ ID NO: 1), a nucleic acid sequence encoding said polypeptide, a nanoparticle comprising at least one polypeptide of the invention, a complex comprising said nanoparticle and one or more cargo molecules, and a method for transfecting a cell with said complex.

20 Claims, 30 Drawing Sheets
Specification includes a Sequence Listing.

(56) References Cited

OTHER PUBLICATIONS

Chang et al., "Curvature Dependence of Viral Protein Structures on Encapsidated Nanoemulsion Droplets," ACS Nano 2:281-286 (2008).
Chidchob, et al., "Synergy of Two Assembly Languages in DNA Nanostructures: Self-Assembly of Sequence-Defined Polymers on DNA Cages," J. Am. Chem. Soc. 138:4416-4425 (2016).
Edwardson et al., "Site-specific positioning of dendritic alkyl chains on DNA cages enables their geometry-dependent self-assembly," Nature Chemistry 5:868 (2013).
Kwak et al., "Virus-like Particles Templated by DNA Micelles: A General Method for Loading Virus Nanocarriers," J. Am. Chem. Soc. 132:7834-7835 (2010).
Loredo-Tovias et al., "Encapsidated ultrasmall nanolipospheres as novel nanocarriers for highly hydrophobic anticancer drugs," Nanoscale 9:11625-11631 (2017).
Olzmann and Carvalho, "Dynamics and functions of lipid droplets," Nat. Rev. Mol. Cell Biol. 20:137-155 (2019).
Ordovas, J. M. in Encyclopedia of Food Sciences and Nutrition (Second Edition) (ed Benjamin Caballero) 3543-3552 Academic Press (2003).
Spicer et al., "Peptide and protein nanoparticle conjugates: versatile platforms for biomedical applications," Chem. Soc. Rev. 47:3574-3620 (2018).

\* cited by examiner a b

Interior ↕ Exterior c d 50 nm a OP : Atto488-ssDNA
12.5 : 1 b  OP : Atto488-ssDNA
1.25 : 1

C

OP : Atto488-ssDNA
1 : 2

SEQUENCE LISTING

```
<160> NUMBER OF SEQ ID NOS: 38

<210> SEQ ID NO 1
<211> LENGTH: 186
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (11)..(11)
<223> OTHER INFORMATION: At least 3 of the X amino acids at positions
      11, 39, 66, 103,, 130, and 163  are independently of each other a
      positively charged amino acid.
<220> FEATURE:
<221> NAME/KEY: MISC_FEATURE
<222> LOCATION: (28)..(28)
<223> OTHER INFORMATION: Any amino acid
<220> FEATURE:
<221> NAME/KEY: MISC_FEATURE
<222> LOCATION: (30)..(30)
<223> OTHER INFORMATION: Any amino acid
<220> FEATURE:
<221> NAME/KEY: MISC_FEATURE
<222> LOCATION: (39)..(39)
<223> OTHER INFORMATION: At least 3 of the X amino acids at positions
      11, 39, 66, 103,, 130, and 163  are independently of each other a
      positively charged amino acid.
<220> FEATURE:
<221> NAME/KEY: MISC_FEATURE
<222> LOCATION: (51)..(51)
<223> OTHER INFORMATION: Any amino acid
<220> FEATURE:
<221> NAME/KEY: MISC_FEATURE
<222> LOCATION: (54)..(54)
<223> OTHER INFORMATION: Any amino acid
<220> FEATURE:
<221> NAME/KEY: MISC_FEATURE
<222> LOCATION: (55)..(55)
<223> OTHER INFORMATION: Any amino acid
<220> FEATURE:
<221> NAME/KEY: MISC_FEATURE
<222> LOCATION: (58)..(58)
<223> OTHER INFORMATION: Any amino acid
<220> FEATURE:
<221> NAME/KEY: MISC_FEATURE
<222> LOCATION: (62)..(62)
<223> OTHER INFORMATION: Any amino acid
<220> FEATURE:
<221> NAME/KEY: MISC_FEATURE
<222> LOCATION: (66)..(66)
```

```
<223> OTHER INFORMATION: At least 3 of the X amino acids at positions
      11, 39, 66, 103,, 130, and 163  are independently of each other a
      positively charged amino acid.
<220> FEATURE:
<221> NAME/KEY: MISC_FEATURE
<222> LOCATION: (76)..(76)
<223> OTHER INFORMATION: Any amino acid
<220> FEATURE:
<221> NAME/KEY: MISC_FEATURE
<222> LOCATION: (86)..(86)
<223> OTHER INFORMATION: Any amino acid
<220> FEATURE:
<221> NAME/KEY: MISC_FEATURE
<222> LOCATION: (88)..(88)
<223> OTHER INFORMATION: Any amino acid
<220> FEATURE:
<221> NAME/KEY: MISC_FEATURE
<222> LOCATION: (90)..(90)
<223> OTHER INFORMATION: Any amino acid
<220> FEATURE:
<221> NAME/KEY: MISC_FEATURE
<222> LOCATION: (92)..(92)
<223> OTHER INFORMATION: Any amino acid
<220> FEATURE:
<221> NAME/KEY: MISC_FEATURE
<222> LOCATION: (93)..(93)
<223> OTHER INFORMATION: Any amino acid
<220> FEATURE:
<221> NAME/KEY: MISC_FEATURE
<222> LOCATION: (94)..(94)
<223> OTHER INFORMATION: Any amino acid
<220> FEATURE:
<221> NAME/KEY: MISC_FEATURE
<222> LOCATION: (103)..(103)
<223> OTHER INFORMATION: At least 3 of the X amino acids at positions
      11, 39, 66, 103,, 130, and 163  are independently of each other a
      positively charged amino acid.
<220> FEATURE:
<221> NAME/KEY: MISC_FEATURE
<222> LOCATION: (114)..(114)
<223> OTHER INFORMATION: Any amino acid
<220> FEATURE:
<221> NAME/KEY: MISC_FEATURE
<222> LOCATION: (117)..(117)
<223> OTHER INFORMATION: Any amino acid
<220> FEATURE:
<221> NAME/KEY: MISC_FEATURE
<222> LOCATION: (120)..(120)
<223> OTHER INFORMATION: Any amino acid
<220> FEATURE:
<221> NAME/KEY: MISC_FEATURE
<222> LOCATION: (130)..(130)
<223> OTHER INFORMATION: At least 3 of the X amino acids at positions
      11, 39, 66, 103,, 130, and 163  are independently of each other a
      positively charged amino acid.
<220> FEATURE:
<221> NAME/KEY: MISC_FEATURE
<222> LOCATION: (163)..(163)
<223> OTHER INFORMATION: At least 3 of the X amino acids at positions
      11, 39, 66, 103,, 130, and 163  are independently of each other a
      positively charged amino acid.
<220> FEATURE:
<221> NAME/KEY: MISC_FEATURE
<222> LOCATION: (172)..(172)
<223> OTHER INFORMATION: Any amino acid
<220> FEATURE:
<221> NAME/KEY: MISC_FEATURE
<222> LOCATION: (175)..(175)
<223> OTHER INFORMATION: Any amino acid
<220> FEATURE:
<221> NAME/KEY: MISC_FEATURE
<222> LOCATION: (179)..(179)
<223> OTHER INFORMATION: Any amino acid
<220> FEATURE:
<221> NAME/KEY: MISC_FEATURE
<222> LOCATION: (183)..(183)
<223> OTHER INFORMATION: Any amino acid
<220> FEATURE:
<221> NAME/KEY: MISC_FEATURE
```

<222> LOCATION: (185)..(185)
<223> OTHER INFORMATION: Any amino acid

<400> SEQUENCE: 1

Met Xaa Gln Ala Ile Gly Ile Leu Glu Leu Xaa Ser Ile Ala Ala Gly
1               5                   10                  15

Met Glu Leu Gly Asp Ala Met Leu Lys Ser Ala Xaa Val Xaa Leu Leu
            20                  25                  30

Val Ser Lys Thr Ile Ser Xaa Gly Lys Phe Leu Leu Met Leu Gly Gly
        35                  40                  45

Asp Ile Xaa Ala Ile Xaa Xaa Ala Ile Xaa Thr Gly Thr Xaa Gln Ala
    50                  55                  60

Gly Xaa Leu Leu Val Asp Ser Leu Val Leu Ala Xaa Ile His Pro Ser
65              70                  75                  80

Val Leu Pro Ala Ile Xaa Gly Xaa Asn Xaa Val Xaa Xaa Xaa Gln Ala
                85                  90                  95

Val Gly Ile Val Glu Thr Xaa Ser Val Ala Ala Cys Ile Ser Ala Ala
            100                 105                 110

Asp Xaa Ala Val Xaa Gly Ser Xaa Val Thr Leu Val Arg Val His Met
    115                 120                 125

Ala Xaa Gly Ile Gly Gly Lys Cys Tyr Met Val Val Ala Gly Asp Val
130                 135                 140

Ser Asp Val Ala Leu Ala Val Thr Val Ala Ser Ser Ala Gly Ala
145                 150                 155                 160

Tyr Gly Xaa Leu Val Tyr Ala Ser Leu Ile Pro Xaa Pro His Xaa Ala
                165                 170                 175

Met Trp Xaa Gln Met Val Xaa Gly Xaa Glu
            180                 185

<210> SEQ ID NO 2
<211> LENGTH: 192
<212> TYPE: PRT
<213> ORGANISM: Artificial Sequence
<220> FEATURE:
<223> OTHER INFORMATION: Synthetic sequence

<400> SEQUENCE: 2

Met Ser Gln Ala Ile Gly Ile Leu Glu Leu Arg Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Arg Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Arg Leu Leu Val Asp Ser Leu Val Leu Ala Asn Ile His Pro Ser
65              70                  75                  80

Val Leu Pro Ala Ile Ser Gly Leu Asn Ser Val Asp Lys Arg Gln Ala
                85                  90                  95

Val Gly Ile Val Glu Thr Arg Ser Val Ala Ala Cys Ile Ser Ala Ala
            100                 105                 110

Asp Arg Ala Val Lys Gly Ser Asn Val Thr Leu Val Arg Val His Met
    115                 120                 125

Ala Arg Gly Ile Gly Gly Lys Cys Tyr Met Val Val Ala Gly Asp Val
130                 135                 140

Ser Asp Val Ala Leu Ala Val Thr Val Ala Ser Ser Ala Gly Ala
145                 150                 155

```
                145                 150                 155                 160
Tyr Gly Arg Leu Val Tyr Ala Ser Leu Ile Pro Arg Pro His Glu Ala
                    165                 170                 175

Met Trp Arg Gln Met Val Glu Gly Leu Glu His His His His His His
                    180                 185                 190
```

<210> SEQ ID NO 3
<211> LENGTH: 188
<212> TYPE: PRT
<213> ORGANISM: Artificial Sequence
<220> FEATURE:
<223> OTHER INFORMATION: Synthetic sequence

<400> SEQUENCE: 3

```
Met Ser Gln Ala Ile Gly Ile Leu Glu Leu Arg Ser Ile Ala Ala Gly
1               5                   10                  15

Met Glu Leu Gly Asp Ala Met Leu Lys Ser Ala Asn Val Asp Leu Leu
                20                  25                  30

Val Ser Lys Thr Ile Ser Arg Gly Lys Phe Leu Leu Met Leu Gly Gly
                35                  40                  45

Asp Ile Gly Ala Ile Gln Gln Ala Ile Glu Thr Gly Thr Ser Gln Ala
        50                  55                  60

Gly Arg Leu Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Arg Ser Val Ala Ala Cys Ile Ser Ala Ala
                100                 105                 110

Asp Arg Ala Val Lys Gly Ser Asn Val Thr Leu Val Arg Val His Met
                115                 120                 125

Ala Arg Gly Ile Gly Gly Lys Cys Tyr Met Val Val Ala Gly Asp Val
        130                 135                 140

Ser Asp Val Ala Leu Ala Val Thr Val Ala Ser Ser Ser Ala Gly Ala
145                 150                 155                 160

Tyr Gly Arg Leu Val Tyr Ala Ser Leu Ile Pro Arg Pro His Glu Ala
                    165                 170                 175

Met Trp Arg Gln Met Val Glu Gly Leu Glu Gly Ser
                    180                 185
```

<210> SEQ ID NO 4
<211> LENGTH: 192
<212> TYPE: PRT
<213> ORGANISM: Artificial Sequence
<220> FEATURE:
<223> OTHER INFORMATION: Synthetic sequence

<400> SEQUENCE: 4

```
Met Ser Gln Ala Ile Gly Ile Leu Glu Leu Arg Ser Ile Ala Ala Gly
1               5                   10                  15

Met Glu Leu Gly Asp Ala Met Leu Lys Ser Ala Asn Val Asp Leu Leu
                20                  25                  30

Val Ser Lys Thr Ile Ser Arg Gly Lys Phe Leu Leu Met Leu Gly Gly
                35                  40                  45

Asp Ile Gly Ala Ile Gln Gln Ala Ile Glu Thr Gly Thr Ser Gln Ala
        50                  55                  60

Gly Arg Leu Leu Val Asp Ser Leu Val Leu Ala Asn Ile His Pro Ser
65                  70                  75                  80
```

Val Leu Pro Ala Ile Ser Gly Leu Asn Ser Val Asp Cys Arg Gln Ala
                85                  90                  95

Val Gly Ile Val Glu Thr Arg Ser Val Ala Ala Cys Ile Ser Ala Ala
            100                 105                 110

Asp Arg Ala Val Lys Gly Ser Asn Val Thr Leu Val Arg Val His Met
            115                 120                 125

Ala Arg Gly Ile Gly Gly Lys Cys Tyr Met Val Val Ala Gly Asp Val
            130                 135                 140

Ser Asp Val Ala Leu Ala Val Thr Val Ala Ser Ser Ser Ala Gly Ala
145                 150                 155                 160

Tyr Gly Arg Leu Val Tyr Ala Ser Leu Ile Pro Arg Pro His Glu Ala
                165                 170                 175

Met Trp Arg Gln Met Val Glu Gly Leu Glu His His His His His His
            180                 185                 190

<210> SEQ ID NO 5
<211> LENGTH: 230
<212> TYPE: PRT
<213> ORGANISM: Artificial Sequence
<220> FEATURE:
<223> OTHER INFORMATION: Synthetic sequence

<400> SEQUENCE: 5

Met Ser Gln Ala Ile Gly Ile Leu Glu Leu Arg Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Arg Gly Lys Phe Leu Leu Met Leu Gly Gly
            35                  40                  45

Asp Ile Gly Ala Ile Gln Gln Ala Ile Glu Thr Gly Thr Ser Gln Ala
        50                  55                  60

Gly Arg Leu Leu Val Asp Ser Leu Val Leu Ala Asn Ile His Pro Ser
65                  70                  75                  80

Val Leu Pro Ala Ile Ser Gly Leu Asn Ser Val Asp Cys Arg Gln Ala
                85                  90                  95

Val Gly Ile Val Glu Thr Arg Ser Val Ala Ala Cys Ile Ser Ala Ala
            100                 105                 110

Asp Arg Ala Val Lys Gly Ser Asn Val Thr Leu Val Arg Val His Met
            115                 120                 125

Ala Arg Gly Ile Gly Gly Lys Cys Tyr Met Val Val Ala Gly Asp Val
            130                 135                 140

Ser Asp Val Ala Leu Ala Val Thr Val Ala Ser Ser Ser Ala Gly Ala
145                 150                 155                 160

Tyr Gly Arg Leu Val Tyr Ala Ser Leu Ile Pro Arg Pro His Glu Ala
                165                 170                 175

Met Trp Arg Gln Met Val Glu Gly Leu Glu His His His His His His
            180                 185                 190

Glu Phe Pro Pro Glu Val Glu Glu Gln Asp Asp Gly Thr Leu Pro Met
            195                 200                 205

Ser Cys Ala Gln Glu Ser Gly Met Asp Arg His Pro Ala Ala Cys Ala
        210                 215                 220

Ser Ala Arg Ile Asn Val
225                 230

<210> SEQ ID NO 6
<211> LENGTH: 192

```
<212> TYPE: PRT
<213> ORGANISM: Artificial Sequence
<220> FEATURE:
<223> OTHER INFORMATION: Synthetic sequence

<400> SEQUENCE: 6

Met Ser Gln Ala Ile Gly Ile Leu Glu Leu Thr Ser Ile Ala Ala Gly
1               5                   10                  15

Met Glu Leu Gly Asp Ala Met Leu Lys Ser Ala Asn Val Asp Leu Leu
                20                  25                  30

Val Ser Lys Thr Ile Ser Arg Gly Lys Phe Leu Leu Met Leu Gly Gly
            35                  40                  45

Asp Ile Gly Ala Ile Gln Gln Ala Ile Glu Thr Gly Thr Ser Gln Ala
        50                  55                  60

Gly Glu Leu Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Trp Ser Val Ala Ala Cys Ile Ser Ala Ala
            100                 105                 110

Asp Arg Ala Val Lys Gly Ser Asn Val Thr Leu Val Arg Val His Met
        115                 120                 125

Ala Phe Gly Ile Gly Gly Lys Cys Tyr Met Val Val Ala Gly Asp Val
    130                 135                 140

Ser Asp Val Ala Leu Ala Val Thr Val Ala Ser Ser Ala Gly Ala
145                 150                 155                 160

Tyr Gly Leu Leu Val Tyr Ala Ser Leu Ile Pro Arg Pro His Glu Ala
                165                 170                 175

Met Trp Arg Gln Met Val Glu Gly Leu Glu His His His His His His
                180                 185                 190

<210> SEQ ID NO 7
<211> LENGTH: 192
<212> TYPE: PRT
<213> ORGANISM: Artificial Sequence
<220> FEATURE:
<223> OTHER INFORMATION: Synthetic sequence

<400> SEQUENCE: 7

Met Ser Gln Ala Ile Gly Ile Leu Glu Leu Thr Ser Ile Ala Ala Gly
1               5                   10                  15

Met Glu Leu Gly Asp Ala Met Leu Lys Ser Ala Asn Val Asp Leu Leu
                20                  25                  30

Val Ser Lys Thr Ile Ser Arg Gly Lys Phe Leu Leu Met Leu Gly Gly
            35                  40                  45

Asp Ile Gly Ala Ile Gln Gln Ala Ile Glu Thr Gly Thr Ser Gln Ala
        50                  55                  60

Gly Glu Leu Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Trp Ser Val Ala Ala Cys Ile Ser Ala Ala
            100                 105                 110

Asp Arg Ala Val Lys Gly Ser Asn Val Thr Leu Val Arg Val His Met
        115                 120                 125

Ala Arg Gly Ile Gly Gly Lys Cys Tyr Met Val Val Ala Gly Asp Val
    130                 135                 140
```

```
Ser Asp Val Ala Leu Ala Val Thr Val Ala Ser Ser Ser Ala Gly Ala
145                 150                 155                 160

Tyr Gly Leu Leu Val Tyr Ala Ser Leu Ile Pro Arg Pro His Glu Ala
                165                 170                 175

Met Trp Arg Gln Met Val Glu Gly Leu Glu His His His His His
            180                 185                 190
```

<210> SEQ ID NO 8
<211> LENGTH: 192
<212> TYPE: PRT
<213> ORGANISM: Artificial Sequence
<220> FEATURE:
<223> OTHER INFORMATION: Synthetic sequence

<400> SEQUENCE: 8

```
Met Ser Gln Ala Ile Gly Ile Leu Glu Leu Arg Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Pro Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Glu Leu Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Arg Ser Val Ala Ala Cys Ile Ser Ala Ala
            100                 105                 110

Asp Arg Ala Val Lys Gly Ser Asn Val Thr Leu Val Arg Val His Met
        115                 120                 125

Ala Phe Gly Ile Gly Gly Lys Cys Tyr Met Val Ala Gly Asp Val
    130                 135                 140

Ser Asp Val Ala Leu Ala Val Thr Val Ala Ser Ser Ser Ala Gly Ala
145                 150                 155                 160

Tyr Gly Leu Leu Val Tyr Ala Ser Leu Ile Pro Arg Pro His Glu Ala
                165                 170                 175

Met Trp Arg Gln Met Val Glu Gly Leu Glu His His His His His
            180                 185                 190
```

<210> SEQ ID NO 9
<211> LENGTH: 192
<212> TYPE: PRT
<213> ORGANISM: Artificial Sequence
<220> FEATURE:
<223> OTHER INFORMATION: Synthetic sequence

<400> SEQUENCE: 9

```
Met Ser Gln Ala Ile Gly Ile Leu Glu Leu Arg Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Arg Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Glu Leu Leu Val Asp Ser Leu Val Leu Ala Asn Ile His Pro Ser
```

```
                65                  70                  75                  80
Val Leu Pro Ala Ile Ser Gly Leu Asn Ser Val Asp Lys Arg Gln Ala
                85                  90                  95

Val Gly Ile Val Glu Thr Trp Ser Val Ala Ala Cys Ile Ser Ala Ala
                100                 105                 110

Asp Arg Ala Val Lys Gly Ser Asn Val Thr Leu Val Arg Val His Met
                115                 120                 125

Ala Phe Gly Ile Gly Lys Cys Tyr Met Val Ala Gly Asp Val
                130                 135                 140

Ser Asp Val Ala Leu Ala Val Thr Val Ala Ser Ser Ser Ala Gly Ala
145                 150                 155                 160

Tyr Gly Leu Leu Val Tyr Ala Ser Leu Ile Pro Arg Pro His Glu Ala
                165                 170                 175

Met Trp Arg Gln Met Val Glu Gly Leu Glu His His His His His His
                180                 185                 190
```

<210> SEQ ID NO 10
<211> LENGTH: 192
<212> TYPE: PRT
<213> ORGANISM: Artificial Sequence
<220> FEATURE:
<223> OTHER INFORMATION: Synthetic sequence

<400> SEQUENCE: 10

```
Met Ser Gln Ala Ile Gly Ile Leu Glu Leu Thr Ser Ile Ala Ala Gly
1               5                   10                  15

Met Glu Leu Gly Asp Ala Met Leu Lys Ser Ala Asn Val Asp Leu Leu
                20                  25                  30

Val Ser Lys Thr Ile Ser Pro Gly Lys Phe Leu Leu Met Leu Gly Gly
                35                  40                  45

Asp Ile Gly Ala Ile Gln Gln Ala Ile Glu Thr Gly Thr Ser Gln Ala
                50                  55                  60

Gly Glu Leu Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Arg Ser Val Ala Ala Cys Ile Ser Ala Ala
                100                 105                 110

Asp Arg Ala Val Lys Gly Ser Asn Val Thr Leu Val Arg Val His Met
                115                 120                 125

Ala Arg Gly Ile Gly Gly Lys Cys Tyr Met Val Ala Gly Asp Val
                130                 135                 140

Ser Asp Val Ala Leu Ala Val Thr Val Ala Ser Ser Ser Ala Gly Ala
145                 150                 155                 160

Tyr Gly Arg Leu Val Tyr Ala Ser Leu Ile Pro Arg Pro His Glu Ala
                165                 170                 175

Met Trp Arg Gln Met Val Glu Gly Leu Glu His His His His His His
                180                 185                 190
```

<210> SEQ ID NO 11
<211> LENGTH: 191
<212> TYPE: PRT
<213> ORGANISM: Artificial Sequence
<220> FEATURE:
<223> OTHER INFORMATION: Synthetic sequence

<400> SEQUENCE: 11

```
Met Ser Gln Ala Ile Gly Ile Leu Glu Leu Arg Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Arg Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Glu Leu Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Trp Ser Val Ala Ala Cys Ile Ser Ala Ala
            100                 105                 110

Asp Arg Ala Val Lys Gly Ser Asn Val Thr Leu Val Arg Val His Met
        115                 120                 125

Ala Arg Gly Ile Gly Gly Lys Cys Tyr Met Val Ala Gly Asp Val
    130                 135                 140

Ser Asp Val Ala Leu Ala Val Thr Val Ala Ser Ser Ser Ala Gly Ala
145                 150                 155                 160

Tyr Gly Leu Leu Val Tyr Ala Ser Leu Ile Pro Arg Pro His Glu Ala
                165                 170                 175

Met Trp Arg Gln Met Val Glu Gly Leu Glu His His His His
            180                 185                 190

<210> SEQ ID NO 12
<211> LENGTH: 192
<212> TYPE: PRT
<213> ORGANISM: Artificial Sequence
<220> FEATURE:
<223> OTHER INFORMATION: Synthetic sequence

<400> SEQUENCE: 12

Met Ser Gln Ala Ile Gly Ile Leu Glu Leu Arg Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Arg Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Glu Leu Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Arg Ser Val Ala Ala Cys Ile Ser Ala Ala
            100                 105                 110

Asp Arg Ala Val Lys Gly Ser Asn Val Thr Leu Val Arg Val His Met
        115                 120                 125

Ala Arg Gly Ile Gly Gly Lys Cys Tyr Met Val Ala Gly Asp Val
    130                 135                 140

Ser Asp Val Ala Leu Ala Val Thr Val Ala Ser Ser Ser Ala Gly Ala
145                 150                 155                 160

Tyr Gly Leu Leu Val Tyr Ala Ser Leu Ile Pro Arg Pro His Glu Ala
                165                 170                 175
```

Met Trp Arg Gln Met Val Glu Gly Leu Glu His His His His His
            180                 185                 190

<210> SEQ ID NO 13
<211> LENGTH: 192
<212> TYPE: PRT
<213> ORGANISM: Artificial Sequence
<220> FEATURE:
<223> OTHER INFORMATION: Synthetic sequence

<400> SEQUENCE: 13

Met Ser Gln Ala Ile Gly Ile Leu Glu Leu Arg Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Pro Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Arg Leu Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Arg Ser Val Ala Ala Cys Ile Ser Ala Ala
            100                 105                 110

Asp Arg Ala Val Lys Gly Ser Asn Val Thr Leu Val Arg Val His Met
        115                 120                 125

Ala Phe Gly Ile Gly Gly Lys Cys Tyr Met Val Val Ala Gly Asp Val
    130                 135                 140

Ser Asp Val Ala Leu Ala Val Thr Val Ala Ser Ser Ser Ala Gly Ala
145                 150                 155                 160

Tyr Gly Arg Leu Val Tyr Ala Ser Leu Ile Pro Arg Pro His Glu Ala
                165                 170                 175

Met Trp Arg Gln Met Val Glu Gly Leu Glu His His His His His
            180                 185                 190

<210> SEQ ID NO 14
<211> LENGTH: 192
<212> TYPE: PRT
<213> ORGANISM: Artificial Sequence
<220> FEATURE:
<223> OTHER INFORMATION: Synthetic sequence

<400> SEQUENCE: 14

Met Ser Gln Ala Ile Gly Ile Leu Glu Leu Arg Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Pro Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Arg Leu Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Arg Ser Val Ala Ala Cys Ile Ser Ala Ala
            100                 105                 110

```
Asp Arg Ala Val Lys Gly Ser Asn Val Thr Leu Val Arg Val His Met
        115                 120                 125

Ala Arg Gly Ile Gly Gly Lys Cys Tyr Met Val Val Ala Gly Asp Val
    130                 135                 140

Ser Asp Val Ala Leu Ala Val Thr Val Ala Ser Ser Ser Ala Gly Ala
145                 150                 155                 160

Tyr Gly Arg Leu Val Tyr Ala Ser Leu Ile Pro Arg Pro His Glu Ala
                165                 170                 175

Met Trp Arg Gln Met Val Glu Gly Leu Glu His His His His His His
            180                 185                 190
```

<210> SEQ ID NO 15
<211> LENGTH: 192
<212> TYPE: PRT
<213> ORGANISM: Artificial Sequence
<220> FEATURE:
<223> OTHER INFORMATION: Synthetic sequence

<400> SEQUENCE: 15

```
Met Ser Gln Ala Ile Gly Ile Leu Glu Leu Arg Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Arg Gly Lys Phe Leu Leu Met Leu Gly Gly
            35                  40                  45

Asp Ile Gly Ala Ile Gln Gln Ala Ile Glu Thr Gly Thr Ser Gln Ala
    50                  55                  60

Gly Arg Leu Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Trp Ser Val Ala Ala Cys Ile Ser Ala Ala
            100                 105                 110

Asp Arg Ala Val Lys Gly Ser Asn Val Thr Leu Val Arg Val His Met
        115                 120                 125

Ala Arg Gly Ile Gly Gly Lys Cys Tyr Met Val Val Ala Gly Asp Val
    130                 135                 140

Ser Asp Val Ala Leu Ala Val Thr Val Ala Ser Ser Ser Ala Gly Ala
145                 150                 155                 160

Tyr Gly Arg Leu Val Tyr Ala Ser Leu Ile Pro Arg Pro His Glu Ala
                165                 170                 175

Met Trp Arg Gln Met Val Glu Gly Leu Glu His His His His His His
            180                 185                 190
```

<210> SEQ ID NO 16
<211> LENGTH: 192
<212> TYPE: PRT
<213> ORGANISM: Artificial Sequence
<220> FEATURE:
<223> OTHER INFORMATION: Synthetic sequence

<400> SEQUENCE: 16

```
Met Ser Gln Ala Ile Gly Ile Leu Glu Leu Arg Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Arg Gly Lys Phe Leu Leu Met Leu Gly Gly
```

```
                35                  40                  45
Asp Ile Gly Ala Ile Gln Gln Ala Ile Glu Thr Gly Thr Ser Gln Ala
         50                  55                  60
Gly Arg Leu Leu Val Asp Ser Leu Val Leu Ala Asn Ile His Pro Ser
 65                  70                  75                  80
Val Leu Pro Ala Ile Ser Gly Leu Asn Ser Val Asp Lys Arg Gln Ala
                 85                  90                  95
Val Gly Ile Val Glu Thr Arg Ser Val Ala Ala Cys Ile Ser Ala Ala
            100                 105                 110
Asp Arg Ala Val Lys Gly Ser Asn Val Thr Leu Val Arg Val His Met
            115                 120                 125
Ala Arg Gly Ile Gly Gly Lys Cys Tyr Met Val Val Ala Gly Asp Val
        130                 135                 140
Ser Asp Val Ala Leu Ala Val Thr Val Ala Ser Ser Ser Ala Gly Ala
145                 150                 155                 160
Tyr Gly Leu Leu Val Tyr Ala Ser Leu Ile Pro Arg Pro His Glu Ala
                165                 170                 175
Met Trp Arg Gln Met Val Glu Gly Leu Glu His His His His His His
            180                 185                 190
```

<210> SEQ ID NO 17
<211> LENGTH: 38
<212> TYPE: PRT
<213> ORGANISM: Artificial Sequence
<220> FEATURE:
<223> OTHER INFORMATION: Synthetic sequence

<400> SEQUENCE: 17

```
Glu Phe Pro Pro Glu Val Glu Glu Gln Asp Asp Gly Thr Leu Pro Met
 1               5                  10                  15
Ser Cys Ala Gln Glu Ser Gly Met Asp Arg His Pro Ala Ala Cys Ala
                20                  25                  30
Ser Ala Arg Ile Asn Val
         35
```

<210> SEQ ID NO 18
<211> LENGTH: 21
<212> TYPE: DNA
<213> ORGANISM: Artificial Sequence
<220> FEATURE:
<223> OTHER INFORMATION: Synthetic sequence

<400> SEQUENCE: 18
ttaattaaag acttcaagcg g                                          21

<210> SEQ ID NO 19
<211> LENGTH: 21
<212> TYPE: DNA
<213> ORGANISM: Artificial Sequence
<220> FEATURE:
<223> OTHER INFORMATION: Synthetic sequence

<400> SEQUENCE: 19
gcttgaagtc tttaattaat t                                          21

<210> SEQ ID NO 20
<211> LENGTH: 21
<212> TYPE: DNA
<213> ORGANISM: Artificial Sequence
<220> FEATURE:
<223> OTHER INFORMATION: Synthetic sequence

```
<400> SEQUENCE: 20
gaacttcagg gtcagcttgg g                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic sequence

<400> SEQUENCE: 21
caagctgacc ctgaagttct t                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic sequence

<400> SEQUENCE: 22
gaacttcagg gtcagcttgg g                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic sequence

<400> SEQUENCE: 23
caagctgacc ctgaagttct t                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic sequence

<400> SEQUENCE: 24
uaaggcuaug aagagauact t                                              21

<210> SEQ ID NO 25
<211> LENGTH: 20
<212> TYPE: DNA
<213> ORGANISM: Artificial Sequence
<220> FEATURE:
<223> OTHER INFORMATION: Synthetic sequence

<400> SEQUENCE: 25
guaucuuuca uagccuuatt                                                20

<210> SEQ ID NO 26
<211> LENGTH: 18
<212> TYPE: DNA
<213> ORGANISM: Artificial Sequence
<220> FEATURE:
<223> OTHER INFORMATION: Synthetic sequence

<400> SEQUENCE: 26
tcgagggcag ctaatgag                                                  18

<210> SEQ ID NO 27
```

```
<211> LENGTH: 18
<212> TYPE: DNA
<213> ORGANISM: Artificial Sequence
<220> FEATURE:
<223> OTHER INFORMATION: Synthetic sequence

<400> SEQUENCE: 27
tgcactcatt agctgccc                                                 18

<210> SEQ ID NO 28
<211> LENGTH: 18
<212> TYPE: DNA
<213> ORGANISM: Artificial Sequence
<220> FEATURE:
<223> OTHER INFORMATION: Synthetic sequence

<400> SEQUENCE: 28
cgtggcgagc agcagcgc                                                 18

<210> SEQ ID NO 29
<211> LENGTH: 20
<212> TYPE: DNA
<213> ORGANISM: Artificial Sequence
<220> FEATURE:
<223> OTHER INFORMATION: Synthetic sequence

<400> SEQUENCE: 29
cctggtgcgt gtgcacatgg                                               20

<210> SEQ ID NO 30
<211> LENGTH: 22
<212> TYPE: DNA
<213> ORGANISM: Artificial Sequence
<220> FEATURE:
<223> OTHER INFORMATION: Synthetic sequence

<400> SEQUENCE: 30
gtgctcgaga ccttccacca tc                                            22

<210> SEQ ID NO 31
<211> LENGTH: 23
<212> TYPE: DNA
<213> ORGANISM: Artificial Sequence
<220> FEATURE:
<223> OTHER INFORMATION: Synthetic sequence

<400> SEQUENCE: 31
ggtgatgcga tgctgaaaag cgc                                           23

<210> SEQ ID NO 32
<211> LENGTH: 24
<212> TYPE: DNA
<213> ORGANISM: Artificial Sequence
<220> FEATURE:
<223> OTHER INFORMATION: Synthetic sequence

<400> SEQUENCE: 32
gcgattcagc aggcgattga aacc                                          24

<210> SEQ ID NO 33
<211> LENGTH: 24
<212> TYPE: DNA
<213> ORGANISM: Artificial Sequence
<220> FEATURE:
<223> OTHER INFORMATION: Synthetic sequence

<400> SEQUENCE: 33
```

```
cgattagcgg tctgaatagc gtgg                                           24
```

<210> SEQ ID NO 34
<211> LENGTH: 24
<212> TYPE: DNA
<213> ORGANISM: Artificial Sequence
<220> FEATURE:
<223> OTHER INFORMATION: Synthetic sequence

<400> SEQUENCE: 34

```
ggtttcaatc gcctgctgaa tcgc                                           24
```

<210> SEQ ID NO 35
<211> LENGTH: 24
<212> TYPE: DNA
<213> ORGANISM: Artificial Sequence
<220> FEATURE:
<223> OTHER INFORMATION: Synthetic sequence

<400> SEQUENCE: 35

```
ccacgctatt cagaccgcta atcg                                           24
```

<210> SEQ ID NO 36
<211> LENGTH: 26
<212> TYPE: DNA
<213> ORGANISM: Artificial Sequence
<220> FEATURE:
<223> OTHER INFORMATION: Synthetic sequence

<400> SEQUENCE: 36

```
gaaggagata tacatatgag ccaggc                                         26
```

<210> SEQ ID NO 37
<211> LENGTH: 189
<212> TYPE: PRT
<213> ORGANISM: Artificial Sequence
<220> FEATURE:
<223> OTHER INFORMATION: Synthetic sequence

<400> SEQUENCE: 37

```
Met Ser Gln Ala Ile Gly Ile Leu Glu Leu Arg Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Arg Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Arg Leu Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Arg Ser Val Ala Ala Cys Ile Ser Ala Ala
            100                 105                 110

Asp Arg Ala Val Lys Gly Ser Asn Val Thr Leu Val Arg Val His Met
        115                 120                 125

Ala Arg Gly Ile Gly Gly Lys Cys Tyr Met Val Val Ala Gly Asp Val
    130                 135                 140

Ser Asp Val Ala Leu Ala Val Thr Val Ala Ser Ser Ser Ala Gly Ala
145                 150                 155                 160
```

```
Tyr Gly Arg Leu Val Tyr Ala Ser Leu Ile Pro Arg Pro His Glu Ala
                165                 170                 175

Met Trp Arg Gln Met Val Glu Gly Leu Glu His His His
            180                 185

<210> SEQ ID NO 38
<211> LENGTH: 195
<212> TYPE: PRT
<213> ORGANISM: Artificial Sequence
<220> FEATURE:
<223> OTHER INFORMATION: Synthetic sequence

<400> SEQUENCE: 38

Met Ser Gln Ala Ile Gly Ile Leu Glu Leu Arg Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Arg Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Arg Leu Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Arg Ser Val Ala Ala Cys Ile Ser Ala Ala
            100                 105                 110

Asp Arg Ala Val Lys Gly Ser Asn Val Thr Leu Val Arg Val His Met
        115                 120                 125

Ala Arg Gly Ile Gly Gly Lys Cys Tyr Met Val Val Ala Gly Asp Val
    130                 135                 140

Ser Asp Val Ala Leu Ala Val Thr Val Ala Ser Ser Ser Ala Gly Ala
145                 150                 155                 160

Tyr Gly Arg Leu Val Tyr Ala Ser Leu Ile Pro Arg Pro His Glu Ala
                165                 170                 175

Met Trp Arg Gln Met Val Glu Gly Leu Glu His His His His His His
            180                 185                 190

His His His
        195
```

POLYPEPTIDES SELF-ASSEMBLING INTO NANOPARTICLES

REFERENCE TO AN ELECTRONIC SEQUENCE LISTING

The contents of the electronic sequence listing (0192-0126US1_SL.txt; Size: 40.0 KB; and Date of Creation Dec. 14, 2020) is herein incorporated by reference in its entirety.

The present invention relates to the field of polypeptides self-assembling into nanoparticles. In particular, the invention relates to a polypeptide comprising an amino acid sequence I (SEQ ID NO: 1), a nucleic acid sequence encoding said polypeptide, a nanoparticle comprising at least one polypeptide of the invention, a complex comprising said nanoparticle and one or more negatively cargo molecules and a method for transfecting a cell with said complex.

RELATED ART

Although oligonucleotides (ONs) are a class of molecular medicines that has numerous potential clinical applications, their suboptimal pharmacokinetic properties have substantially hindered drug development (Whitehead, K. A. et al., Nat. Rev. Drug Discov. 2009, 8, 129-138). In particular, the intracellular delivery of ONs remains an important hurdle, since ONs are rather large, highly charged entities and do not enter into cells by diffusion (Lundin, K. E. et al., Oligonucleotide Therapies: The Past and the Present. Hum. Gene Ther. 2015, 26, 475-485). Further concerns with in vivo application include susceptibility to nucleases present in biological sera leading to rapid degradation as well as urinary excretion and undesired off-target effects as well as activation of intra- and extracellular immune responses.

To overcome these disadvantages, the use of oligonucleotide delivery systems were suggested such as virus-like particles (VLPs) derived from bacteriophage P22 (Qazi, S. et al., Mol. Pharm. 2016, 13, 1191-1196) or Q virus-like particles (VLPs) functional nanoparticles (Fang, P. Y. et al., Nucleic Acids Res. 2017, 45, 3519). However, the production of virus-like particles that carry a desired therapeutic cargo is complex, expensive and still associated with safety concerns.

Although a wide range of materials has been suggested as oligonucleotide delivery vectors, simple, effective, safe and non-toxic delivery solutions are still sought (Whitehead, K. A. et al., Knocking down barriers: advances in siRNA delivery. Nat. Rev. Drug Discov. 2009, 8, 129-138). Recently, the development of computationally designed proteins capable of self-assembling into highly ordered and symmetric cage-like nanostructures have been described (King, N. P. et al., Science, 2012, 336, 1171-1174; U.S. Pat. No. 9,630,994 B2). Moreover, the design of such self-assembling protein nanocages referring to enveloped protein nanocages (EPNs) that direct their own release from human cells inside small vesicles have recently been described. One of the designed symmetrical self-assembling scaffold supporting EPN formation when fused to an N-terminal p6Gag peptide and a C-terminal PH domain was named O3-33 (King, et al., 2012, op.cit.; J. Votteler, et al., Nature, 2016, 540, 292-295).

SUMMARY OF THE INVENTION

The present invention provides designed and non-naturally occurring novel polypeptides that are not only capable of self-assembling into nanoparticles, but said nanoparticles are furthermore capable of encapsulating negatively charged macromolecules such as oligonucleotides with high binding affinity and delivering said macromolecules in vitro as well as in vivo. It has further been found that preferred nanoparticles of the present invention are efficiently taken up by mammalian cells and are able to release their cargo to induce, for example, RNA interference and knock down gene expression. Thus, the designed and non-naturally occurring novel polypeptides were engineered to result in nanoparticles allowing cargo delivery, in particular nucleic acid delivery, while minimizing or avoiding undesirable properties of delivery vehicles of the prior art.

Importantly, the nanoparticles of the present invention are easily produced and purified in high yields and allow to package in vitro any macromolecule, in particular, any oligonucleotide into said nanoparticle. Moreover, the nanoparticle of the invention, thus, provides a general platform useful to deliver said broad variety of cargo intracellularly, such as therapeutic ONs to, for example, modulate gene expression for various different applications, such as genetic interference. Thus, their usefulness encompasses biotechnology applications as well as therapeutic applications. Furthermore, the nanoparticles of the invention have typically a uniform size and, notably, are safe and well tolerated in vivo, and are, further typically biodegradable. Additionally, the designed and non-naturally occurring novel polypeptides can easily be produced, typically and preferably, by recombinant expression, which is scalable, economic and allows both genetic and post-translational (chemical) modifications. Tailoring of the properties of inventive nanoparticles further allows the nanoparticles not only to enter a cell but also to conditionally release the cargo within the cytoplasm to control, e.g., gene expression as described.

Thus, the non-naturally occurring novel polypeptide developed by the inventors self-assembles into a nanoparticle, which is capable of encapsulation and delivering cargo, preferably negatively charged macromolecules such as ONs.

Thus, in a first aspect, the present invention provides for a polypeptide comprising an amino acid sequence I consisting of:

(SEQ ID NO: 1)

$MX_{13}QAIGILELX_{1}SIAAGMELGDAMLKSAX_{14}VX_{15}LLVSKTISX_{2}GK$ $FLLMLGGDIX_{8}AIX_{9}X_{12}AIX_{10}TGTX_{11}QAGX_{3}LLVDSLVLAX_{16}IHP$ $SVLPAIX_{17}GX_{18}NX_{19}VX_{20}X_{7}X_{21}QAVGIVETX_{4}SVAACISAADX_{22}$ $AVX_{23}GSX_{24}VTLVRVHMAX_{5}GIGGKCYMVVAGDVSDVALAVTVASSSA$ $GAYGX_{6}LVYASLIPX_{25}PHX_{26}AMWX_{27}QMVX_{28}GX_{29}E$, wherein any of $X_1$ to $X_{29}$ are independently of each other an amino acid, provided that at least 3 of $X_1$ to $X_6$ are independently of each other a positively charged amino acid, and wherein optionally up to 5 amino acids in positions other than denoted by $X_1$ to $X_{29}$ in SEQ ID NO: 1 are exchanged by any amino acid.

In a further aspect, the present invention provides for a nucleic acid sequence encoding the polypeptide of the invention.

In a further aspect, the present invention provides for a nanoparticle comprising at least one polypeptide of the invention.

In a further aspect, the present invention provides for a complex comprising the nanoparticle of the invention and one or more cargo molecules, wherein said one or more cargo molecules are encapsulated in said nanoparticle.

In a further aspect, the present invention provides for a method for transfecting a cell comprising the step of contacting said cell with the complex of the invention.

In a further aspect, the invention provides a method for manufacturing the nanoparticle of the invention comprising the step of self-assembling of the polypeptide of the invention into said nanoparticle.

In a further aspect, the invention provides a method for manufacturing the complex of the invention comprising the step of mixing the nanoparticle of the invention with one or more negatively charged macromolecules.

In a further aspect, the invention relates to use of the complex of the invention for transfecting a cell.

OTR503. Lane 13: OP. Lane 14: Atto488-ssDNA. The broad band arises from an impurity of the DNA batch. (b) The proteins were visualized with Coomassie blue.

Figure 27A:
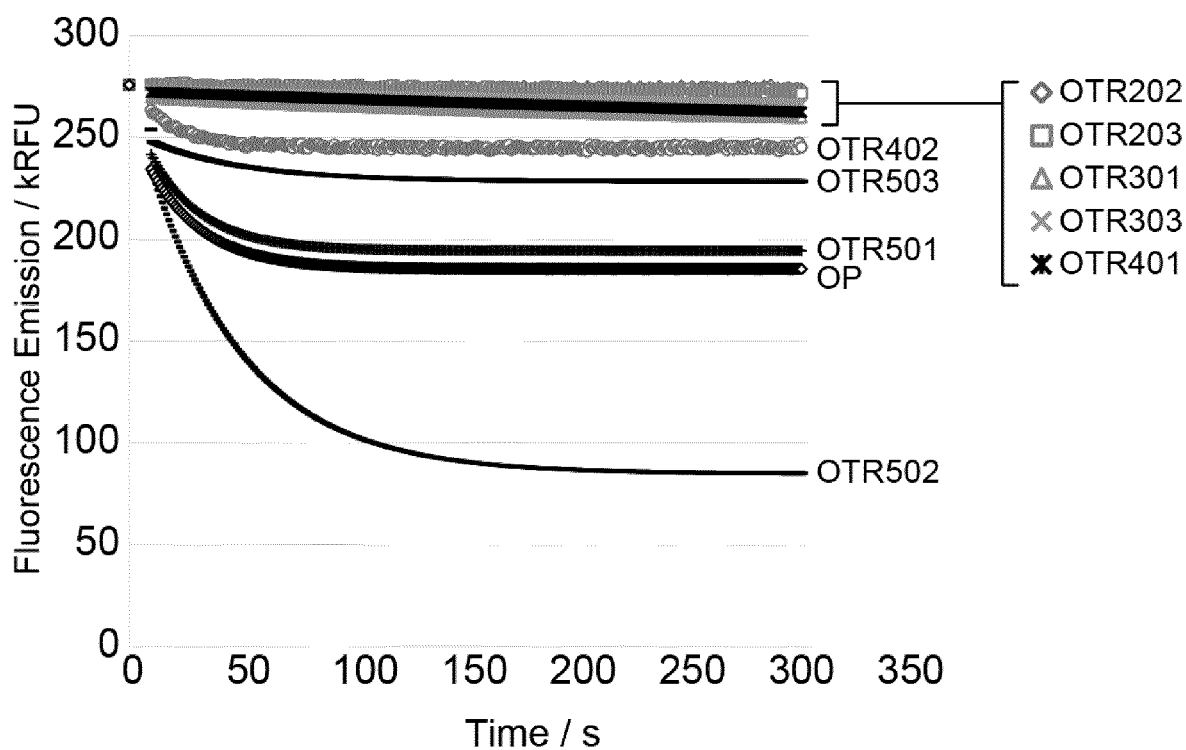
Figure 27B:
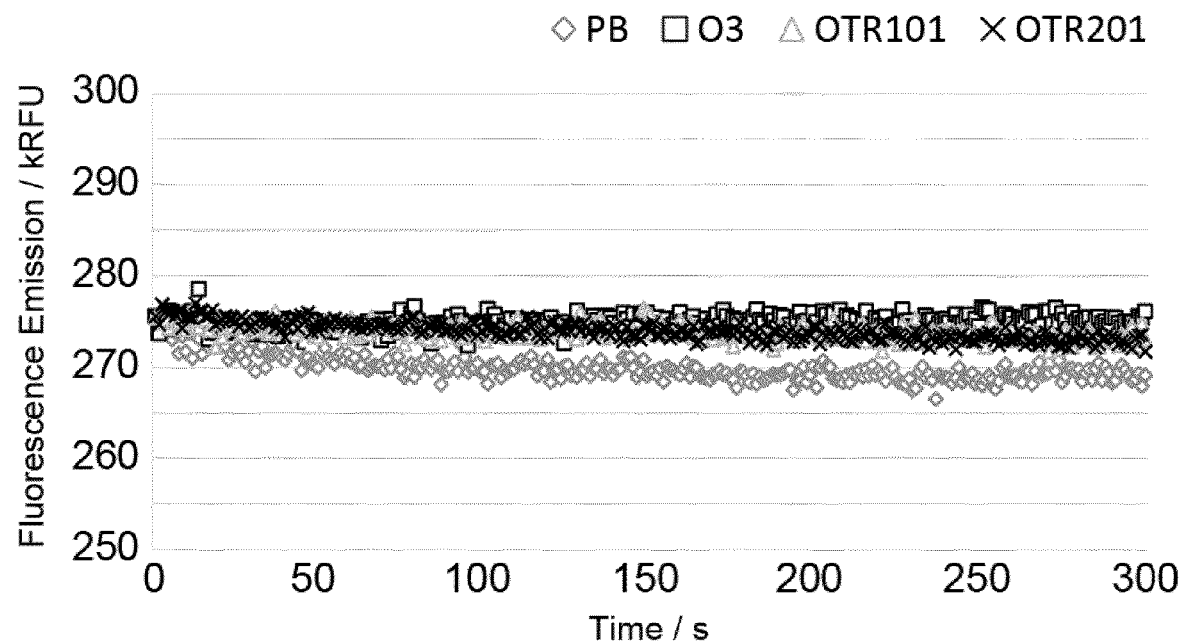

FIG. 27: Fluorescence quenching upon ssDNA encapsulation. (a) Fluorescence decay of all variants at 50 nM concentration protein in 10 nM Atto-488 ssDNA. This shows that the speed of this decay depends on the number and on the position of arginines. (b) Close-up view of the slow variants in (a). Here, it is clearly visible that O3-33, OTR101, OTR201, OTR202 and OTR203 do not bind ssDNA.

Figure 28:
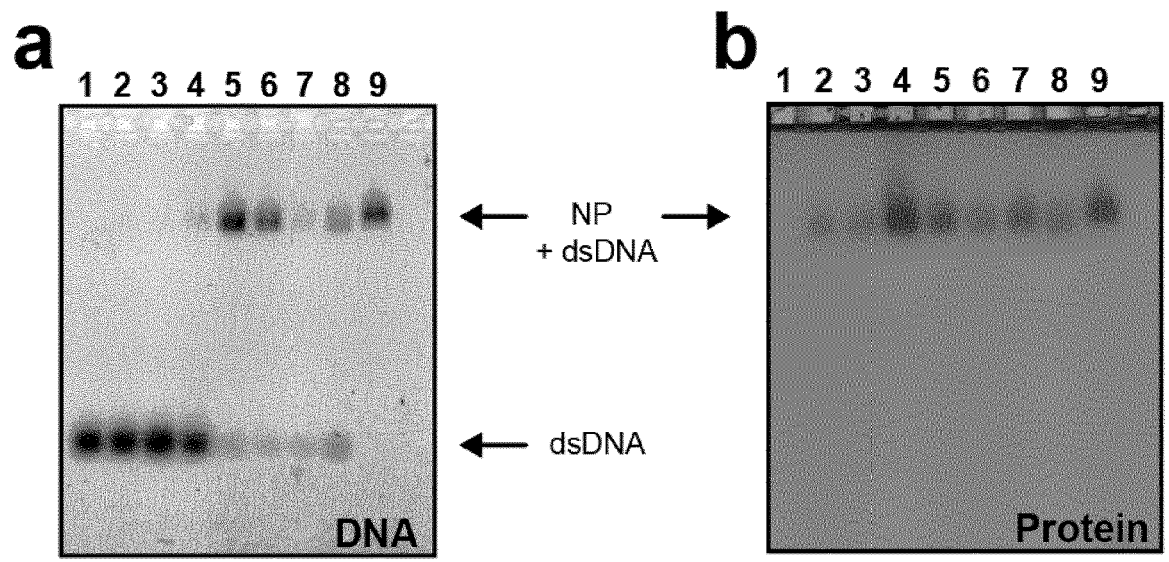

FIG. 28: In vitro studies of dsDNA loading into nanoparticles (NP). (a) Native AGE visualized by Atto-488 absorbance for hpDNA. (b) The same gel after staining with Coomassie Blue for protein visualization. Lane 1: hpDNA. Lane 2: OTR301. Lane 3: OTR302. Lane 4: OTR401. Lane 5: OTR402. Lane 6: OTR501. Lane 7: OTR502. Lane 8: OTR503. Lane 9: OP.

Figure 29:
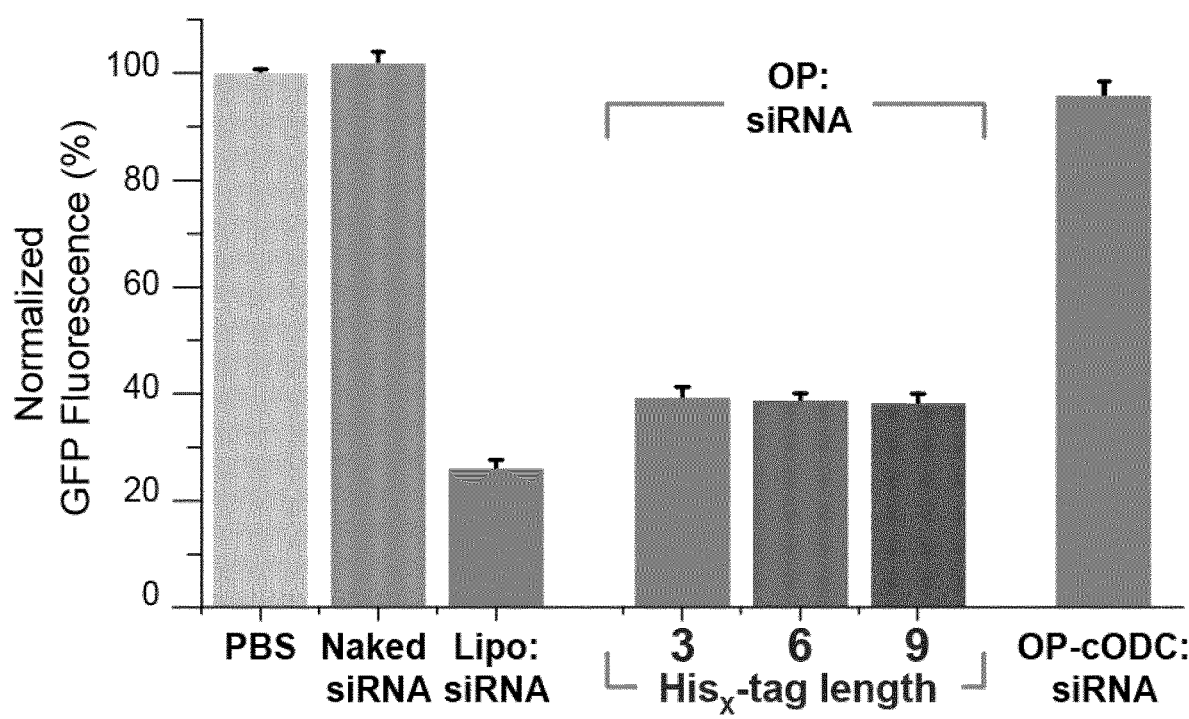

FIG. 29: GFP knockdown determined by flow cytometry (n=3).

Figure 30:
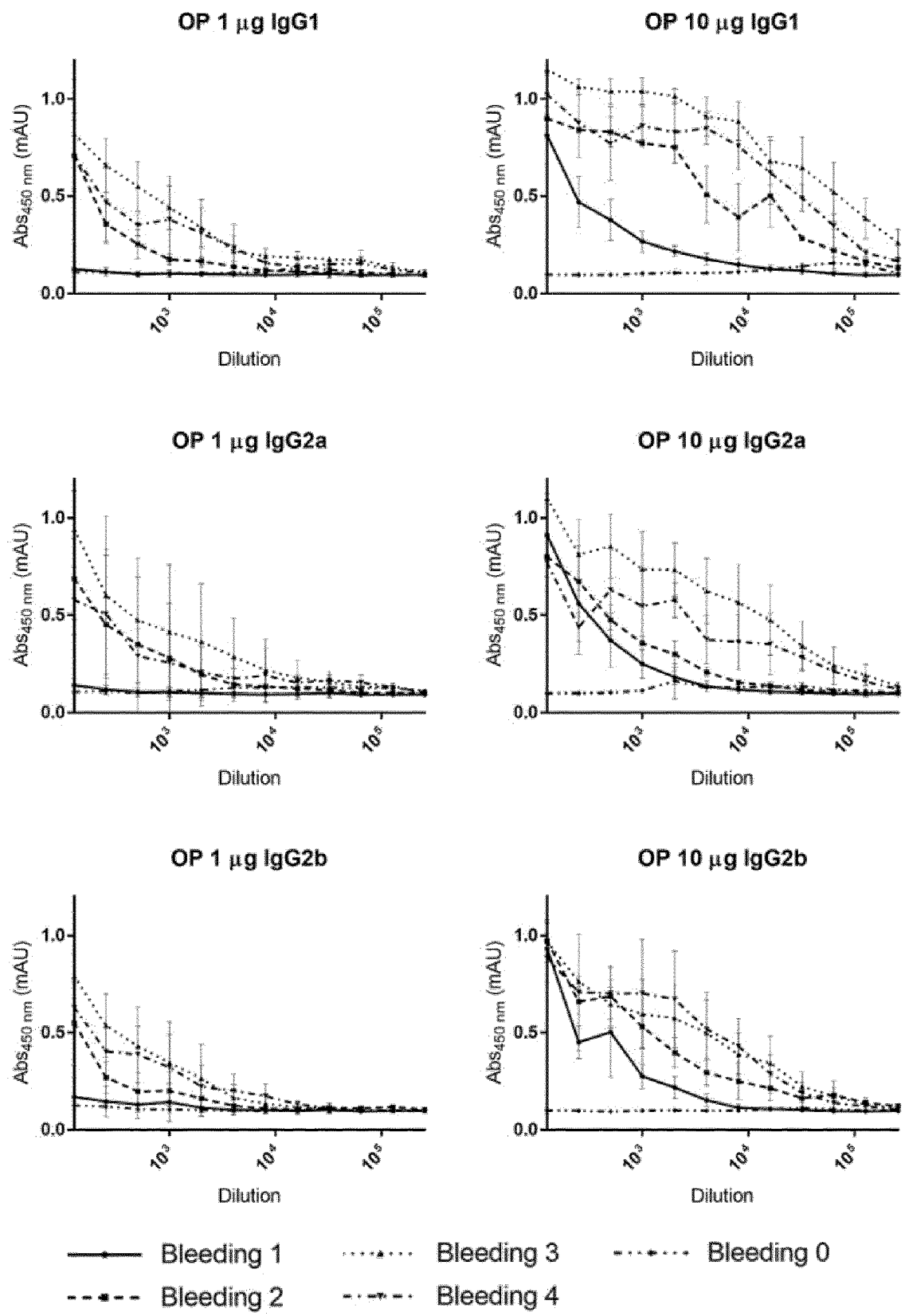

FIG. 30: Immunogenicity of OP cage in mice determined by ELISA. OP-specific IgG1 (a), IgG2a (b) and IgG2b (c) antibody titers were determined in serum from BALB/c mice immunized with OP as indicated by arrows. Each point is the mean IgG titer from 4 mice.

Figure 31:
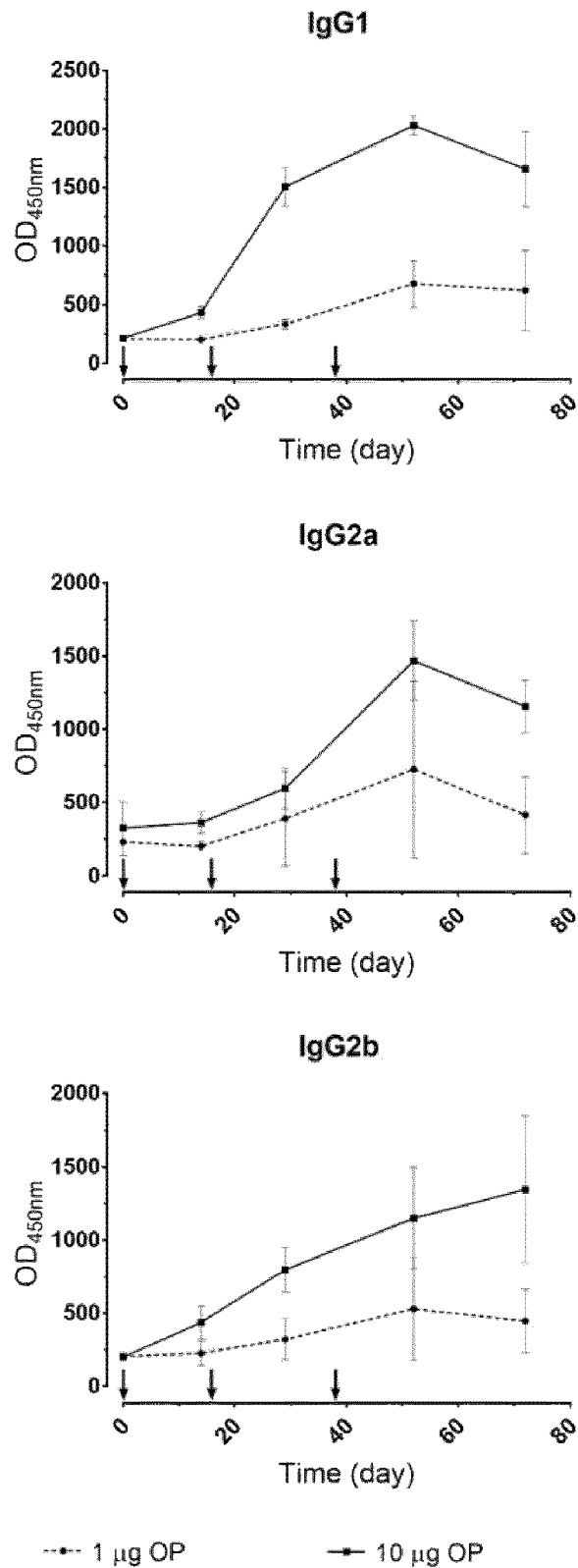

FIG. 31: Immunogenicity time course for OP cages in mice determined by ELISA. OP-specific IgG1 (a), IgG2a (b) and IgG2b (c) antibody titers were determined in serum from BALB/c mice immunized with OP as indicated by arrows. Each point is the mean IgG titer from 4 mice.

DETAILED DESCRIPTION OF THE INVENTION

Unless defined otherwise, all technical and scientific terms used herein have the same meanings as commonly understood by one of ordinary skill in the art to which this invention belongs.

Throughout this specification and the claims which follow, unless the context requires otherwise, the word "comprise" or the word "include", and variations such as "comprises/includes" and "comprising/including", are to be understood to imply the inclusion of an element, stated integer, step or a group thereof but not the exclusion of any other element, stated integer, step or a group thereof.

As used in this specification and the appended claims, the singular forms "a", "an", and "the" include plural referents, unless the content clearly dictates otherwise.

The term "about" or "approximately", when used in connection with a numerical value is meant to encompass numerical values within a range having a lower limit that is 0-10% smaller than the indicated numerical value and having an upper limit that is 0-10% larger than the indicated numerical value. The term "about" or "approximately" means preferably ±10%, more preferably ±5%, again more preferably ±33% or most preferably ±0% (referring to the given numeric value, respectively). In each of the invention embodiments, "about" can be deleted. All ranges of values disclosed herein, should refer and include to any and all values falling within said range including the values defining the range.

In a first aspect, the invention refers to a polypeptide comprising an amino acid sequence I consisting of:

(SEQ ID NO: 1)

-continued

MX$_{13}$QAIGILELX$_1$SIAAGMELGDAMLKSAX$_{14}$VX$_{15}$LLVSKTISX$_2$GK

FLLMLGGDIX$_8$AIX$_9$X$_{12}$AIX$_{10}$TGTX$_{11}$QAGX$_3$LLVDSLVLAX$_{16}$IHP

SVLPAIX$_{17}$GX$_{18}$NX$_{19}$VX$_{20}$X$_7$X$_{21}$QAVGIVETX$_4$SVAACISAADX$_{22}$

AVX$_{23}$GSX$_{24}$VTLVRVHMAX$_5$GIGGKCYMVVAGDVSDVALAVTVASSSA

GAYGX$_6$LVYASLIPX$_{25}$PHX$_{26}$AMWX$_{27}$QMVX$_{28}$GX$_{29}$E, wherein any of $X_1$ to $X_{29}$ is independently of each other an amino acid, provided that at least 3 of $X_1$ to $X_6$ are independently of each other a positively charged amino acid, and wherein optionally up to 5 amino acids in positions other than denoted by $X_1$ to $X_{29}$ in SEQ ID NO: 1 are exchanged by any amino acid.

In a preferred embodiment, said polypeptide comprises an amino acid sequence I consisting of SEQ ID NO: 1, wherein any of $X_1$ to $X_{29}$ is independently of each other an amino acid, provided that at least 3 of $X_1$ to $X_6$ are independently of each other a positively charged amino acid.

The term "polypeptide" as used herein refers to any peptide-bond-linked polymer of amino acids, regardless of size, length, secondary and tertiary structure, number of subunits or post-translational modification. Thus, the term "polypeptide" is to be understood as covering the terms "peptide", "protein", "amino acid chain", "amino acid sequence". Polypeptides in accordance with the invention can be an open linear peptide chain or cyclic peptides; alternatively or additionally, peptides of the invention may include at least one chemical modification, such as lipidation, glycosylation and phosphorylation. Peptides, as understood herein, especially peptides of the invention, are isolated or, preferably can be produced by chemical synthesis, RNA translation and/or recombinant processes.

The term "amino acid", as used herein, refers to organic compounds containing the functional groups amine (—NH2) and carboxylic acid (—COOH) and its zwitterions, typically and preferably, along with a side chain specific to each amino acid. The term "amino acid" typically and preferably includes amino acids that occur naturally, such as proteinogenic amino acids (produced by RNA-translation), non-proteinogenic amino acids (produced by other metabolic mechanisms, e.g. posttranslational modification), standard or canonical amino acids (that are directly encoded by the codons of the genetic code) and non-standard or non-canonical amino acids (not directly encoded by the genetic code). Naturally occurring amino acids include non-eukaryotic and eukaryotic amino acids. The term "amino acid", as used herein, also includes unnatural amino acids that are chemically synthesized. Moreover, the term covers alpha- (α-), beta- (β-), gamma- (γ-) and delta- (δ-) etc. amino acids as well as mixtures thereof in any ratio, and, if applicable, any isomeric form of an amino acid, i.e. its D- and L-stereoisomers (alternatively addressed by the (R) and (S) nomenclature) as well as mixtures thereof in any ratio, preferably in a racemic ratio of 1:1. Amino acids in this invention are typically and preferably in L-configuration. The term "D-stereoisomer", "L-stereoisomer", "D-amino acid" or "L-amino acid" refers to the chiral alpha carbon of the amino acids. Amino acid can include modifications and/or attached compounds and residues, for example residues used for peptide synthesis, such as Boc, Fmoc or both.

The terms "$X_n$ to $X_m$" and "$X_{n\text{-}m}$" are used interchangeably herein for denoting certain amino acid positions in SEQ ID NO: 1.

Optionally up to 5 amino acids in positions other than denoted by $X_{1\text{-}29}$ in SEQ ID NO: 1 can be exchanged by any amino acid. The term "amino acid exchange" or "exchanged by any amino acid" used interchangeably herein includes or preferably refers to an exchange by deletion of one amino acid or substitution of a single amino acid by one or more amino acids (addition), more preferably by one, two or three amino acids. Most preferably, the term "amino acid exchange" refers to deletion of a single amino acid or substitution of a single amino acid by one, two or three amino acids. In a preferred embodiment, said amino acid exchange is a substitution. In another preferred embodiment, said amino acid exchange is a conservative amino acid substitution.

The term "conservative substitution" is an amino acid substitution that changes a given amino acid to a different amino acid with similar biochemical properties. Conservative substitutions include and preferably refer to isosteric substitutions and substitutions where the charged, polar, aromatic, aliphatic or hydrophobic nature of the amino acid is maintained. Conservative substitutions refer to substitutions that maintain the capability of the polypeptide of the invention to self-assemble into the nanoparticle, preferably the cage-like nanoparticle of the invention.

The term "positively charged" as used herein includes and preferably refers to a molecule that has a positively charged group. More preferably, said positively charged molecule has a positively charged group at neutral or physiological pH.

In preferred embodiments of the present invention, optionally up to 4 amino acids, more preferably up to 3 amino acids, again more preferably up to 2 amino acids, most preferably 1 amino acid in positions other than denoted by $X_{1-29}$ in SEQ ID NO: 1 is/are exchanged by any amino acid.

In a preferred embodiment, said polypeptide has a length of about 500 amino acids or less, preferably about 400 amino acids or less, more preferably 300 amino acids or less, again more preferably 250 amino acids or less, again more preferably 200 amino acids or less, again more preferably from 188 to 230 amino acids, most preferably 192 amino acids.

In another preferred embodiment, said polypeptide is an isolated polypeptide.

In another preferred embodiment, said polypeptide consists of an amino acid sequence consisting of SEQ ID NO: 1. In another preferred embodiment, said polypeptide consists of an amino acid sequence consisting of SEQ ID NO: 1, wherein optionally up to 5 amino acids in positions other than denoted by $X_{1-29}$ in SEQ ID NO: 1 are exchanged by any amino acid.

In another preferred embodiment, said positively charged amino acids of said at least 3 of $X_1$ to $X_6$ are independently of each other arginine or a conservative substitution of arginine. In another preferred embodiment, said positively charged amino acids of said at least 3 of said $X_1$ to $X_6$ are independently of each other selected from the group consisting of arginine, 5-methyl-arginine, c-gamma-hydroxy arginine, 2-amino-4-guanidinobutryric acid, 2-amino-3-guanidinopropionic acid, canavanine, homoarginine, lysine, diaminobutyric acid, 2,3-diaminopropanoic acid, (2s)-2,8-diaminooctanoic acid, ornithine, thialysine and histidine.

In another preferred embodiment, said positively charged amino acids of said at least 3 of $X_1$ to $X_6$ are independently of each other selected from the group consisting of arginine, 5-methyl-arginine, c-gamma-hydroxy arginine, 2-amino-4-guanidinobutryric acid, 2-amino-3-guanidinopropionic acid, canavanine, homoarginine, lysine, diaminobutyric acid, 2,3-diaminopropanoic acid, (2s)-2,8-diaminooctanoic acid, ornithine and thialysine.

In another more preferred embodiment, said positively charged amino acid of said at least 3 of $X_1$ to $X_6$ is independently of each histidine, arginine or lysine. In another more preferred embodiment, said positively charged amino acid of said at least 3 of $X_1$ to $X_6$ is independently of each arginine or lysine. In another more preferred embodiment, said at least 3 positively charged amino acid of said $X_1$ to $X_6$ are independently of each arginine. In another more preferred embodiment, said at least 3 positively charged amino acid of said $X_1$ to $X_6$ are independently of each arginine. In one embodiment, each of said positively charged amino acids $X_1$ to $X_6$ is arginine. In one embodiment, each of said positively charged amino acids $X_1$ to $X_6$ is lysine.

In a preferred embodiment, said polypeptide of the invention comprises a histidine tag (His tag) consisting of 3 or more consecutive histidines, wherein said His tag is attached to the C- or N-terminus, preferably the C-terminus of the amino acid sequence I, and wherein in sequence I said positively charged amino acid of said at least 3 of $X_1$ to $X_6$ is independently arginine or lysine. In a preferred embodiment, said polypeptide of the invention comprises a histidine tag (His tag) consisting of 3 or more consecutive histidines, wherein said His tag is attached to the C- or N-terminus, preferably the C-terminus of the amino acid sequence I, and wherein in sequence I said positively charged amino acid of said at least 3 of $X_1$ to $X_6$ is arginine. In a preferred embodiment, said polypeptide of the invention comprises a histidine tag (His tag) consisting of 3 or more consecutive histidines, wherein said His tag is attached to the C- or N-terminus, preferably the C-terminus of the amino acid sequence I, and wherein in sequence I said positively charged amino acid of said at least 3 of $X_1$ to $X_6$ is lysine.

In a preferred embodiment, said polypeptide of the invention comprises a histidine tag (His tag) consisting of 3 to 9 consecutive histidines, wherein said His tag is attached to the C- or N-terminus, preferably the C-terminus of the amino acid sequence I, and wherein said positively charged amino acid of said at least 3 of $X_1$ to $X_6$ is independently arginine or lysine. In a preferred embodiment, said polypeptide of the invention comprises a histidine tag (His tag) consisting of 3 to 9 consecutive histidines, wherein said His tag is attached to the C- or N-terminus, preferably the C-terminus of the amino acid sequence I, and wherein said positively charged amino acid of said at least 3 of $X_1$ to $X_6$ is arginine. In a preferred embodiment, said polypeptide of the invention comprises a histidine tag (His tag) consisting of 3 to 9 consecutive histidines, wherein said His tag is attached to the C- or N-terminus, preferably the C-terminus of the amino acid sequence I, and wherein said positively charged amino acid of said at least 3 of $X_1$ to $X_6$ is lysine.

$X_7$ is cysteine, a conservative substitution thereof or a positively charged amino acid.

In a preferred embodiment, said conservative substitution of cysteine is selected from the group consisting of methionine, homocysteine, selenocysteine, serine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, homoserine, 3-hydroxy-l-valine, 4,5-dihydroxy-isoleucine, 6-hydroxy-l-norleucine, s-(2-hydroxyethyl)-l-cysteine, phosphoserine, 4-hydroxy-l-threonine, threonine, and phosphothreonine. In a preferred embodiment, said conservative substitution of cysteine is selected from the group consisting of homocysteine, selenocysteine, serine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, homoserine, 3-hydroxy-l-valine, 4,5-dihydroxy-isoleucine, 6-hydroxy-l-norleucine, s-(2-hydroxyethyl)-l-cysteine, phosphoserine, 4-hydroxy-l-threonine, threonine, and phosphothreonine. More preferably, said conservative substitution of cysteine is selected from the group consisting of homocysteine, selenocysteine, and serine. Again more preferably, said conservative substitution of cysteine is homocysteine or selenocysteine.

In another preferred embodiment, $X_7$ is selected from the group consisting of homocysteine, selenocysteine, cysteine, arginine, 5-methyl-arginine, c-gamma-hydroxy arginine, 2-amino-4-guanidinobutryric acid, 2-amino-3-guanidinopropionic acid, canavanine, homoarginine, lysine, diaminobutyric acid, 2,3-diaminopropanoic acid, (2s)-2,8-diaminooctanoic acid, ornithine and thialysine.

In another preferred embodiment, $X_7$ is selected from the group consisting of homocysteine, selenocysteine, serine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, homoserine, 3-hydroxy-l-valine, 4,5-dihydroxy-isoleucine, 6-hydroxy-l-norleucine, s-(2-hydroxyethyl)-l-cysteine, phosphoserine, 4-hydroxy-l-threonine, threonine, and phosphothreonine, arginine, 5-methyl-arginine, c-gamma-hydroxy arginine, 2-amino-4-guanidinobutryric acid, 2-amino-3-guanidinopropionic acid, canavanine, homoarginine, lysine, diaminobutyric acid, 2,3-diaminopropanoic acid, (2s)-2,8-diaminooctanoic acid, ornithine and thialysine. In another preferred embodiment, said $X_7$ is selected from arginine, lysine, serine, homocysteine, or cysteine. In another further preferred embodiment, said $X_7$ is selected from arginine, lysine, homocysteine, or cysteine.

If $X_7$ is cysteine or a conservative substitution of cysteine it could be used to append positively charged groups via disulfide formation (e.g. cysteamine, 1-(3-mercaptopropyl) guanidine etc.) to the polypeptide of the invention.

In one embodiment, said at least 3 of said $X_1$ to $X_6$ are independently of each other lysine or arginine, and said $X_7$ is selected from arginine, lysine, serine, homocysteine or cysteine.

In amino acid sequence I consisting of SEQ ID NO: 1, at least 3 of said amino acids $X_1$ to $X_6$ are independently of each other positively charged amino acids. In a preferred embodiment, at least 4, more preferably at least 5, again more preferably 6, i.e. each of said amino acids $X_1$ to $X_6$ is/are independently of each other a positively charged amino acid.

In a preferred embodiment, at least 4, preferably at least 5, more preferably 6, i.e. each of said amino acids $X_1$ to $X_6$ is/are independently of each other a positively charged amino acid, wherein said positively charged amino acid is arginine or lysine. In a preferred embodiment, at least 4, preferably at least 5, more preferably each of said amino acids of $X_1$ to $X_6$ is/are independently of each other a positively charged amino acids wherein said positively charged amino acids are arginine. In a preferred embodiment, at least 4, preferably at least 5, more preferably 6 of said amino acids $X_1$ to $X_6$ are independently of each other positively charged amino acids, wherein said positively charged amino acids are lysine.

In a preferred embodiment, said at least 3 of $X_1$ to $X_6$ being independently of each other a positively charged amino acid are $X_1$ to $X_3$. In another preferred embodiment, said at least 3 of $X_1$ to $X_6$ being independently of each other a positively charged amino acid are $X_1$, $X_2$, and $X_4$. In another preferred embodiment, said at least 3 of $X_1$ to $X_6$ being independently of each other a positively charged amino acid are $X_1$, $X_2$, and $X_5$. In another preferred embodiment, said at least 3 of $X_1$ to $X_6$ being independently of each other a positively charged amino acid are $X_1$, $X_2$, and $X_6$.

In another preferred embodiment, said at least 3 of $X_1$ to $X_6$ being independently of each other a positively charged amino acid are $X_2$, $X_3$, and $X_4$. In another preferred embodiment, said at least 3 of $X_1$ to $X_6$ being independently of each other a positively charged amino acid are $X_2$, $X_3$, and $X_5$. In another preferred embodiment, said at least 3 of $X_1$ to $X_6$ being independently of each other a positively charged amino acid are $X_2$, $X_3$, and $X_6$.

In another preferred embodiment, said at least 3 of $X_1$ to $X_6$ being independently of each other a positively charged amino acid are $X_3$, $X_4$, and $X_5$. In another preferred embodiment, said at least 3 of $X_1$ to $X_6$ being independently of each other a positively charged amino acid are $X_3$, $X_4$, and $X_6$. In another preferred embodiment, said at least 3 of $X_1$ to $X_6$ being independently of each other a positively charged amino acid are $X_3$, $X_4$, and $X_1$.

In another preferred embodiment, said at least 3 of $X_1$ to $X_6$ being independently of each other a positively charged amino acid are $X_4$, $X_5$, and $X_6$. In another preferred embodiment, said at least 3 of $X_1$ to $X_6$ being independently of each other a positively charged amino acid are $X_4$, $X_5$, and $X_1$. In another preferred embodiment, said at least 3 of $X_1$ to $X_6$ being independently of each other a positively charged amino acid are $X_4$, $X_5$, and $X_2$.

In another preferred embodiment, said at least 3 of $X_1$ to $X_6$ being independently of each other a positively charged amino acid are $X_5$, $X_6$, and $X_1$. In another preferred embodiment, said at least 3 of $X_1$ to $X_6$ being independently of each other a positively charged amino acid are $X_5$, $X_6$, and $X_2$. In another preferred embodiment, said at least 3 of $X_1$ to $X_6$ being independently of each other a positively charged amino acid are $X_5$, $X_6$, and $X_3$.

In another preferred embodiment, said at least 3 of $X_1$ to $X_6$ being independently of each other a positively charged amino acid are $X_1$, $X_3$, and $X_5$. In another preferred embodiment, said at least 3 of $X_1$ to $X_6$ being independently of each other a positively charged amino acid are $X_1$, $X_3$, and $X_6$. In another preferred embodiment, said at least 3 of $X_1$ to $X_6$ being independently of each other a positively charged amino acid are $X_2$, $X_4$, and $X_6$. In another preferred embodiment, said at least 3 of $X_1$ to $X_6$ being independently of each other a positively charged amino acid are $X_1$, $X_4$, and $X_6$.

In another preferred embodiment, said at least 3 of $X_1$ to $X_6$ being independently of each other a positively charged amino acid are $X_1$, $X_2$, $X_3$, and $X_4$. In another preferred embodiment, said at least 3 of $X_1$ to $X_6$ being independently of each other a positively charged amino acid are $X_1$, $X_2$, $X_3$, and $X_5$. In another preferred embodiment, said at least 3 of $X_1$ to $X_6$ being independently of each other a positively charged amino acid are $X_1$, $X_2$, $X_3$, and $X_6$. In another preferred embodiment, said at least 3 of $X_1$ to $X_6$ being independently of each other a positively charged amino acid are $X_2$, $X_3$, $X_4$, and $X_5$. In another preferred embodiment, said at least 3 of $X_1$ to $X_6$ being independently of each other a positively charged amino acid are $X_2$, $X_3$, $X_4$, and $X_6$. In another preferred embodiment, said at least 3 of $X_1$ to $X_6$ being independently of each other a positively charged amino acid are $X_3$ to $X_6$. In another preferred embodiment, said at least 3 of $X_1$ to $X_6$ being independently of each other a positively charged amino acid are $X_2$, $X_4$, $X_5$, and $X_6$. In another preferred embodiment, said at least 3 of $X_1$ to $X_6$ being independently of each other a positively charged amino acid are $X_1$, $X_4$, $X_5$, and $X_6$. In another preferred embodiment, said at least 3 of $X_1$ to $X_6$ being independently of each other a positively charged amino acid are $X_1$, $X_3$, $X_5$, and $X_6$. In another preferred embodiment, said at least 3 of $X_1$ to $X_6$ being independently of each other a positively charged amino acid are $X_1$, $X_3$, $X_4$, and $X_6$. In another preferred embodiment, said at least 3 of $X_1$ to $X_6$ being independently of each other a positively charged amino acid are $X_2$, $X_3$, $X_4$, and $X_6$.

In another preferred embodiment, said at least 3 of $X_1$ to $X_6$ being independently of each other a positively charged amino acid are $X_{1\_5}$. In another preferred embodiment, said at least 3 of $X_1$ to $X_6$ being independently of each other a positively charged amino acid are $X_{1-4}$ and $X_6$. In another preferred embodiment, said at least 3 of $X_1$ to $X_6$ being independently of each other a positively charged amino acid are $X_{1-3}$, $X_5$ and $X_6$. In another preferred embodiment, said at least 3 of $X_1$ to $X_6$ being independently of each other a positively charged amino acid are $X_1$, $X_2$, and $X_4$ to $X_6$. In another preferred embodiment, said at least 3 of $X_1$ to $X_6$ being independently of each other a positively charged amino acid are $X_1$, and $X_{3-6}$. In another preferred embodiment, said at least 3 of $X_1$ to $X_6$ being independently of each other a positively charged amino acid are $X_2$ to $X_6$.

In another preferred embodiment, said at least 3 of $X_1$ to $X_6$ being independently of each other a positively charged amino acid are $X_1$ to $X_6$ are independently of each other positively charged amino acids.

More preferably, said at least 3 of $X_1$ to $X_6$ being independently of each other a positively charged amino acid are $X_1$ to $X_6$, or $X_4$ to $X_6$, or $X_1$, $X_2$ and $X_5$, or $X_1$, $X_2$, $X_4$, and $X_5$, or $X_1$, $X_3$, $X_4$, and $X_6$, or $X_1$ and $X_4$ to $X_6$, or $X_1$ to $X_3$ and $X_6$, or $X_1$ to $X_5$. More preferably, said at least 3 of $X_1$ to $X_6$ being independently of each other a positively charged amino acid are $X_1$ to $X_6$, or $X_4$ to $X_6$, or $X_1$, $X_2$ and $X_5$, or $X_1$, $X_2$, $X_4$, and $X_5$, or $X_1$, $X_3$, $X_4$, and $X_6$, or $X_1$ and $X_4$ to $X_6$, or $X_1$ to $X_3$ and $X_6$, or $X_1$ to $X_5$.

In a preferred embodiment, $X_4$ to $X_6$ are independently of each other lysine or arginine. In another preferred embodiment, $X_1$, $X_2$, and $X_4$ are independently of each other lysine or arginine. In another preferred embodiment, $X_1$, $X_2$, $X_4$, and $X_5$ are independently of each other lysine or arginine. In another preferred embodiment, $X_1$, $X_3$, $X_4$, and $X_6$ are independently of each other lysine or arginine. In another preferred embodiment, $X_1$, and $X_3$ to $X_6$ are independently of each other independently of each other lysine or arginine. In another preferred embodiment, $X_{1-3}$, $X_5$ and $X_6$ are independently of each other lysine or arginine. In another preferred embodiment, $X_{1-5}$ are independently of each other lysine or arginine. In another preferred embodiment, $X_1$ to $X_6$ are independently of each other lysine or arginine.

In a preferred embodiment, said polypeptide of the invention comprises a histidine tag (His tag) consisting of 3 to 9 consecutive histidines, wherein said His tag is attached to the C- or N-terminus, preferably the C-terminus of the amino acid sequence I, and wherein each of $X_1$ to $X_6$ is independently arginine or lysine. In a preferred embodiment, said polypeptide of the invention comprises a histidine tag (His tag) consisting of 3 to 9 consecutive histidines, wherein said His tag is attached to the C- or N-terminus, preferably the C-terminus of the amino acid sequence I, and wherein each of $X_1$ to $X_6$ is arginine. In a preferred embodiment, said polypeptide of the invention comprises a histidine tag (His tag) consisting of 3 to 9 consecutive histidines, wherein said His tag is attached to the C- or N-terminus, preferably the C-terminus of the amino acid sequence I, and wherein each of $X_1$ to $X_6$ is lysine.

In another preferred embodiment, $X_1$ to $X_6$ are independently of each other lysine or arginine and $X_7$ is selected from arginine, lysine or cysteine.

The inventors found out that amino acids at positions $X_8$ to $X_{12}$ define pore size of the nanoparticle formed via self-assembly by the polypeptide of the invention. Larger amino acid at positions $X_8$ to $X_{12}$ reduced pore size, while smaller amino acid at these positions increased nanoparticle pore size.

Thus, in a preferred embodiment, said amino acids at positions $X_8$ to $X_{12}$ in the polypeptide of the invention are selected such that cargo can be loaded into a nanoparticle comprising said polypeptide without disassembly. In another preferred embodiment, said amino acids at positions X8 to X12 in the polypeptide of the invention are selected such that cargo can be loaded into a nanoparticle comprising said polypeptide and released from said nanoparticle without disassembly. In another preferred embodiment, said amino acids at positions X8 to X12 in the polypeptide of the invention are selected such that cargo can be loaded in vitro into a nanoparticle comprising said polypeptide and released from said nanoparticle in vivo without disassembly. In another preferred embodiment, said amino acids at positions X8 to X12 in the polypeptide of the invention are selected such that cargo can be loaded extracellularly into a nanoparticle comprising said polypeptide and released from said nanoparticle intracellularly, preferably, into the cytoplasm of a cell, without disassembly. Preferably said cargo are negatively charged macromolecules, more preferably RNA, again more preferably RNA selected from the group consisting of antisense oligonucleotides (ASO), small interference RNA (siRNA), small hairpin RNA (shRNA), micro RNA (miRNA) and anti-miRNA, most preferably siRNA.

In another preferred embodiment, said amino acids at positions X8 to X12 in the polypeptide of the invention are selected such that a nanoparticle comprising at least a polypeptide of the invention comprises pores having a size of 3-4 nm and cargo can be loaded into a nanoparticle comprising said polypeptide without disassembly. In another preferred embodiment, said amino acids at positions X8 to X12 in the polypeptide of the invention are selected such that a nanoparticle comprising at least one polypeptide of the invention comprises pores having a size of 3-4 nm and cargo can be loaded into a nanoparticle comprising said polypeptide and released from said nanoparticle without disassembly. In another preferred embodiment, said amino acids at positions X8 to X12 in the polypeptide of the invention are selected such that a nanoparticle comprising at least one polypeptide of the invention comprises pores having a size of 3-4 nm, and cargo can be loaded in vitro into a nanoparticle comprising said polypeptide and released from said nanoparticle in vivo without disassembly. In another preferred embodiment, said amino acids at positions X8 to X12 in the polypeptide of the invention are selected such that a nanoparticle comprising at least one polypeptide of the invention comprises pores having a size of 3-4 nm, and cargo can be loaded extracellularly into a nanoparticle comprising said polypeptide and released from said nanoparticle intracellularly, preferably, into the cytoplasm of a cell, without disassembly. Preferably said cargo are negatively charged macromolecules, more preferably RNA, again more preferably RNA selected from the group consisting of antisense oligonucleotides (ASO), small interference RNA (siRNA), small hairpin RNA (shRNA), micro RNA (miRNA) and anti-miRNA, most preferably siRNA.

In a preferred embodiment, each of X8, X9, X10, X11 and X12 is independently selected from the group consisting of glycine, alanine, leucine, valine, tert-leucine, homoleucine, isoleucine, alloisoleucine 2-aminobutyric acid, diethylalanine, norleucine, norvaline; glutamine, asparagine, beta-hydroxyasparagine, 3-methyl-l-glutamine, (2s,4s)-2,5-diamino-4-hydroxy-5-oxopentanoic acid, n-methyl-asparagine; glutamate, aspartate 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid, 3-methyl-aspartic acid; serine, homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine, and said amino acids at positions X8 to X12 in the polypeptide of the invention are selected such that a nanoparticle comprising at least one polypeptide of the invention comprises pores having a size of 3-4 nm, wherein cargo can be loaded into said nanoparticle and released from said nanoparticle without disassembly. In a preferred embodiment, each of X8, X9, X10, X11 and X12 is independently selected from the group consisting of glycine, alanine, leucine, valine, tert-leucine, homoleucine, isoleucine, alloisoleucine 2-aminobutyric acid, diethylalanine, norleucine, norvaline; glutamine, asparagine, beta-hydroxyasparagine, 3-methyl-l-glutamine, (2s,4s)-2,5-diamino-4-hydroxy-5-oxopentanoic acid, n-methyl-asparagine; glutamate, aspartate 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid, 3-methyl-aspartic acid; serine, homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine, and said amino acids at positions X8 to X12 in the polypeptide of the invention are selected such that a nanoparticle comprising at least one polypeptide of the invention comprises pores having a size of 3-4 nm, wherein cargo can be loaded extracellularly into a nanoparticle comprising said polypeptide and released from said nanoparticle intracellularly, more preferably, into the cytoplasm of a cell, without disassembly. In a further preferred embodiment, each of X8, X9, X10, X11 and X12 is independently selected from the group consisting of glycine, alanine, leucine, valine; glutamate, aspartate; glutamine, asparagine; serine, threonine, and homoserine, said amino acids at positions X8 to X12 in the polypeptide of the invention are selected such that a nanoparticle comprising at least one polypeptide of the invention comprises pores having a size of 3-4 nm, wherein cargo can be loaded into a nanoparticle comprising said polypeptide and released from said nanoparticle without disassembly. In a further preferred embodiment, each of X8, X9, X10, X11 and X12 is independently selected from the group consisting of glycine, alanine, leucine, valine; glutamate, aspartate; glutamine, asparagine; serine, threonine, and homoserine, said amino acids at positions X8 to X12 in the polypeptide of the invention are selected such that a nanoparticle comprising at least one polypeptide of the invention comprises pores having a size of 3-4 nm, wherein cargo can be loaded extracellularly into a nanoparticle comprising said polypeptide and released from said nanoparticle intracellularly, more preferably, into the cytoplasm of a cell, without disassembly. In a further preferred embodiment, each of X8, X9, X10, X11 and X12 is independently selected from the group consisting of serine, glycine, glutamine, and glutamate, said amino acids at positions X8 to X12 in the polypeptide of the invention are selected such that a nanoparticle comprising at least one polypeptide of the invention comprises pores having a size of 3-4 nm, wherein cargo can be loaded into a nanoparticle comprising said polypeptide and released from said nanoparticle without disassembly. In a further preferred embodiment, each of X8, X9, X10, X11 and X12 is independently selected from the group consisting of serine, glycine, glutamine, and glutamate, said amino acids at positions X8 to X12 in the polypeptide of the invention are selected such that a nanoparticle comprising at least one polypeptide of the invention comprises pores having a size of 3-4 nm, wherein cargo can be loaded extracellularly into a nanoparticle comprising said polypeptide and released from said nanoparticle intracellularly, more preferably, into the cytoplasm of a cell, without disassembly. Preferably said cargo are negatively charged macromolecules, more preferably RNA, again more preferably RNA selected from the group consisting of antisense oligonucleotides (ASO), small interference RNA (siRNA), small hairpin RNA (shRNA), micro RNA (miRNA) and anti-miRNA, most preferably siRNA.

In a preferred embodiment, $X_1$ to X6 are independently of each other lysine or arginine; X7 is selected from arginine, lysine or cysteine; each of X8, X9, X10, X11 and X12 is independently selected from the group consisting of glycine, alanine, leucine, valine, tert-leucine, homoleucine, isoleucine, alloisoleucine 2-aminobutyric acid, diethylalanine, norleucine, norvaline; glutamine, asparagine, beta-hydroxyasparagine, 3-methyl-l-glutamine, (2s,4s)-2,5-diamino-4-hydroxy-5-oxopentanoic acid, n-methyl-asparagine; glutamate, aspartate 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid, 3-methyl-aspartic acid; serine, homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine, and said amino acids at positions X8 to X12 in the polypeptide of the invention are selected such that a nanoparticle comprising at least one polypeptide of the invention comprises pores having a size of 3-4 nm, wherein cargo can be loaded into said nanoparticle and released from said nanoparticle without disassembly. In a preferred embodiment, X1 to X6 are independently of each other lysine or arginine; X7 is selected from arginine, lysine or cysteine; each of X8, X9, X10, X11 and X12 is independently selected from the group consisting of glycine, alanine, leucine, valine, tert-leucine, homoleucine, isoleucine, alloisoleucine 2-aminobutyric acid, diethylalanine, norleucine, norvaline; glutamine, asparagine, beta-hydroxyasparagine, 3-methyl-l-glutamine, (2s,4s)-2,5-diamino-4-hydroxy-5-oxopentanoic acid, n-methyl-asparagine; glutamate, aspartate 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid, 3-methyl-aspartic acid; serine, homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine, and said amino acids at positions X8 to X12 in the polypeptide of the invention are selected such that a nanoparticle comprising at least one polypeptide of the invention comprises pores having a size of 3-4 nm, wherein cargo can be loaded extracellularly into a nanoparticle comprising said polypeptide and released from said nanoparticle intracellularly, more preferably, into the cytoplasm of a cell, without disassembly. In a further preferred embodiment, X1 to X6 are independently of each other lysine or arginine; X7 is selected from arginine, lysine or cysteine; each of X8, X9, X10, X11 and X12 is independently selected from the group consisting of glycine, alanine, leucine, valine; glutamate, aspartate; glutamine, asparagine; serine, threonine, and homoserine, said amino acids at positions X8 to X12 in the polypeptide of the invention are selected such that a nanoparticle comprising at least one polypeptide of the invention comprises pores having a size of 3-4 nm, wherein cargo can be loaded into a nanoparticle comprising said polypeptide and released from said nanoparticle without disassembly. In a further preferred embodiment, X1 to X6 are independently of each other lysine or arginine; X7 is selected from arginine, lysine or cysteine; each of X8, X9, X10, X11 and X12 is independently selected from the group consisting of glycine, alanine, leucine, valine; glutamate, aspartate; glutamine, asparagine; serine, threonine, and homoserine, said amino acids at positions X8 to X12 in the polypeptide of the invention are selected such that a nanoparticle comprising at least one polypeptide of the invention comprises pores having a size of 3-4 nm, wherein cargo can be loaded extracellularly into a nanoparticle comprising said polypeptide and released from said nanoparticle intracellularly, more preferably, into the cytoplasm of a cell, without disassembly. In a further preferred embodiment, X1 to X6 are independently of each other lysine or arginine; X7 is selected from arginine, lysine or cysteine; each of X8, X9, X10, X11 and X12 is independently selected from the group consisting of serine, glycine, glutamine, and glutamate, said amino acids at positions X8 to X12 in the polypeptide of the invention are selected such that a nanoparticle comprising at least one polypeptide of the invention comprises pores having a size of 3-4 nm, wherein cargo can be loaded into a nanoparticle comprising said polypeptide and released from said nanoparticle without disassembly. In a further preferred embodiment, X1 to X6 are independently of each other lysine or arginine; X7 is selected from arginine, lysine or cysteine; each of X8, X9, X10, X11 and X12 is independently selected from the group consisting of serine, glycine, glutamine, and glutamate, said amino acids at positions X8 to X12 in the polypeptide of the invention are selected such that a nanoparticle comprising at least one polypeptide of the invention comprises pores having a size of 3-4 nm, wherein cargo can be loaded extracellularly into a nanoparticle comprising said polypeptide and released from said nanoparticle intracellularly, more preferably, into the cytoplasm of a cell, without disassembly. Preferably said cargo are negatively charged macromolecules, more preferably RNA, again more preferably RNA selected from the group consisting of antisense oligonucleotides (ASO), small interference RNA (siRNA), small hairpin RNA (shRNA), micro RNA (miRNA) and anti-miRNA, most preferably siRNA.

In a preferred embodiment, X1 to X6 are independently of each other lysine or arginine; X7 is selected from arginine, lysine or cysteine; each of X8, X9, X10, X11 and X12 is independently selected from the group consisting of glycine, alanine, leucine, valine, tert-leucine, homoleucine, isoleucine, alloisoleucine 2-aminobutyric acid, diethylalanine, norleucine, norvaline; glutamine, asparagine, beta-hydroxyasparagine, 3-methyl-l-glutamine, (2s,4s)-2,5-diamino-4-hydroxy-5-oxopentanoic acid, n-methyl-asparagine; glutamate, aspartate 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid, 3-methyl-aspartic acid; serine, homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine, and said amino acids at positions X8 to X12 in the polypeptide of the invention are selected such that a nanoparticle comprising 6 of said polypeptides comprises 6 pores having a size of 3-4 nm, wherein cargo can be loaded into said nanoparticle and released from said nanoparticle without disassembly. In a preferred embodiment, X1 to X6 are independently of each other lysine or arginine; X7 is selected from arginine, lysine or cysteine; each of X8, X9, X10, X11 and X12 is independently selected from the group consisting of glycine, alanine, leucine, valine, tert-leucine, homoleucine, isoleucine, alloisoleucine 2-aminobutyric acid, diethylalanine, norleucine, norvaline; glutamine, asparagine, beta-hydroxyasparagine, 3-methyl-l-glutamine, (2s,4s)-2,5-diamino-4-hydroxy-5-oxopentanoic acid, n-methyl-asparagine; glutamate, aspartate 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid, 3-methyl-aspartic acid; serine, homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine, and said amino acids at positions X8 to X12 in the polypeptide of the invention are selected such that a nanoparticle comprising 6 of said polypeptides comprises 6 pores having a size of 3-4 nm, wherein cargo can be loaded extracellularly into a nanoparticle comprising said polypeptide and released from said nanoparticle intracellularly, more preferably, into the cytoplasm of a cell, without disassembly. In a further preferred embodiment, X1 to X6 are independently of each other lysine or arginine; X7 is selected from arginine, lysine or cysteine; each of X8, X9, X10, X11 and X12 is independently selected from the group consisting of glycine, alanine, leucine, valine; glutamate, aspartate; glutamine, asparagine; serine, threonine, and homoserine, said amino acids at positions X8 to X12 in the polypeptide of the invention are selected such that a nanoparticle comprising 6 of said polypeptides comprises 6 pores having a size of 3-4 nm, wherein cargo can be loaded into a nanoparticle comprising said polypeptide and released from said nanoparticle without disassembly. In a further preferred embodiment, X1 to X6 are independently of each other lysine or arginine; X7 is selected from arginine, lysine or cysteine; each of X8, X9, X10, X11 and X12 is independently selected from the group consisting of glycine, alanine, leucine, valine; glutamate, aspartate; glutamine, asparagine; serine, threonine, and homoserine, said amino acids at positions X8 to X12 in the polypeptide of the invention are selected such that a nanoparticle comprising 6 of said polypeptides comprises pores having a size of 3-4 nm, wherein cargo can be loaded extracellularly into a nanoparticle comprising said polypeptide and released from said nanoparticle intracellularly, more preferably, into the cytoplasm of a cell, without disassembly. In a further preferred embodiment, X1 to X6 are independently of each other lysine or arginine; X7 is selected from arginine, lysine or cysteine; each of X8, X9, X10, X11 and X12 is independently selected from the group consisting of serine, glycine, glutamine, and glutamate, said amino acids at positions X8 to X12 in the polypeptide of the invention are selected such that a nanoparticle comprising 6 of said polypeptides comprises 6 pores having a size of 3-4 nm, wherein cargo can be loaded into a nanoparticle comprising said polypeptide and released from said nanoparticle without disassembly. In a further preferred embodiment, X1 to X6 are independently of each other lysine or arginine; X7 is selected from arginine, lysine or cysteine; each of X8, X9, X10, X11 and X12 is independently selected from the group consisting of serine, glycine, glutamine, and glutamate, said amino acids at positions X8 to X12 in the polypeptide of the invention are selected such that a nanoparticle comprising 6 of said polypeptides comprises 6 pores having a size of 3-4 nm, wherein cargo can be loaded extracellularly into a nanoparticle comprising said polypeptide and released from said nanoparticle intracellularly, more preferably, into the cytoplasm of a cell, without disassembly. Preferably said cargo are negatively charged macromolecules, more preferably RNA, again more preferably RNA selected from the group consisting of antisense oligonucleotides (ASO), small interference RNA (siRNA), small hairpin RNA (shRNA), micro RNA (miRNA) and anti-miRNA, most preferably siRNA.

In a further preferred embodiment, X1 to X6 are independently of each other lysine or arginine; X7 is selected from arginine, lysine or cysteine; each of X8, X9, X10, X11 and X12 is independently selected from the group consisting of glycine, alanine, leucine, valine; glutamate, aspartate; glutamine, asparagine; serine, threonine, and homoserine; wherein a nanoparticle comprising at least one polypeptide of the invention comprises pores has a size of 3-4 nm, wherein said pore size is selected such that cargo can be loaded into a nanoparticle comprising said polypeptide and released from said nanoparticle without disassembly. In a further preferred embodiment, X1 to X6 are independently of each other lysine or arginine; X7 is selected from arginine, lysine or cysteine, each of X8, X9, X10, X11 and X12 is independently selected from the group consisting of glycine, alanine, leucine, valine; glutamate, aspartate; glutamine, asparagine; serine, threonine, and homoserine; wherein a nanoparticle comprising at least one polypeptide of the invention comprises pores having a size of 3-4 nm, wherein said pore size is selected such that cargo can be loaded extracellularly into a nanoparticle comprising said polypeptide and released from said nanoparticle intracellularly, more preferably, into the cytoplasm of a cell, without disassembly. In a further preferred embodiment, X1 to X6 are independently of each other lysine or arginine; X7 is selected from arginine, lysine or cysteine; each of X8, X9, X10, X11 and X12 is independently selected from the group consisting of serine, glycine, glutamine, and glutamate, wherein a nanoparticle comprising at least one polypeptide of the invention comprises pores having a size of 3-4 nm, wherein said pore size is selected such that cargo can be loaded into a nanoparticle comprising said polypeptide and released from said nanoparticle without disassembly. In a further preferred embodiment, X1 to X6 are independently of each other lysine or arginine; X7 is selected from arginine, lysine or cysteine; each of X8, X9, X10, X11 and X12 is independently selected from the group consisting of serine, glycine, glutamine, and glutamate, wherein a nanoparticle comprising at least one polypeptide of the invention comprises pores having a size of 3-4 nm, wherein said pore size is selected such that cargo can be loaded extracellularly into a nanoparticle comprising said polypeptide and released from said nanoparticle intracellularly, more preferably, into the cytoplasm of a cell, without disassembly. Preferably said cargo are negatively charged macromolecules, more preferably RNA, again more preferably RNA selected from the group consisting of antisense oligonucleotides (ASO), small interference RNA (siRNA), small hairpin RNA (shRNA), micro RNA (miRNA) and anti-miRNA, most preferably siRNA.

In a preferred embodiment, each of X8, X9, X10, X11 and X12 is independently selected from the group consisting of glycine, alanine, leucine, valine, tert-leucine, homoleucine, isoleucine, alloisoleucine 2-aminobutyric acid, diethylalanine, norleucine, norvaline; glutamine, asparagine, beta-hydroxyasparagine, 3-methyl-l-glutamine, (2s,4s)-2,5-diamino-4-hydroxy-5-oxopentanoic acid, n-methyl-asparagine; glutamate, aspartate 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid, 3-methyl-aspartic acid; serine, homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine; and a nanoparticle comprising 6 of said polypeptides of the invention comprises 6 pores with a pore size of 3-4 nm and cargo can be loaded into said nanoparticle and released from said nanoparticle without disassembly. In a preferred embodiment, each of X8, X9, X10, X11 and X12 is independently selected from the group consisting of glycine, alanine, leucine, valine, tert-leucine, homoleucine, isoleucine, alloisoleucine 2-aminobutyric acid, diethylalanine, norleucine, norvaline; glutamine, asparagine, beta-hydroxyasparagine, 3-methyl-l-glutamine, (2s,4s)-2,5-diamino-4-hydroxy-5-oxopentanoic acid, n-methyl-asparagine; glutamate, aspartate 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid, 3-methyl-aspartic acid; serine, homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine, and a nanoparticle comprising 6 of said polypeptides of the invention comprises 6 pores with a pore size of 3-4 nm; and cargo can be loaded extracellularly into said nanoparticle and released from said nanoparticle intracellularly, preferably into the cytoplasm of a cell, both without disassembly. In a further preferred embodiment, each of X8, X9, X10, X11 and X12 is independently selected from the group consisting of glycine, alanine, leucine, valine; glutamate, aspartate; glutamine, asparagine; serine, threonine, and homoserine, and a nanoparticle comprising 6 of said polypeptides of the invention comprises 6 pores with a pore size of 3-4 nm and cargo can be loaded into said nanoparticle and released from said nanoparticle without disassembly. In a further preferred embodiment, each of X8, X9, X10, X11 and X12 is independently selected from the group consisting of serine, glycine, glutamine, and glutamate, and a nanoparticle comprising 6 of said polypeptides of the invention comprises 6 pores with a pore size of 3-4 nm; wherein cargo can be loaded extracellularly into said nanoparticle and released from said nanoparticle intracellularly, preferably into the cytoplasm of a cell, both without disassembly. In a further preferred embodiment, each of X8, X9, X10, X11 and X12 is independently selected from the group consisting of serine, glycine, glutamine, and glutamate, and a nanoparticle comprising 6 of said polypeptides of the invention comprises 6 pores with a pore size of 3-4 nm and cargo can be loaded extracellularly into said nanoparticle and released from said nanoparticle intracellularly, preferably into the cytoplasm of a cell, both without disassembly. Preferably said cargo are negatively charged macromolecules, more preferably RNA, again more preferably RNA selected from the group consisting of antisense oligonucleotides (ASO), small interference RNA (siRNA), small hairpin RNA (shRNA), micro RNA (miRNA) and anti-miRNA, most preferably siRNA.

In a further preferred embodiment, said polypeptide of the invention comprises a histidine tag (His tag) consisting of 3 or more consecutive histidines, wherein said His tag is attached to the C- or N-terminus of said polypeptide, X1 to X6 are independently of each other lysine or arginine; X7 is selected from arginine, lysine or cysteine; each of X8, X9, X10, X11 and X12 is independently selected from the group consisting glycine, alanine, leucine, valine, tert-leucine, homoleucine, isoleucine, alloisoleucine 2-aminobutyric acid, diethylalanine, norleucine, norvaline; glutamine, asparagine, beta-hydroxyasparagine, 3-methyl-l-glutamine, (2s,4s)-2,5-diamino-4-hydroxy-5-oxopentanoic acid, n-methyl-asparagine; glutamate, aspartate 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid, 3-methyl-aspartic acid; serine, homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine, and said amino acids at positions X8 to X12 in the polypeptide of the invention are selected such that a nanoparticle comprising 6 of said polypeptides of the invention comprises 6 pores with a pore size of 3-4 nm and cargo can be loaded into a nanoparticle comprising said polypeptide and released from said nanoparticle without disassembly. In a further preferred embodiment, said polypeptide of the invention comprises a histidine tag (His tag) consisting of 3 or more consecutive histidines, wherein said His tag is attached to the C- or N-terminus of said polypeptide, X1 to X6 are independently of each other lysine or arginine; X7 is selected from arginine, lysine or cysteine; each of X8, X9, X10, X11 and X12 is independently selected from the group consisting of glycine, alanine, leucine, valine, tert-leucine, homoleucine, isoleucine, alloisoleucine 2-aminobutyric acid, diethylalanine, norleucine, norvaline; glutamine, asparagine, beta-hydroxyasparagine, 3-methyl-l-glutamine, (2s,4s)-2,5-diamino-4-hydroxy-5-oxopentanoic acid, n-methyl-asparagine; glutamate, aspartate 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid, 3-methyl-aspartic acid; serine, homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine, and said amino acids at positions X8 to X12 in the polypeptide of the invention are selected such that a nanoparticle comprising 6 of said polypeptides of the invention comprises 6 pores with a pore size of 3-4 nm and cargo can be loaded extracellularly into a nanoparticle comprising said polypeptide and released from said nanoparticle intracellularly, more preferably, into the cytoplasm of a cell, without disassembly. In a further preferred embodiment, said polypeptide of the invention comprises a histidine tag (His tag) consisting of 3 or more consecutive histidines, wherein said His tag is attached to the C- or N-terminus of said polypeptide, X1 to X6 are independently of each other lysine or arginine; X7 is selected from arginine, lysine or cysteine; each of X8, X9, X10, X11 and X12 is independently selected from the group consisting of glycine, alanine, leucine, valine; glutamate, aspartate; glutamine, asparagine; serine, threonine, and homoserine, and said amino acids at positions X8 to X12 in the polypeptide of the invention are selected such that a nanoparticle comprising 6 of said polypeptides of the invention comprises 6 pores with a pore size of 3-4 nm and cargo can be loaded into a nanoparticle comprising said polypeptide and released from said nanoparticle without disassembly. In a further preferred embodiment, said polypeptide of the invention comprises a histidine tag (His tag) consisting of 3 or more consecutive histidines, wherein said His tag is attached to the C- or N-terminus of said polypeptide, X1 to X6 are independently of each other lysine or arginine; X7 is selected from arginine, lysine or cysteine; each of X8, X9, X10, X11 and X12 is independently selected from the group consisting of glycine, alanine, leucine, valine; glutamate, aspartate; glutamine, asparagine; serine, threonine, and homoserine, and said amino acids at positions X8 to X12 in the polypeptide of the invention are selected such that a nanoparticle comprising 6 of said polypeptides of the invention comprises 6 pores with a pore size of 3-4 nm and cargo can be loaded extracellularly into a nanoparticle comprising said polypeptide and released from said nanoparticle intracellularly, more preferably, into the cytoplasm of a cell, without disassembly. In a further preferred embodiment, said polypeptide of the invention comprises a histidine tag (His tag) consisting of 3 or more consecutive histidines, wherein said His tag is attached to the C- or N-terminus of said polypeptide, X1 to X6 are independently of each other lysine or arginine; X7 is selected from arginine, lysine or cysteine; each of X8, X9, X10, X11 and X12 is independently selected from the group consisting of serine, glycine, glutamine, and glutamate, said amino acids at positions X8 to X12 in the polypeptide of the invention are selected such that a nanoparticle comprising 6 of said polypeptides of the invention comprises 6 pores with a pore size of 3-4 nm and cargo can be loaded into a nanoparticle comprising said polypeptide and released from said nanoparticle without disassembly, In a further preferred embodiment, said polypeptide of the invention comprises a histidine tag (His tag) consisting of 3 or more consecutive histidines, wherein said His tag is attached to the C- or N-terminus of said polypeptide, X1 to X6 are independently of each other lysine or arginine; X7 is selected from arginine, lysine or cysteine; each of X8, X9, X10, X11 and X12 is independently selected from the group consisting of serine, glycine, glutamine, and glutamate, said amino acids at positions X8 to X12 in the polypeptide of the invention are selected such that a nanoparticle comprising 6 of said polypeptides of the invention comprises 6 pores with a pore size of 3-4 nm and cargo can be loaded extracellularly into a nanoparticle comprising said polypeptide and released from said nanoparticle intracellularly, more preferably, into the cytoplasm of a cell, without disassembly. Preferably said cargo are negatively charged macromolecules, more preferably RNA, again more preferably RNA selected from the group consisting of antisense oligonucleotides (ASO), small interference RNA (siRNA), small hairpin RNA (shRNA), micro RNA (miRNA) and anti-miRNA, most preferably siRNA. More preferably, said 3 or more consecutive histidines are 3-9 his tags.

In a preferred embodiment, said $X_8$ is glycine or a conservative substitution thereof. Preferably, said conservative substitution of glycine is selected from the group consisting of, alanine, leucine, valine, tert-leucine, homoleucine, isoleucine, alloisoleucine 2-aminobutyric acid, diethylalanine, norleucine, and norvaline. More preferably, said conservative substitution of glycine is selected from the group consisting of, alanine, leucine, valine, tert-leucine, homoleucine, isoleucine, alloisoleucine 2-aminobutyric acid, diethylalanine, norleucine, and norvaline. In a further preferred embodiment, said $X_8$ is selected from the group consisting of glycine, alanine, leucine, and valine. In a preferred embodiment, said $X_8$ is glycine.

In another preferred embodiment, said $X_9$ and $X_{12}$ are independently of each other glutamine or a conservative substitution thereof. Preferably said conservative substitution of glutamine is selected from the group consisting of asparagine, beta-hydroxyasparagine, 3-methyl-l-glutamine, (2s,4s)-2,5-diamino-4-hydroxy-5-oxopentanoic acid, and n-methyl-asparagine. In another preferred embodiment, said $X_9$ and $X_{12}$ are independently of each other glutamine or asparagine.

In another preferred embodiment, said $X_9$ and $X_{12}$ are both glutamine. In another preferred embodiment, said $X_9$ and $X_{12}$ are both asparagine. In another preferred embodiment, said $X_9$ or $X_{12}$ is glutamine. In another preferred embodiment, said $X_9$ is glutamine. In another preferred embodiment, said $X_{12}$ is glutamine.

In another preferred embodiment, said $X_{10}$ is glutamate or a conservative substitution thereof. Preferably, said conservative substitution of glutamate is selected from the group consisting of glutamate, aspartate, 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid and 3-methyl-aspartic acid. In a further preferred embodiment, said $X_{10}$ is glutamate or aspartate. In another further preferred embodiment, said $X_{10}$ is glutamate.

In another preferred embodiment, said $X_{11}$ is selected from the group consisting of serine or a conservative substitution thereof. Preferably said conservative substitution of serine is selected from the group consisting of cysteine, methionine, homocysteine, selenocysteine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, homoserine, 3-hydroxy-l-valine, 4,5-dihydroxy-isoleucine, 6-hydroxy-l-norleucine, s-(2-hydroxyethyl)-l-cysteine, phosphoserine, 4-hydroxy-l-threonine, threonine, and phosphothreonine. More preferably said conservative substitution of serine is selected from the group consisting of cysteine, homocysteine, selenocysteine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, homoserine, 3-hydroxy-l-valine, 4,5-dihydroxy-isoleucine, 6-hydroxy-l-norleucine, s-(2-hydroxyethyl)-l-cysteine, phosphoserine, 4-hydroxy-l-threonine, threonine, and phosphothreonine. Again more preferably said conservative substitution of serine is selected from the group consisting of hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, homoserine, 3-hydroxy-l-valine, 4,5-dihydroxy-isoleucine, 6-hydroxy-l-norleucine, s-(2-hydroxyethyl)-l-cysteine, phosphoserine, 4-hydroxy-l-threonine, threonine, and phosphothreonine. Again more preferably said conservative substitution of serine is selected from the group consisting of homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine.

In a further preferred embodiment, said $X_{11}$ is selected from the group consisting of serine, homoserine, and threonine. In another further preferred embodiment, said $X_{11}$ is serine.

In a preferred embodiment, said $X_8$ is selected from the group consisting of glycine, alanine, leucine, valine, tert-leucine, homoleucine, isoleucine, alloisoleucine 2-aminobutyric acid, diethylalanine, norleucine, and norvaline; $X_9$ and $X_{12}$ are independently of each other selected from the group consisting of glutamine, asparagine, beta-hydroxyasparagine, 3-methyl-l-glutamine, (2s,4s)-2,5-diamino-4-hydroxy-5-oxopentanoic acid, and n-methyl-asparagine; $X_{10}$ is selected from the group consisting of glutamate, aspartate 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid and 3-methyl-aspartic acid; and $X_{11}$ is selected from the group consisting of serine, homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine.

In a further preferred embodiment, said $X_8$ is selected from the group consisting of glycine, alanine, leucine, and valine; $X_9$ and $X_{12}$ are independently of each other glutamine or asparagine; $X_{10}$ is glutamate or aspartate; and $X_{11}$ is selected from the group consisting of serine, threonine, and homoserine.

In a further preferred embodiment, said $X_8$ is glycine, $X_9$ and $X_{12}$ are is glutamine, $X_{10}$ is glutamate and $X_{11}$ is serine.

In a preferred embodiment, each of $X_8$, $X_9$, $X_{10}$, $X_{11}$ and $X_{12}$ is independently selected from the group consisting of glycine, alanine, leucine, valine, tert-leucine, homoleucine, isoleucine, alloisoleucine 2-aminobutyric acid, diethylalanine, norleucine, norvaline; glutamine, asparagine, beta-hydroxyasparagine, 3-methyl-l-glutamine, (2s,4s)-2,5-diamino-4-hydroxy-5-oxopentanoic acid, n-methyl-asparagine; glutamate, aspartate 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid, 3-methyl-aspartic acid; serine, homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine.

In a further preferred embodiment, each of $X_8$, $X_9$, $X_{10}$, $X_{11}$ and $X_{12}$ is independently selected from the group consisting of glycine, alanine, leucine, valine; glutamate, aspartate; glutamine, asparagine; serine, threonine, and homoserine.

In a further preferred embodiment, each of $X_8$, $X_9$, $X_{10}$, $X_{11}$ and $X_{12}$ is independently selected from the group consisting of serine, glycine, glutamine, and glutamate.

In another preferred embodiment, at least three of $X_{1-6}$ are independently of each other lysine or arginine, $X_7$ is selected from arginine, lysine or cysteine, $X_8$ is selected from the group consisting of glycine, alanine, leucine, and valine; $X_9$ and $X_{12}$ are independently of each other glutamine or asparagine; $X_{10}$ is glutamate or aspartate; and $X_{11}$ is selected from the group consisting of serine, threonine, and homoserine. In another preferred embodiment, $X_{1-6}$ are lysine or arginine, $X_7$ is selected from arginine, lysine or cysteine, $X_8$ is selected from the group consisting of glycine, alanine, leucine, and valine; $X_9$ and $X_{12}$ are independently of each other glutamine or asparagine; $X_{10}$ is glutamate or aspartate; and $X_{11}$ is selected from the group consisting of serine, threonine, and homoserine.

In a preferred embodiment, said polypeptide of the invention comprises a histidine tag (His tag) consisting of 3 or more consecutive histidines, wherein said His tag is attached to the C- or N-terminus, preferably the C-terminus of the amino acid sequence I, and wherein in sequence I $X_{1-6}$ are lysine or arginine, $X_7$ is selected from arginine, lysine or cysteine and each of $X_8$, $X_9$, $X_{10}$, $X_{11}$ and $X_{12}$ is independently selected from the group consisting of glycine, alanine, leucine, valine, tert-leucine, homoleucine, isoleucine, alloisoleucine 2-aminobutyric acid, diethylalanine, norleucine, norvaline; glutamine, asparagine, beta-hydroxyasparagine, 3-methyl-l-glutamine, (2s,4s)-2,5-diamino-4-hydroxy-5-oxopentanoic acid, n-methyl-asparagine; glutamate, aspartate 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid, 3-methyl-aspartic acid; serine, homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine.

In a preferred embodiment, said polypeptide of the invention comprises a histidine tag (His tag) consisting of 3-9 consecutive histidines, wherein said His tag is attached to the C- or N-terminus, preferably the C-terminus of the amino acid sequence I, and wherein in sequence I $X_{1-6}$ are lysine or arginine, $X_7$ is selected from arginine, lysine or cysteine and each of $X_8$, $X_9$, $X_{10}$, $X_{11}$ and $X_{12}$ is independently selected from the group consisting of glycine, alanine, leucine, valine, tert-leucine, homoleucine, isoleucine, alloisoleucine 2-aminobutyric acid, diethylalanine, norleucine, norvaline; glutamine, asparagine, beta-hydroxyasparagine, 3-methyl-l-glutamine, (2s,4s)-2,5-diamino-4-hydroxy-5-oxopentanoic acid, n-methyl-asparagine; glutamate, aspartate 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid, 3-methyl-aspartic acid; serine, homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine.

In a preferred embodiment, said polypeptide of the invention comprises a histidine tag (His tag) consisting of 3 or more consecutive histidines, wherein said His tag is attached to the C- or N-terminus, preferably the C-terminus of the amino acid sequence I, and wherein in sequence I at least three of $X_{1-6}$ are independently of each other lysine or arginine, $X_7$ is selected from arginine, lysine or cysteine, $X_8$ is selected from the group consisting of glycine, alanine, leucine, and valine; $X_9$ and $X_{12}$ are independently of each other glutamine or asparagine; $X_{10}$ is glutamate or aspartate; and $X_{11}$ is selected from the group consisting of serine, threonine, and homoserine. In a preferred embodiment, said polypeptide of the invention comprises a histidine tag (His tag) consisting of 3 to 9 consecutive histidines, wherein said His tag is attached to the C- or N-terminus, preferably the C-terminus of the amino acid sequence I, and wherein in sequence I at least three of $X_{1-6}$ are independently of each other lysine or arginine, $X_7$ is selected from arginine, lysine or cysteine, $X_8$ is selected from the group consisting of glycine, alanine, leucine, and valine; $X_9$ and $X_{12}$ are independently of each other glutamine or asparagine; $X_{10}$ is glutamate or aspartate; and $X_{11}$ is selected from the group consisting of serine, threonine, and homoserine.

In a preferred embodiment, said polypeptide of the invention comprises a histidine tag (His tag) consisting of 3 or more consecutive histidines, wherein said His tag is attached to the C- or N-terminus, preferably the C-terminus of the amino acid sequence I, and wherein in sequence I $X_{1-6}$ are independently lysine or arginine, $X_7$ is selected from arginine, lysine or cysteine, $X_8$ is selected from the group consisting of glycine, alanine, leucine, and valine; $X_9$ and $X_{12}$ are independently of each other glutamine or asparagine; $X_{10}$ is glutamate or aspartate; and $X_{11}$ is selected from the group consisting of serine, threonine, and homoserine. In a preferred embodiment, said polypeptide of the invention comprises a histidine tag (His tag) consisting of 3 to 9 consecutive histidines, wherein said His tag is attached to the C- or N-terminus, preferably the C-terminus of the amino acid sequence I, and wherein in sequence I $X_{1-6}$ are independently lysine or arginine, $X_7$ is selected from arginine, lysine or cysteine, $X_8$ is selected from the group consisting of glycine, alanine, leucine, and valine; $X_9$ and $X_{12}$ are independently of each other glutamine or asparagine; $X_{10}$ is glutamate or aspartate; and $X_{11}$ is selected from the group consisting of serine, threonine, and homoserine. In another preferred embodiment, at least three of $X_{1-6}$ are independently of each other lysine or arginine, $X_8$ is glycine, $X_9$ and $X_{12}$ are independently of each other glutamine, $X_{10}$ is glutamate and $X_{11}$ is serine. In another preferred embodiment, $X_{1-6}$ are lysine or arginine, $X_7$ is selected from arginine, lysine or cysteine and $X_8$ is glycine, $X_9$ and $X_{12}$ are independently of each other glutamine, $X_{10}$ is glutamate and $X_{11}$ is serine. In another preferred embodiment, $X_{1-6}$ are lysine or arginine, $X_7$ is selected from arginine, lysine or cysteine and $X_8$ is glycine, $X_9$ and $X_{12}$ are independently of each other is glutamine, $X_{10}$ is glutamate and $X_{11}$ is serine.

In one embodiment, at least 3 of said $X_{1-6}$ are independently of each other lysine or arginine, said $X_7$ is selected from arginine, lysine or cysteine, $X_8$ is glycine, $X_9$ and $X_{12}$ are independently of each other glutamine, $X_{10}$ is glutamate and $X_{11}$ is serine, and said polypeptide comprises a polyhistidine which is an amino acid sequence comprising two or more consecutively linked histidines, preferably said polyhistidine is a histidine (His) tag, more preferably a His6 tag. A histidine tag is defined herein as an amino acid sequence consisting of two or more consecutively linked histidines (His tag). A His6 tag (His6) is defined herein as an amino acid sequence consisting of 6 consecutively linked histidines.

In another preferred embodiment, $X_1$ to $X_6$ are independently of each other lysine or arginine, $X_7$ is selected from arginine, lysine or cysteine, $X_8$ is glycine, $X_9$ and $X_{12}$ are independently of each other glutamine, $X_{10}$ is glutamate and $X_{11}$ is serine and said polypeptide comprises a polyhistidine which is an amino acid sequence comprising two or more consecutively linked histidines, preferably said polyhistidine is a histidine (His) tag, more preferably a His6 tag.

In a preferred embodiment, said polypeptide of the invention comprises a histidine tag (His tag) consisting of 3 or more consecutive histidines, wherein said His tag is attached to the C- or N-terminus, preferably the C-terminus of the amino acid sequence I, and wherein in sequence I $X_{1-6}$ are lysine or arginine, $X_7$ is selected from arginine, lysine or cysteine and $X_8$ is glycine, $X_9$ and $X_{12}$ are independently of each other glutamine, $X_{10}$ is glutamate and $X_{11}$ is serine. In a preferred embodiment, said nanoparticle or said complex comprising said polypeptide of the invention is capable of endosomal escape. In a preferred embodiment, said polypeptide of the invention comprises a histidine tag (His tag) consisting of 3 or more consecutive histidines, wherein said nanoparticle or said complex comprising said polypeptide of the invention is capable of endosomal escape. In a preferred embodiment, said polypeptide of the invention comprises a histidine tag (His tag) consisting of 3 or more consecutive histidines, wherein said His tag is attached to the C- or N-terminus, and said nanoparticle or said complex comprising said polypeptide of the invention is capable of endosomal escape. In a preferred embodiment, said polypeptide of the invention comprises a histidine tag (His tag) consisting of 3 or more consecutive histidines, wherein said His tag is attached to the C- or N-terminus, preferably the C-terminus of the amino acid sequence I; in sequence I X1-6 are lysine or arginine, X7 is selected from arginine, lysine or cysteine and X8 is glycine, X9 and X12 are independently of each other glutamine, X10 is glutamate and X11 is serine; and said nanoparticle or said complex of the invention comprising said polypeptide of the invention is capable of endosomal escape.

When the polypeptide of the invention forms a nanoparticle by self-assembly, amino acids $X_{13}$ to $X_{29}$ are exposed to the external surface of the nanoparticle and are therefore most prone to tolerate mutations while still keeping ability to self-assemble into a cage-like nanoparticle.

Thus, in a preferred embodiment, amino acids $X_{13}$ to $X_{29}$ exposed to the external surface of the nanoparticle are any amino acid.

In a preferred embodiment, $X_{13}$, $X_{17}$ and $X_{19}$ are independently of each other serine or a conservative substitution thereof. Preferably said conservative substitution of serine is selected from the group consisting of cysteine, methionine, homocysteine, selenocysteine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, homoserine, 3-hydroxy-l-valine, 4,5-dihydroxy-isoleucine, 6-hydroxy-l-norleucine, s-(2-hydroxyethyl)-l-cysteine, phosphoserine, 4-hydroxy-l-threonine, threonine, and phosphothreonine. More preferably said conservative substitution of serine is selected from the group consisting of cysteine, homocysteine, selenocysteine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, homoserine, 3-hydroxy-l-valine, 4,5-dihydroxy-isoleucine, 6-hydroxy-l-norleucine, s-(2-hydroxyethyl)-l-cysteine, phosphoserine, 4-hydroxy-l-threonine, threonine, and phosphothreonine. Again more preferably said conservative substitution of serine is selected from the group consisting of hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, homoserine, 3-hydroxy-l-valine, 4,5-dihydroxy-isoleucine, 6-hydroxy-l-norleucine, s-(2-hydroxyethyl)-l-cysteine, phosphoserine, 4-hydroxy-l-threonine, threonine, and phosphothreonine. Again more preferably said conservative substitution of serine is selected from the group consisting of homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine.

In another preferred embodiment, $X_{13}$, $X_{17}$ and $X_{19}$, are independently of each other selected from the group consisting of serine, homoserine, and threonine. In another preferred embodiment, $X_{13}$, $X_{17}$ and $X_{19}$, are independently of each other serine.

In another preferred embodiment, $X_{14}$, $X_{16}$ and $X_{24}$ are independently of each other asparagine or a conservative substitution thereof. Preferably, said conservative substitution of asparagine is selected from the group consisting of glutamine, beta-hydroxyasparagine, 3-methyl-l-glutamine, (2s,4s)-2,5-diamino-4-hydroxy-5-oxopentanoic acid, and n-methyl-asparagine In another preferred embodiment, $X_{14}$, $X_{16}$ and $X_{24}$ are independently of each other asparagine. In another preferred embodiment, $X_{14}$, $X_{16}$ and $X_{24}$ are independently of each other asparagine or glutamine.

In another preferred embodiment, $X_{15}$, $X_{20}$ $X_{26}$ and $X_{28}$ are independently of each other aspartate, glutamate or a conservative substitution thereof. Preferably said conservative substitution of aspartate or glutamate is selected from the group consisting of 2s,4r-4-methylglutamate, (3s)-3-methyl-l-glutamic acid, (3r)-3-methyl-l-glutamic acid, 5-o- methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid and 3-methyl-aspartic acid.

In another preferred embodiment, $X_{15}$ and $X_{20}$ are independently of each other aspartate. In another preferred embodiment, $X_{26}$ and $X_{28}$ are independently of each other glutamate. In another preferred embodiment, $X_{15}$, $X_{20}$ $X_{26}$ and $X_{28}$ are independently of each other aspartate or glutamate. In another preferred embodiment, $X_{15}$, $X_{20}$ $X_{26}$ and $X_{28}$ are independently of each other selected from the group consisting of glutamate, aspartate, 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid and 3-methyl-aspartic acid.

In another preferred embodiment, $X_{18}$ and $X_{29}$ are independently of each other leucine or a conservative substitution thereof. Preferably said conservative substitution of leucine is selected from the group consisting of glycine, alanine, valine, tert-leucine, homoleucine, isoleucine, alloisoleucine 2-aminobutyric acid, diethylalanine, norleucine, and norvaline.

In another preferred embodiment, $X_{18}$ and $X_{29}$ are independently of each other leucine. In a preferred embodiment, said $X_{18}$ and $X_{29}$ are independently of each other selected from the group consisting of glycine, alanine, leucine, and valine. In a preferred embodiment, said $X_{18}$, and $X_{29}$ are independently of each other selected from the group consisting of glycine, alanine, leucine, valine, tert-leucine, homoleucine, isoleucine, alloisoleucine 2-aminobutyric acid, diethylalanine, norleucine, and norvaline.

In another preferred embodiment, $X_{21}$, $X_{22}$, $X_{23}$, $X_{25}$ and $X_{27}$ are independently of each other a positively charged amino acid.

In another preferred embodiment, $X_{21}$, $X_{22}$, $X_{23}$, $X_{25}$ and $X_{27}$ are independently of each other arginine, lysine or a conservative substitution thereof. Preferably said conservative substitution of arginine or leucine is selected from the group consisting of histidine, 5-methyl-arginine, c-gamma-hydroxy arginine, 2-amino-4-guanidinobutryric acid, 2-amino-3-guanidinopropionic acid, canavanine, homoarginine, diaminobutyric acid, 2,3-diaminopropanoic acid, (2s)-2,8-diaminooctanoic acid, ornithine and thialysine. More preferably said conservative substitution of arginine or leucine is selected from the group consisting of 5-methyl-arginine, c-gamma-hydroxy arginine, 2-amino-4-guanidinobutryric acid, 2-amino-3-guanidinopropionic acid, canavanine, homoarginine, diaminobutyric acid, 2,3-diaminopropanoic acid, (2s)-2,8-diaminooctanoic acid, ornithine and thialysine.

In another preferred embodiment, $X_{21}$, $X_{22}$, $X_{23}$, $X_{25}$ and $X_{27}$ are independently of each other histidine, arginine or lysine. In another preferred embodiment, $X_{21}$, $X_{22}$, $X_{23}$, $X_{25}$ and $X_{27}$ are independently of each other arginine or lysine. In another preferred embodiment, $X_{21}$, $X_{22}$, $X_{23}$, $X_{25}$ and $X_{27}$ are independently of each other is arginine. In another preferred embodiment, $X_{21}$, $X_{22}$, $X_{23}$, $X_{25}$ and $X_{27}$ are independently of each other $_6$ is lysine.

In another preferred embodiment, $X_{21}$, $X_{22}$, $X_{25}$ and $X_{27}$ are independently of each other arginine. In another preferred embodiment, $X_{23}$ is lysine. In another preferred embodiment, $X_{21}$, $X_{22}$, $X_{23}$, $X_{25}$ and $X_{27}$ are independently of each other selected from the group consisting of arginine, 5-methyl-arginine, c-gamma-hydroxy arginine, 2-amino-4-guanidinobutryric acid, 2-amino-3-guanidinopropionic acid, canavanine, homoarginine, lysine, diaminobutyric acid, 2,3-diaminopropanoic acid, (2s)-2,8-diaminooctanoic acid, ornithine and thialysine.

In another preferred embodiment, $X_{13}$, $X_{17}$ and $X_{19}$, are independently of each other serine; $X_{14}$, $X_{16}$ and $X_{24}$ are independently of each other asparagine; $X_{15}$ and $X_{20}$ are independently of each other aspartate; $X_{18}$ and $X_{29}$ are independently of each other leucine; $X_{26}$ and $X_{28}$ are independently of each other glutamate; $X_{21}$, $X_{22}$, $X_{25}$ and $X_{27}$ are independently of each other arginine; and $X_{23}$ is lysine.

In another preferred embodiment, $X_{13}$, $X_{17}$ and $X_{19}$, are independently of each other selected from the group consisting of serine, homoserine, and threonine; $X_{14}$, $X_{16}$ and $X_{24}$ are independently of each other asparagine or glutamine; $X_{15}$, $X_{20}$ $X_{26}$ and $X_{28}$ are independently of each other aspartate or glutamate; said $X_{18}$ and $X_{29}$ are independently of each other selected from the group consisting of glycine, alanine, leucine, and valine; $X_{21}$, $X_{22}$, $X_{23}$, $X_{25}$ and $X_{27}$ are independently of each other arginine or lysine.

In another preferred embodiment, $X_{13}$, $X_{17}$, and $X_{19}$, are independently of each other selected from the group consisting of serine, homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine;

$X_{14}$, $X_{16}$, and $X_{24}$ are independently of each other selected from the group consisting of glutamine, asparagine, beta-hydroxyasparagine, 3-methyl-l-glutamine, (2s,4s)-2,5-diamino-4-hydroxy-5-oxopentanoic acid, and n-methyl-asparagine;

$X_{15}$, $X_{20}$ $X_{26}$ and $X_{28}$ are independently of each other selected from the group consisting of glutamate, aspartate, 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid and 3-methyl-aspartic acid;

$X_{18}$, and $X_{29}$ are independently of each other selected from the group consisting of glycine, alanine, leucine, valine, tert-leucine, homoleucine, isoleucine, alloisoleucine 2-aminobutyric acid, diethylalanine, norleucine, and norvaline; and $X_{21}$, $X_{22}$, $X_{23}$, $X_{25}$ and $X_{27}$ are independently of each other selected from the group consisting of arginine, 5-methyl-arginine, c-gamma-hydroxy arginine, 2-amino-4-guanidinobutryric acid, 2-amino-3-guanidinopropionic acid, canavanine, homoarginine, lysine, diaminobutyric acid, 2,3-diaminopropanoic acid, (2s)-2,8-diaminooctanoic acid, ornithine and thialysine.

In another preferred embodiment, $X_8$ is glycine or a conservative substitution thereof, wherein preferably said conservative substitution of glycine is selected from the group consisting of alanine, leucine, valine, tert-leucine, homoleucine, isoleucine, alloisoleucine 2-aminobutyric acid, diethylalanine, norleucine, and norvaline;

$X_9$ and $X_{12}$ are independently of each other glutamine or a conservative substitution thereof, wherein preferably said conservative substitution of glutamine is selected from the group consisting of asparagine, beta-hydroxyasparagine, 3-methyl-l-glutamine, (2s,4s)-2,5-diamino-4-hydroxy-5-oxopentanoic acid, and n-methyl-asparagine;

$X_{10}$ is glutamate or a conservative substitution thereof, wherein preferably said conservative substitution of glutamate is selected from the group consisting of aspartate 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid, and 3-methyl-aspartic acid; and $X_{11}$ is serine or a conservative substitution thereof, wherein preferably said conservative substitution of serine is selected from the group consisting of homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine;

more preferably $X_8$ is glycine, $X_9$ and $X_{12}$ are independently of each other glutamine or asparagine, $X_{10}$ is glutamate or aspartate, and $X_{11}$ is serine.

In another preferred embodiment, $X_{13}$, $X_{17}$, and $X_{19}$ are independently of each other serine or a conservative substitution thereof, wherein preferably said conservative substitution of serine is selected from the group consisting of homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine;

$X_{14}$, $X_{16}$, and $X_{24}$ are independently of each other asparagine, glutamine or a conservative substitution thereof, wherein preferably said conservative substitution of asparagine or glutamine is selected from the group consisting of beta-hydroxyasparagine, 3-methyl-l-glutamine, (2s,4s)-2,5-diamino-4-hydroxy-5-oxopentanoic acid, and n-methyl-asparagine;

$X_{15}$, $X_{20}$ $X_{26}$ and $X_{28}$ are independently of each other aspartate, glutamate or a conservative substitution thereof, wherein preferably said conservative substitution of aspartate or glutamate is selected from the group consisting of 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid and 3-methyl-aspartic acid;

$X_{18}$ and $X_{29}$ are independently of each other leucine or a conservative substitution thereof, wherein preferably said conservative substitution of leucine is selected from the group consisting of glycine, alanine, valine, tert-leucine, homoleucine, isoleucine, alloisoleucine 2-aminobutyric acid, diethylalanine, norleucine, and norvaline; and $X_{21}$, $X_{22}$, $X_{23}$, $X_{25}$ and $X_{27}$ are independently of each other arginine, lysine or a conservative substitution thereof, wherein preferably said conservative substitution of arginine or leucine is selected from the group consisting of histidine, 5-methyl-arginine, c-gamma-hydroxy arginine, 2-amino-4-guanidinobutryric acid, 2-amino-3-guanidinopropionic acid, canavanine, homoarginine, diaminobutyric acid, 2,3-diaminopropanoic acid, (2s)-2,8-diaminooctanoic acid, ornithine and thialysine.

In another preferred embodiment, said positively charged amino acid of said at least 3 of $X_1$ to $X_6$ is independently of each other selected from the group consisting of arginine, 5-methyl-arginine, c-gamma-hydroxy arginine, 2-amino-4-guanidinobutyric acid, 2-amino-3-guanidinopropionic acid, canavanine, homoarginine, lysine, diaminobutyric acid, 2,3-diaminopropanoic acid, (2s)-2,8-diaminooctanoic acid, ornithine, and thialysine;

$X_7$ is cysteine, a conservative substitution thereof or a positively charged amino acid; preferably $X_7$ is selected from the group consisting of homocysteine, cysteine, selenocysteine, arginine, 5-methyl-arginine, c-gamma-hydroxy arginine, 2-amino-4-guanidinobutyric acid, 2-amino-3-guanidinopropionic acid, canavanine, homoarginine, lysine, diaminobutyric acid, 2,3-diaminopropanoic acid, (2s)-2,8-diaminooctanoic acid, ornithine, thialysine and serine;

$X_8$ is glycine or a conservative substitution thereof selected from the group consisting of, alanine, leucine, valine, tert-leucine, homoleucine, isoleucine, alloisoleucine 2-aminobutyric acid, diethylalanine, norleucine, and norvaline;

$X_9$ and $X_{12}$ are independently of each other glutamine or a conservative substitution thereof selected from the group consisting of asparagine, beta-hydroxyasparagine, 3-methyl-l-glutamine, (2s,4s)-2,5-diamino-4-hydroxy-5-oxopentanoic acid, and n-methyl-asparagine;

$X_{10}$ is glutamate or a conservative substitution thereof selected from the group consisting of aspartate 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid, and 3-methyl-aspartic acid; and $X_{11}$ is serine or a conservative substitution thereof selected from the group consisting of homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine;

$X_{13}$, $X_{17}$, and $X_{19}$, are independently of each other selected from the group consisting of serine, homoserine, threonine, 4-hydroxy-l-threonine, 6-hydroxy-l-norleucine, 4,5-dihydroxy-isoleucine, 3-hydroxy-l-valine, hydroxynorvaline, 2-amino-5-hydroxypentanoic acid, allo-threonine, 3,3-dihydroxy-alanine, 4-hydroxy-L-isoleucine, (2s,3r)-2-amino-3-hydroxy-4-methylpentanoic acid, beta-hydroxyleucine, and allo-threonine;

$X_{14}$, $X_{16}$, and $X_{24}$ are independently of each other selected from the group consisting of glutamine, asparagine, beta-hydroxyasparagine, 3-methyl-l-glutamine, (2s,4s)-2,5-diamino-4-hydroxy-5-oxopentanoic acid, and n-methyl-asparagine;

$X_{15}$, $X_{20}$ $X_{26}$ and $X_{28}$ are independently of each other selected from the group consisting of glutamate, aspartate, 2s,4r-4-methylglutamate, (3s)-3-methyl-l-glutamic acid, (3r)-3-methyl-l-glutamic acid, 5-o-methyl-glutamic acid, 4-hydroxy-glutamic-acid, 6-carboxylysine, beta-hydroxyaspartic acid, 2-amino-propanedioic acid, 3,3-dimethyl aspartic acid, 2-aminoadipic acid and 3-methyl-aspartic acid;

$X_{18}$, and $X_{29}$ are independently of each other selected from the group consisting of glycine, alanine, leucine, valine, tert-leucine, homoleucine, isoleucine, alloisoleucine 2-aminobutyric acid, diethylalanine, norleucine, and norvaline; and $X_{21}$, $X_{22}$, $X_{23}$, $X_{25}$ and $X_{27}$ are independently of each other selected from the group consisting of arginine, 5-methyl-arginine, c-gamma-hydroxy arginine, 2-amino-4-guanidinobutryric acid, 2-amino-3-guanidinopropionic acid, canavanine, homoarginine, lysine, diaminobutyric acid, 2,3-diaminopropanoic acid, (2s)-2,8-diaminooctanoic acid, ornithine and thialysine.

In another preferred embodiment, said positively charged amino acid of said at least 3 of $X_1$ to $X_6$ is independently of each other arginine or lysine, $X_7$ is selected from the group consisting of homocysteine, cysteine, arginine, and lysine, $X_8$ is selected from the group consisting of glycine, alanine, leucine, and valine, $X_9$ and $X_{12}$ are independently of each other glutamine or asparagine, $X_{10}$ is glutamate or aspartate, $X_{11}$, $X_{13}$, $X_{17}$, and $X_{19}$ are independently of each other selected from the group consisting of serine, threonine, and homoserine, $X_{14}$, $X_{16}$, and $X_{24}$ are independently of each other asparagine or glutamine, $X_{15}$, $X_{20}$ $X_{26}$ and $X_{28}$ are independently of each other aspartate or glutamate, $X_{18}$ and $X_{29}$ are independently of each other selected from the group consisting of leucine, glycine, alanine, and valine, and $X_{21}$, $X_{22}$, $X_{23}$, $X_{25}$ and $X_{27}$ are independently of each other arginine or lysine.

In another preferred embodiment, said positively charged amino acid of said at least 3 of $X_1$ to $X_6$ is independently of each other arginine or lysine, $X_7$ is selected from the group consisting of homocysteine, cysteine, arginine, and lysine, $X_8$ is glycine, $X_9$ and $X_{12}$ are independently of each other glutamine or asparagine, $X_{10}$ is glutamate or aspartate, $X_{11}$ is serine, $X_{13}$, $X_{17}$, and $X_{19}$ are independently of each other serine, $X_{14}$, $X_{16}$, and $X_{24}$ are independently of each other asparagine, $X_{15}$, $X_{20}$ $X_{26}$ and $X_{28}$ are independently of each other aspartate or glutamate, $X_{18}$ and $X_{29}$ are independently of each other leucine, and $X_{21}$, $X_{22}$, $X_{23}$, $X_{25}$ and $X_{27}$ are independently of each other arginine or lysine.

In another preferred embodiment, at least three of $X_{1-6}$ are independently of each other lysine or arginine, $X_7$ is selected from arginine, lysine or cysteine, $X_8$ is selected from the group consisting of glycine, alanine, leucine, and valine; $X_9$ and $X_{12}$ are independently of each other glutamine or asparagine; $X_{10}$ is glutamate or aspartate; and $X_{11}$ is selected from the group consisting of serine, threonine, and homoserine; $X_{18}$ and $X_{29}$ are independently of each other leucine; $X_{15}$ and $X_{20}$ are independently of each other aspartate; $X_{26}$ and $X_{28}$ are independently of each other glutamate; $X_{14}$, $X_{16}$ and $X_{24}$ are independently of each other asparagine; $X_{13}$, $X_{17}$ and $X_{19}$, are independently of each other serine; $X_{21}$, $X_{22}$, $X_{25}$ and $X_{27}$ are independently of each other arginine; and $X_{23}$ is lysine.

In another preferred embodiment, at least three of $X_{1-6}$ are independently of each other lysine or arginine, $X_7$ is selected from arginine, lysine or cysteine, $X_8$ is selected from the group consisting of glycine, alanine, leucine, and valine; $X_9$ and $X_{12}$ are independently of each other glutamine or asparagine; $X_{10}$ is glutamate or aspartate; and $X_{11}$ is selected from the group consisting of serine, threonine, and homoserine; $X_{13}$, $X_{17}$ and $X_{19}$, are independently of each other selected from the group consisting of serine, homoserine, and threonine; $X_{14}$, $X_{16}$ and $X_{24}$ are independently of each other asparagine or glutamine; $X_{15}$, $X_{20}$ $X_{26}$ and $X_{28}$ are independently of each other aspartate or glutamate; said $X_{18}$ and $X_{29}$ are independently of each other selected from the group consisting of glycine, alanine, leucine, and valine; $X_{21}$, $X_{22}$, $X_{23}$, $X_{25}$ and $X_{27}$ are independently of each other arginine or lysine.

In another preferred embodiment, $X_{1-6}$ are independently of each other lysine or arginine, $X_7$ is selected from arginine, lysine or cysteine, $X_8$ is selected from the group consisting of glycine, alanine, leucine, and valine; $X_9$ and $X_{12}$ are independently of each other glutamine or asparagine; $X_{10}$ is glutamate or aspartate; and $X_{11}$ is selected from the group consisting of serine, threonine, and homoserine; $X_{13}$, $X_{17}$ and $X_{19}$, are independently of each other selected from the group consisting of serine, homoserine, and threonine; $X_{14}$, $X_{16}$ and $X_{24}$ are independently of each other asparagine or glutamine; $X_{15}$, $X_{20}$ $X_{26}$ and $X_{28}$ are independently of each other aspartate or glutamate; said $X_{18}$ and $X_{29}$ are independently of each other selected from the group consisting of glycine, alanine, leucine, and valine; $X_{21}$, $X_{22}$, $X_{23}$, $X_{25}$ and $X_{27}$ are independently of each other arginine or lysine.

In another preferred embodiment, $X_{1-6}$ are independently of each other lysine or arginine, $X_7$ is selected from arginine, lysine or cysteine, $X_8$ is selected from the group consisting of glycine, alanine, leucine, and valine; $X_9$ and $X_{12}$ are independently of each other glutamine or asparagine; $X_{10}$ is glutamate or aspartate; and $X_{11}$ is selected from the group consisting of serine, threonine, and homoserine; $X_{13}$, $X_{17}$ and $X_{19}$, are independently of each other serine; $X_{14}$, $X_{16}$ and $X_{24}$ are independently of each other asparagine; $X_{15}$ and $X_{20}$ are independently of each other aspartate; $X_{18}$ and $X_{29}$ are independently of each other leucine; $X_{26}$ and $X_{28}$ are independently of each other glutamate; $X_{21}$, $X_{22}$, $X_{25}$ and $X_{27}$ are independently of each other arginine; and $X_{23}$ is lysine.

In another preferred embodiment, at least three or at least four of $X_{1-6}$ are independently of each other lysine or arginine, $X_7$ is selected from arginine, lysine or cysteine, $X_8$ is selected from the group consisting of glycine, alanine, leucine, and valine; $X_9$ and $X_{12}$ are independently of each other glutamine or asparagine; $X_{10}$ is glutamate or aspartate; and $X_{11}$ is selected from the group consisting of serine, threonine, and homoserine; $X_{13}$, $X_{17}$ and $X_{19}$, are independently of each other selected from the group consisting of serine, homoserine, and threonine; $X_{14}$, $X_{16}$ and $X_{24}$ are independently of each other asparagine or glutamine; $X_{15}$, $X_{20}$ $X_{26}$ and $X_{28}$ are independently of each other aspartate or glutamate; said $X_{18}$ and $X_{29}$ are independently of each other selected from the group consisting of glycine, alanine, leucine, and valine; $X_{21}$, $X_{22}$, $X_{23}$, $X_{25}$ and $X_{27}$ are independently of each other arginine or lysine, and said polypeptide comprises a polyhistidine which is an amino acid sequence comprising two or more consecutively linked histidines, preferably said polyhistidine is a histidine (His) tag, more preferably a His6 tag.

In another preferred embodiment, $X_{1-6}$ are independently of each other lysine or arginine, $X_7$ is selected from arginine, lysine or cysteine, $X_8$ is selected from the group consisting of glycine, alanine, leucine, and valine; $X_9$ and $X_{12}$ are independently of each other glutamine or asparagine; $X_{10}$ is glutamate or aspartate; and $X_{11}$ is selected from the group consisting of serine, threonine, and homoserine; $X_{13}$, $X_{17}$ and $X_{19}$, are independently of each other selected from the group consisting of serine, homoserine, and threonine; $X_{14}$, $X_{16}$ and $X_{24}$ are independently of each other asparagine or glutamine; $X_{15}$, $X_{20}$ $X_{26}$ and $X_{28}$ are independently of each other aspartate or glutamate; said $X_{18}$ and $X_{29}$ are independently of each other selected from the group consisting of glycine, alanine, leucine, and valine; $X_{21}$, $X_{22}$, $X_{23}$, $X_{25}$ and $X_{27}$ are independently of each other arginine or lysine, and said polypeptide comprises a polyhistidine which is an amino acid sequence comprising two or more consecutively linked histidines, preferably said polyhistidine is a histidine (His) tag, more preferably a His6 tag.

In a preferred embodiment, said amino acid sequence I is a sequence selected from the group consisting of SEQ ID NO: 2 to 5 and SEQ ID NO: 10 to 16. In a preferred embodiment, said polypeptide of the invention consists of a sequence selected from the group consisting of SEQ ID NO: 2 to 5 and SEQ ID NO: 10 to 16.

In a preferred embodiment, said amino acid sequence I is a sequence selected from the group consisting of SEQ ID NO: 2 to 5 and SEQ ID NO: 10 to 16, 37 and 38. In a preferred embodiment, said polypeptide of the invention consists of a sequence selected from the group consisting of SEQ ID NO: 2 to 5 and SEQ ID NO: 10 to 16, 37 and 38.

In a preferred embodiment, said amino acid sequence I is SEQ ID NO: 2. In a preferred embodiment, said amino acid sequence I is SEQ ID NO: 3. In another preferred embodiment, said amino acid sequence I is SEQ ID NO: 4. In another preferred embodiment, said amino acid sequence I is SEQ ID NO: 5. In another preferred embodiment, said amino acid sequence I is SEQ ID NO: 10. In another preferred embodiment, said amino acid sequence I is SEQ ID NO: 11. In another preferred embodiment, said amino acid sequence I is SEQ ID NO: 12. In another preferred embodiment, said amino acid sequence I is SEQ ID NO: 13. In a preferred embodiment, said amino acid sequence I is SEQ ID NO: 14. In another preferred embodiment, said amino acid sequence I is SEQ ID NO: 15. In another preferred embodiment, said amino acid sequence I is SEQ ID NO: 16. In another preferred embodiment, said amino acid sequence I is SEQ ID NO: 37. In another preferred embodiment, said amino acid sequence I is SEQ ID NO: 38.

In a preferred embodiment, said polypeptide of the invention consists of a sequence selected from the group consisting of SEQ ID NO: 2. In another preferred embodiment, said polypeptide of the invention consists of a sequence selected from the group consisting of SEQ ID NO: 3. In another preferred embodiment, said polypeptide of the invention consists of a sequence selected from the group consisting of SEQ ID NO: 4. In another preferred embodiment, said polypeptide of the invention consists of a sequence selected from the group consisting of SEQ ID NO: 5. In another preferred embodiment, said polypeptide of the invention consists of a sequence selected from the group consisting of SEQ ID NO: 10. In another preferred embodiment, said polypeptide of the invention consists of a sequence selected from the group consisting of SEQ ID NO: 11. In another preferred embodiment, said polypeptide of the invention consists of a sequence selected from the group consisting of SEQ ID NO: 12. In another preferred embodiment, said polypeptide of the invention consists of a sequence selected from the group consisting of SEQ ID NO: 13. In another preferred embodiment, said polypeptide of the invention consists of a sequence selected from the group consisting of SEQ ID NO: 14. In another preferred embodiment, said polypeptide of the invention consists of a sequence selected from the group consisting of SEQ ID NO: 15. In another preferred embodiment, said polypeptide of the invention consists of a sequence selected from the group consisting of SEQ ID NO: 16. In another preferred embodiment, said polypeptide of the invention consists of a sequence selected from the group consisting of SEQ ID NO: 37. In another preferred embodiment, said polypeptide of the invention consists of a sequence selected from the group consisting of SEQ ID NO: 38. In a preferred embodiment, said polypeptide of the invention consists of a sequence selected from the group consisting of SEQ ID NO: 3, wherein said polypeptide of the invention comprises a histidine tag (His tag) consisting of 3 or more consecutive histidines, wherein said His tag is attached to the C- or N-terminus of the amino acid sequence I. In another preferred embodiment, said polypeptide of the invention consists of a sequence selected from the group consisting of SEQ ID NO: 3, wherein said polypeptide of the invention comprises a histidine tag (His tag) consisting of 3-9 consecutive histidines, wherein said His tag is attached to the C- or N-terminus, preferably the C-terminus of the amino acid sequence I. In a preferred embodiment, said polypeptide of the invention comprises an additional tag, i.e. a peptide or non-peptide tag, preferably a peptide tag (i.e. a functional amino acid sequence). In a preferred embodiment, said tag is located at the C- or N-terminal end of the polypeptide of the invention.

In a preferred embodiment, said tag is a non-peptide tag, preferably polyethylene glycol (PEG). Preferably, said PEG is coupled via the amino acid serine or cysteine to said amino acid sequence 1. PEG coupled to the polypeptide of the invention increases stability and immunogenicity In another preferred embodiment, said tag is selected from the group consisting of polyhistidine, His tag (i.e. an amino acid sequence consisting of two or more consecutively linked histidines), degradation tag, targeting tag, cell penetration tag, and endosomal escape tag.

In a preferred embodiment, said polypeptide of the invention comprises a polyhistidine. In a preferred embodiment, said polyhistidine is an amino acid sequence comprising two or more histidines. In another preferred embodiment, said polyhistidine is an amino acid sequence comprising two or more consecutively linked histidines. In another preferred embodiment, said polyhistidine is an amino acid sequence comprising 3 or more consecutively linked histidines. In another preferred embodiment, said polyhistidine is an amino acid sequence comprising 3 to 9 consecutively linked histidines. In another preferred embodiment, said polyhistidine is an amino acid sequence comprising 3, 6 or 9 consecutively linked histidines.

In a preferred embodiment, said polypeptide of the invention comprises a histidine tag (His tag) consisting of consecutively linked histidines (His tag). Preferably, said His tag consists of 3 or more consecutive histidines. Preferably, said His tag consists of 3 to 9 consecutive histidines. Preferably, said His tag consists of 3, 6 or 9 consecutive histidines. Preferably, said His tag consists of 3 consecutive histidines. Preferably, said His tag consists of 9 consecutive histidines. Preferably, said His tag consists of 6 consecutive histidines (i.e. His6 tag). In a preferred embodiment, said His tag is attached to the C- or N-terminus, preferably the C-terminus, of the amino acid sequence I. In a preferred embodiment, said His6 tag is attached to the C- or N-terminus, preferably the C-terminus, of the amino acid sequence I. Preferably, said His tag consists of 3 or more consecutive histidines and is attached to the C- or N-terminus, preferably the C-terminus, of the amino acid sequence I. Preferably, said His tag consists of 3 to 9 consecutive histidines, and said His tag is attached to the C- or N-terminus of the amino acid sequence I. Preferably, said His tag consists of 3 to 9 consecutive histidines, and said His tag is attached to the C-terminus of the amino acid sequence I. Preferably, said His tag consists of 3, 6 or 9 consecutive histidines and is attached to the C- or N-terminus, preferably the C-terminus, of the amino acid sequence I. Preferably, said His tag consists of 3 consecutive histidines (i.e. His3 tag), and said His tag is attached to the C- or N-terminus, preferably the C-terminus, of the amino acid sequence I. Preferably, said His tag consists of 9 consecutive histidines (i.e. His9 tag), and said His tag is attached to the C- or N-terminus, preferably the C-terminus, of the amino acid sequence I.

In a preferred embodiment, said His tag, preferably said His6 tag comprises halogenated, preferably fluorinated histidines. In a preferred embodiment, said His tag comprises a fluorophore. In a preferred embodiment, said polypeptide of the invention comprises a fluorophore.

In a preferred embodiment, said polypeptide of the invention comprises a degradation tag. Preferably said degradation tag is functional in mammalian cells. In a preferred embodiment, said degradation tag is a C-terminal sequence of ornithine decarboxylase (cODC), preferably of SEQ ID NO: 17, or (poly)ubiquitin comprising or consisting of at least two consecutively linked ubiquitins. In another preferred embodiment, said degradation tag consists of cODC of SEQ ID NO: 17 (EFPPEVEEQDDGTLPMSCAQESGMDRHPAACASARINV). In another preferred embodiment, said degradation tag comprises at least two consecutively linked ubiquitins. More preferably, said degradation tag consists of at least two consecutively linked ubiquitins.

In a preferred embodiment, the polypeptide of the invention comprises a targeting tag which is a peptide targeting tag or a non-peptide targeting tag. Preferred peptide targeting tags are mentioned in Zhao et al. (Tumor-targeting Peptides: Ligands for Molecular Imaging and Therapy, Anticancer Agents Med Chem. 2018, 18(1):74-86). Said targeting tag preferably binds to a cancer target and is thus mentioned herein as cancer targeting tag. Said cancer target includes receptors with an increased level of expression in certain tumor cells and tumor antigens. In a preferred embodiment, said cancer targeting tag is a peptide ligand, peptidomimetic or antibody that binds to a cancer target. Preferably, said cancer targeting tag is folic acid. For example, folic acid can be conjugated to the polypeptide of the invention via a peptide bond.

In a further embodiment, the polypeptide of the invention comprises an endosomal escape peptide or cell-penetrating peptide (CPP). The endosomal escape peptide is for example a dimerized disulfide-linked TAT or a thiol group. The term "cell-penetrating peptide" or CPP, as used herein, refers to a group of peptides with the ability to penetrate the plasma membrane for delivery of cargo into cells. Preferably, said CPP used in the polypeptide of the invention is a hydrophilic or cationic peptide. In another embodiment, said CPP is selected from an amphiphilic, anionic or hydrophobic peptide. A database of more than 1,600 CPPs is described by Agrawal et al. (Agrawal P, Bhalla S, Usmani S S, Singh S, CHaudhary K, Raghava GPS, et al. CPPsite 2.0: a repository of experimentally validated cell-penetrating peptides. Nucl Acids Res. 2016, 44:D1098-D103).

In a preferred embodiment, said additional tag included in the polypeptide of the invention is connected via a releasable linkage, such as a photo-cleavable linkage, or via reversible coupling.

Said polypeptide of the invention is capable of self-assembling into a nanoparticle, preferably a cage-like nanoparticle. Further, also said mutein of SEQ ID NO: 1 is capable of self-assembling into a nanoparticle, preferably a cage-like nanoparticle.

In a further aspect, the invention relates to a nucleic acid encoding the polypeptide according to the invention.

In a further aspect, the invention relates to a nanoparticle comprising at least one polypeptide according to the invention.

In a preferred embodiment, each of said at least one polypeptide of the nanoparticle of the invention comprises a histidine tag consisting of at least 3 consecutively linked histidines, wherein each of said histidine tags are attached to the C- or N-terminus, preferably the C-terminus of said at least one polypeptide.

In a preferred embodiment, each of said at least one polypeptide of the nanoparticle of the invention comprises a histidine tag consisting of at least 3 consecutively linked histidines, wherein each of said histidine tags are attached to the C- or N-terminus, preferably the C-terminus of said at least one polypeptide, wherein said nanoparticle is loadable and unloadable with cargo, without disassembly of the nanoparticle. In a preferred embodiment, each of said at least one polypeptide of the nanoparticle of the invention comprises a histidine tag consisting of at least 3 consecutively linked histidines, wherein each of said histidine tags are attached to the C- or N-terminus, preferably the C-terminus of said at least one polypeptide, wherein said nanoparticle is loadable and unloadable with cargo, in vivo and in vitro, without disassembly of the nanoparticle. In a preferred embodiment, each of said at least one polypeptide of the nanoparticle of the invention comprises a histidine tag consisting of at least 3 consecutively linked histidines, wherein each of said histidine tags are attached to the C- or N-terminus, preferably the C-terminus of said at least one polypeptide, wherein said nanoparticle is loadable with cargo in vitro and unloadable with cargo in vivo, without disassembly of the nanoparticle. In a preferred embodiment, each of said at least one polypeptide of the nanoparticle of the invention comprises a histidine tag consisting of at least 3 consecutively linked histidines, wherein each of said histidine tags are attached to the C- or N-terminus, preferably the C-terminus of said at least one polypeptide, wherein said nanoparticle is capable of endosomal escape and loadable and unloadable with cargo, without disassembly of the nanoparticle. Preferably said cargo are negatively charged macromolecules, more preferably RNA, again more preferably RNA selected from the group consisting of antisense oligonucleotides (ASO), small interference RNA (siRNA), small hairpin RNA (shRNA), micro RNA (miRNA) and anti-miRNA, most preferably siRNA.

In a preferred embodiment, said polypeptide of the invention comprised by the nanoparticle of the invention consists of a sequence selected from the group consisting of SEQ ID NO: 3, wherein said polypeptide of the invention comprises a histidine tag (His tag) consisting of 3 or more consecutive histidines, wherein said His tag is attached to the C- or N-terminus, preferably the C-terminus of the amino acid sequence I, and wherein said nanoparticle is loadable and unloadable with cargo without disassembly of said nanoparticle. In a preferred embodiment, said polypeptide of the invention comprised by the nanoparticle of the invention consists of a sequence selected from the group consisting of SEQ ID NO: 3, wherein said polypeptide of the invention comprises a histidine tag (His tag) consisting of 3 or more consecutive histidines, wherein said His tag is attached to the C- or N-terminus, preferably the C-terminus of the amino acid sequence I, and wherein said nanoparticle is loadable with cargo in vitro and unloadable with cargo in vivo, without disassembly of said nanoparticle. In a preferred embodiment, said nanoparticle of the invention is included in a composition, preferably in a pharmaceutical composition comprising a pharmaceutically acceptable carrier.

The term "nanoparticle" as used herein refers to a particle in the nanometer size range (i.e. from about 1 nm to about 1000 nanometers) that is capable of encapsulating molecules. Said nanoparticle has a regular arrayed surface of linked molecules that self-assemble to form the nanoparticle.

Said nanoparticle of the invention has a positively charged cavity. Thus, it is capable of encapsulating cargo, such as oligonucleotides (ONs). Further, said nanoparticles can enter a cell and conditionally release the cargo intracellularly, preferably into the cytoplasm. Thus, the nanoparticle can for example be used to deliver ONs intracellularly in order to control gene expression via antisense ONs, for vaccination or immune system stimulation.

In a preferred embodiment, the nanoparticle of the invention is capable of encapsulating cargo, preferably said cargo are negatively charged macromolecules, more preferably RNA, again more preferably RNA selected from the group consisting of antisense oligonucleotides (ASO), small interference RNA (siRNA), small hairpin RNA (shRNA), micro RNA (miRNA) and anti-miRNA, most preferably siRNA, and capable to deliver said encapsulated cargo to a cell. Preferably, said cargo is delivered intracellularly. In a preferred embodiment, the nanoparticle of the invention is capable of encapsulating cargo, preferably said cargo are negatively charged macromolecules, more preferably RNA, again more preferably RNA selected from the group consisting of antisense oligonucleotides (ASO), small interference RNA (siRNA), small hairpin RNA (shRNA), micro RNA (miRNA) and anti-miRNA, most preferably siRNA, and capable to release said encapsulated cargo intracellularly. In a preferred embodiment, the nanoparticle of the invention is capable of encapsulating cargo extracellularly, capable of entering a cell with said encapsulated cargo, and capable of releasing said cargo intracellularly. In a preferred embodiment, the nanoparticle of the invention is capable of encapsulating cargo extracellularly, capable of entering a cell with said encapsulated cargo, and capable of releasing said cargo into the cytoplasm of said cell. In a preferred embodiment, the nanoparticle of the invention is capable of encapsulating cargo in vitro, and capable of releasing said cargo in vivo, preferably intracellularly, more preferably into the cytoplasm of a cell. In a preferred embodiment, the nanoparticle of the invention is capable of encapsulating cargo in vitro, capable of entering a cell with said encapsulated cargo, and capable of releasing said cargo in vivo, preferably intracellularly, more preferably into the cytoplasm of said cell. Preferably said cargo are negatively charged macromolecules, more preferably RNA, again more preferably RNA selected from the group consisting of antisense oligonucleotides (ASO), small interference RNA (siRNA), small hairpin RNA (shRNA), micro RNA (miRNA) and anti-miRNA, most preferably siRNA.

In a preferred embodiment, said nanoparticle of the invention is loadable and unloadable with cargo, without disassembly of said nanoparticle. In a preferred embodiment, said nanoparticle of the invention is extracellularly loadable with cargo and intracellularly unloadable without disassembly of said nanoparticle. In a preferred embodiment, said nanoparticle of the invention allows loading and unloading of cargo without disassembly of said nanoparticle. In a preferred embodiment, said nanoparticle of the invention allows extracellularly loading of cargo and intracellularly unloading of said cargo, without disassembly of said nanoparticle. Preferably said cargo are negatively charged macromolecules, more preferably RNA, again more preferably RNA selected from the group consisting of antisense oligonucleotides (ASO), small interference RNA (siRNA), small hairpin RNA (shRNA), micro RNA (miRNA) and anti-miRNA, most preferably siRNA.

In a preferred embodiment, said nanoparticle of the invention is loadable with cargo in vivo and in vitro, and unloadable in vivo and in vitro, without disassembly of said nanoparticle. In a preferred embodiment, said nanoparticle of the invention is loadable in vitro and unloadable in vivo, without disassembly of said nanoparticle.

In a further embodiment, said nanoparticle comprises at least one subunit, wherein said subunit comprises at least one polypeptide according to the invention. The term "subunit" as used herein refers to building blocks that assemble and form the nanoparticle of the invention. The subunit comprises at least one polypeptide of the invention. Preferably, said subunit comprises three polypeptides of the invention, preferably exactly three peptides of the invention. More preferably said subunit consists of three polypeptides of the invention. In another preferred embodiment, said subunit comprises three identical peptides of the invention, preferably exactly three identical peptides of the invention. More preferably said subunit consists of three identical polypeptides of the invention. In another more preferred embodiment, said subunit comprises or more preferably consists of three polypeptides of the invention, and said subunit has C3 symmetry.

In a preferred embodiment, the nanoparticle comprises exactly 24 polypeptides of the invention. In a preferred embodiment, the nanoparticle comprises exactly 8 subunits. In another preferred embodiment, the nanoparticle has an octahedral geometry (octahedral point group symmetry). In a preferred embodiment of the invention, the nanoparticle has a quaternary structure of multiple subunits, preferably of 8 subunits each comprising 3 polypeptides of the invention.

In a preferred embodiment, said nanoparticle of the invention comprises a central cavity (also mentioned herein as cavity, internal cavity or lumen). Said nanoparticles comprising a central cavity are mentioned herein also as "cage-like nanoparticle" or "cage". In a preferred embodiment said cage-like nanoparticle comprises (i) an exterior scaffold and (ii) the central cavity. Preferably, said exterior scaffold surrounds, i.e. is assembled around said central cavity. Said cavity can be empty or it can include cargo.

The nanoparticle of the invention has a positively charged interior. The cage-like nanoparticle of the invention is positively charged on the cavity surface. Said positive charges stem from multiple positively charged amino acids, such as arginines or lysines. Thus, the nanoparticles of the invention have a very strong affinity to encapsulate negatively charged macromolecules.

In a preferred embodiment, said cavity has a diameter from about 6.5 nm to about 8 nm. In a preferred embodiment, said cage-like nanoparticle has a porous structure, i.e. said nanoparticle includes pores. Preferably, the exterior scaffold of the cage-like nanoparticle includes pores that are connected to the cavity of said nanoparticle. A pore is defined herein as an opening or gap in the nanoparticle and in the exterior scaffold of the nanoparticle, respectively.

Loading (or encapsulation) and unloading (or release) of cargo in the nanoparticle works via the pores. The terms loading or encapsulation relates to any uptake of cargo into the nanoparticle including the cavity, scaffold and porous structure of the nanoparticle. The term unloading (or release) relates to liberation or dis-/replacement of the cargo by another cargo, either in part or completely, preferably completely. Preferably, unloading takes place under competing conditions, i.e. conditions wherein cargo to be unloaded and another cargo to be loaded are competing with each other.

In a preferred embodiment, said cage-like nanoparticle comprises six pores. Preferably, said cage-like nanoparticle comprises six pores, which are connected to the cavity. Preferably, said exterior scaffold includes six pores, which are connected to the cavity of the nanoparticle.

In another preferred embodiment, said pores have a diameter from about 3 nm to about 4 nm. In another preferred embodiment, said nanoparticle includes 6 pores having a diameter of 3-4 nm In another preferred embodiment, said nanoparticle has an external diameter up to about 50 nm. In a very preferred embodiment, said nanoparticle has an external diameter of about 13 nm.

In another further preferred embodiment, the nanoparticle includes 6 pores having a diameter of about 3-4 nm, said internal cavity has a diameter of about 8 nm, and said external diameter of the nanoparticle is about 13 nm.

In a preferred embodiment, said nanoparticle of the invention is capable of encapsulation and release of cargo without disassembly of the nanoparticle, preferably said cargo are negatively charged macromolecules, more preferably RNA, again more preferably RNA selected from the group consisting of antisense oligonucleotides (ASO), small interference RNA (siRNA), small hairpin RNA (shRNA), micro RNA (miRNA) and anti-miRNA.

Due to the multimeric nature of the nanoparticle, modification of the polypeptide of the invention with a functional moiety, for example a peptide tag or a chemical group such as PEG provides polyvalent display of this functional moiety on the nanoparticle surface.

In a preferred embodiment, the nanoparticle, especially the cage-like nanoparticle comprises a functional moiety (herein referred to also as moiety). Preferably, said moiety is located on the external surface of the nanoparticle. More preferably, said additional moiety is attached to the nanoparticle, preferably to the external surface of the nanoparticle.

In a preferred embodiment, said moiety is attached to the nanoparticle or its external surface by covalent or non-covalent bonds, preferably by covalent bonds. Covalent bonds include and preferably are peptide bonds or a disulfide bond.

In another preferred embodiment, said moiety attached to the nanoparticle is the peptide tag or non-peptide tag of the polypeptide of the invention.

In another preferred embodiment, said moiety is selected from the group consisting of a polyhistidine, His tag (i.e. an amino acid sequence consisting of two or more consecutively linked histidines), degradation tag, targeting tag, cell penetration tag, and endosomal escape tag.

Said targeting tag preferably binds to a cancer target, i.e. said targeting tag is a cancer targeting tag. Said cancer target includes receptors with an increased level of expression in/on certain tumor cells and tumor antigens. In a preferred embodiment, said cancer targeting tag is a peptide ligand, peptidomimetic or antibody that binds to a cancer target. Said cancer targeting tag is preferably folic acid.

In a preferred embodiment, the nanoparticle of the invention displays at least 72 histidyl residues on the external surface of the nanoparticle. In a further preferred embodiment, the nanoparticle of the invention displays at least 72-216 histidyl residues on the external surface of the nanoparticle.

In a preferred embodiment, the nanoparticle of the invention displays at least 72 histidyl residues on the external surface of the nanoparticle, and wherein said histidyl residues are attached to the C- or N-terminus, preferably the C-terminus of the amino acid sequence I, wherein said nanoparticle can be loaded and unloaded with cargo without disassembly in vivo as well as in vitro. In a preferred embodiment, the nanoparticle of the invention displays at least 72 histidyl residues on the external surface of the nanoparticle, and wherein said histidyl residues are attached to the C- or N-terminus, preferably the C-terminus of the amino acid sequence I. In a further preferred embodiment, the nanoparticle of the invention displays at least 72-216 histidyl residues on the external surface of the nanoparticle, and wherein said histidyl residues are attached to the C- or N-terminus, preferably the C-terminus of the amino acid sequence I.

In a preferred embodiment, the nanoparticle of the invention displays at least 96 histidyl residues, preferably 144 histidyl residues on the external surface of the nanoparticle. In a further preferred embodiment, the nanoparticle of the invention displays on its external surface 3 to 50, preferably 24 histidine-rich amino acid sequences, wherein each of said histidine-rich amino acid sequences is independently attached to the N- or C-terminal of the polypeptide of the invention and each of said histidine-rich amino acid sequences includes at least 5, preferably 6 histidyl residues. Preferably, said histidine-rich amino acid sequence has a length of 30 amino acids or less, preferably 25 amino acids or less, more preferably 20 amino acids or less, again more preferably 15 amino acids or less, again more preferably 10 or less, again more preferably 5 or 6 amino acids.

In a further preferred embodiment, the nanoparticle of the invention displays on its external surface at least 72, preferably at least 96, more preferably at least 120, again more preferably at least 144 histidyl residues. In a further preferred embodiment, the nanoparticle of the invention displays on its external surface about 144 histidyl residues.

In more preferred embodiment, the nanoparticle of the invention displays 24 His tags on its external surface, wherein each of said His tags consist of 3 or more consecutively linked histidines. In a further preferred embodiment, the nanoparticle of the invention displays 24 His tags on its external surface, wherein each of said His tags consist of 3-9 consecutively linked histidines. In more preferred embodiment, the nanoparticle of the invention displays 24 His tags on its external surface, wherein each of said His tags consist of 3 or more consecutively linked histidines, and wherein said His tag is attached to the C- or N-terminus, preferably the C-terminus of the amino acid sequence I. In a further preferred embodiment, the nanoparticle of the invention displays 24 His tags on its external surface, wherein each of said His tags consist of 3-9 consecutively linked histidines, and wherein said His tag is attached to the C- or N-terminus, preferably the C-terminus of the amino acid sequence I.

In another preferred embodiment, the nanoparticle of the invention displays 3 to 50, preferably 24 His6 tags on its external surface, wherein each of said His6 tags consist of 6 consecutively linked histidines. In a preferred embodiment, the nanoparticle of the invention displays on its external surface 3 to 50, preferably 24 amino acid sequences comprising a His6 tag (which is defined herein as a sequence consisting of 6 consecutively linked histidines, i.e. homo-hexa-histidine), wherein each of said His6 tag comprising sequences is independently attached to the N- or C-terminal of the polypeptide of the invention. Preferably, said His6 tag comprising sequence has a length of 30 amino acids or less, preferably 25 or less, more preferably 20 or less, again more preferably 15 or less, again more preferably 10 or less. In a preferred embodiment, the nanoparticle of the invention displays on its external surface 3 to 50, preferably 24 His6 tags, wherein each of said His6 tags is independently attached to the N- or C-terminal of the polypeptide of the invention.

These histidine-rich peptides are crucial for the delivery to the cytoplasm of the target cells, likely due to endosomal escape properties. It has been reported that histidine residues can play an important role in endosomal escape in synthetic peptides and some viruses. However, the use of a multimeric protein assembly to present multiple copies of a functional histidine-rich peptide has not been demonstrated and represents a novel approach to cytoplasmic delivery of protein nanoparticles.

In a preferred embodiment, the nanoparticle of the invention is modified genetically (for direct fusion of peptides) or chemically after production.

The nanoparticle of the invention shows only negligible cytotoxicity. In vitro cytotoxicity was measured in HeLa cells over 24 hours using WST-8 to quantify dehydrogenase activity (see below Materials & Methods, Cytotoxicity). The nanoparticle of the invention reduced viability to about 95% at maximum. Reduction of viability was between about 0% and about 5% at concentrations from 12 µg/mL to 193 µg/mL protein (400 nM cage). In comparison, Lipofectamine 2000 reduced cell viability to about 35-45% at 19-fold lower concentrations by mass (10 µg/mL) under the same assay conditions.

In a further aspect, the invention relates to a complex comprising the nanoparticle of the invention and one or more cargo molecules.

In a preferred embodiment, said complex comprises a cage-like nanoparticle of the invention and one or more cargo molecules encapsulated in the cavity of the cage-like nanoparticle.

In a preferred embodiment, said complex of the invention is capable of inducing an immune response in an organism. Preferably said organism is an animal, more preferably a mammalian, again more preferably a mouse or human, most preferably a human.

Said cargo molecule of the complex of the invention is preferably a macromolecule. In a further preferred embodiment, said macromolecule is negatively charged.

The term "negatively charged" as used herein includes and preferably refers to a molecule that has a negatively charged group. More preferably, said negatively charged molecule has a negatively charged group at neutral or physiological pH.

Due to the highly positively charged interior of the nanoparticle of the invention, stemming from the arginine residues, the nanoparticle has a strong affinity to encapsulate negatively charged macromolecules, such as ONs. The treatment of cells with the complex of the invention leads to intracellular delivery of the complex and release of its functional negatively charged macromolecules. Thus, the complex of the invention is capable of entering cells, endosomal escape and intracellular release of the negatively charged macromolecules. For example, the complex comprising ONs provided selective knockdown of a desired gene due to cytoplasmic delivery and release of the ONs.

The complex of the invention is further capable of entering cells, and it is also capable of releasing the negatively charged macromolecules, such as ONs, intracellularly, preferably to the cytoplasm. Thus, the complex of the invention is conditionally stable with negatively charged macromolecules, such as ONs. The highly positively charged interior of the cage provides a strong driving force for the encapsulation of negatively charged macromolecules, such as ONs, affording complexes that are stable for weeks at room temperature in standard buffers.

Encapsulation is reversible in the presence of high concentrations of competing guest molecules, while the complexes of the invention are stable extracellularly. In the presence of high concentrations of negatively charged competitors, e.g. nucleic acids, as found in the cytoplasm of a cell, the negatively charged macromolecules, such as ONs, are gradually released and able to carry out its biological function. This concept of competitor-induced, location-specific release of negatively charged macromolecules, such as ONs, is unique and has the potentially to be modified by altering the number and location of arginine residues in the protein cage interior. Thus, in a preferred embodiment the nanoparticle of the invention is capable of reversibly encapsulating and releasing cargo. In a further preferred embodiment, the nanoparticle of the invention is capable of reversibly encapsulating and releasing cargo without disassembly of the nanoparticle. In a further preferred embodiment, the nanoparticle of the invention is capable of encapsulating and releasing cargo without disassembly of the nanoparticle. Said cargo is preferably negatively charged macromolecules, more preferably RNA, again more preferably RNA selected from the group consisting of antisense oligonucleotides (ASO), small interference RNA (siRNA), small hairpin RNA (shRNA), micro RNA (miRNA) and anti-miRNA.

In a further embodiment, the nanoparticle of the invention is capable of extracellularly encapsulating cargo, preferably said cargo are negatively charged macromolecules, more preferably RNA, again more preferably RNA selected from the group consisting of antisense oligonucleotides (ASO), small interference RNA (siRNA), small hairpin RNA (shRNA), micro RNA (miRNA) and anti-miRNA, and said nanoparticle encapsulating said cargo is capable of releasing said cargo intracellularly.

In a preferred embodiment, each of said one or more negatively charged macromolecules has a diameter of about 3.5 nm or less. In a further preferred embodiment, each of said one or more negatively charged macromolecules has a diameter of about 2 nm or less. In a preferred embodiment, each of said one or more negatively charged macromolecules has a diameter of about 2 nm and a length of about 8 nm. Preferably, said macromolecules are a straight chain of monomers, preferably with a diameter of about 2 nm and a length of about 8 nm.

In a preferred embodiment, said negatively charged macromolecule is a nucleic acid or a polypeptide.

In another preferred embodiment, said cargo molecule is an oligonucleotide (ON).

The term "oligonucleotide" as used herein refers to a compound comprising 2 or more nucleotides linked to each other each by a nucleosidic linkage. Oligonucleotides are polyribonucleotides or polydeoxribonucleotides or mixtures thereof and are preferably selected from single or double stranded (a) unmodified, i.e. naturally occurring RNA or DNA, (b) modified RNA or DNA or (c) RNA or DNA mimetics, such as locked nucleic acid (LNA) or peptide nucleic acid (PNA). Oligonucleotides are preferably selected from the group consisting of (a) single- and double-stranded DNA, (b) DNA that is a mixture of single- and double-stranded regions, (c) single- and double-stranded RNA, (d) RNA that is mixture of single- and double-stranded regions, and (e) hybrid molecules comprising DNA and RNA that are single-stranded or double-stranded or a mixture of single- and double-stranded regions. In a further preferred embodiment, In a further embodiment oligonucleotides are triple-stranded regions and higher-ordered structures comprising RNA or DNA or both RNA and DNA. In further embodiments, oligonucleotide are synthetic, genomic or recombinant. In one embodiment, oligonucleotide refers to (a) DNA or RNA containing at least one modified nucleotide or at least one nucleotide analogue, or (b) to DNA or RNA with backbones modified for stability or for other reasons.

The terms "modified RNA" or "modified DNA", as used herein, refers to an oligonucleotide as defined above and having at least one modified internucleoside linkage and/or at least one sugar modification and/or at least one base modification compared to a naturally occurring ribonucleotide- or deoxyribonucleotide-based oligonucleotide. A modified internucleoside linkage indicates the presence of a modified version of the phosphodiester which does not occur naturally in RNA and DNA. Examples of internucleoside linkage modifications, which are known to the skilled person in the art and which are compatible with the present invention, are and include in particular, phosphoramidate, phosphorodiamidate, phosphorothioate, phosphorodithioate, H-phosphonate, methyl phosphonate and methyl phosphonothioate. A sugar modification indicates the presence of a modified version of the ribosyl moiety as naturally occurring in RNA and DNA (i.e. the furanosyl moiety), such as bicyclic sugars, tetrahydropyrans, morpholinos, 2'-modified sugars, 3'-modified sugars, 4'-modified sugars, 5'-modified sugars, and 4'-substituted sugars. Examples of suitable sugar modifications are known to the skilled person in the art and include, but are not limited to, 2'-O-modified RNA nucleotide residues, such as 2'-O-alkyl or 2'-O-(substituted)alkyl, e.g. 2'-O-methyl, 2'-O-(2-cyanoethyl), 2'-O-(2-methoxy)ethyl (2'-MOE), 2'-O-(2-thiomethyl)ethyl; 2'-O-(haloalkoxy)methyl, e.g. 2'-O-(2-chloroethoxy)methyl (MCEM), 2'-O-(2,2-dichloroethoxy)methyl (DCEM); 2'-O-alkoxycarbonyl, e.g. 2'-O-[2-(methoxycarbonyl)ethyl] (MOCE), 2'-O-[2-(N-methylcarbamoyl)ethyl] (MCE), 2'-O-[2-(N,N-dimethylcarbamoyl)ethyl] (DMCE), in particular a 2'-O-methyl modification or a 2'-O-(2-methoxy)ethyl (2'-MOE). Another important modification includes bridged or bicyclic nucleic acid (BNA) modified sugar moieties, such as found in e.g. locked nucleic acid (LNA), xylo-LNA, alpha-L-LNA, beta-D-LNA, cEt (2'-O,4'-C constrained ethyl) LNA, cMOEt (2'-O,4'-C constrained methoxyethyl) LNA, ethylene-bridged nucleic acid (ENA), hexitol nucleic acid (HNA), fluorinated HNA (F-HNA), pyranosyl-RNA (p-RNA), 3'-deoxypyranosyl-DNA (p-DNA); or other modified sugar moieties, such as morpholino (PMO), cationic morpholino (PMOPlus) or PMO-X, all known to the skilled person in the art. The term "base modification", as used herein refers to the modification of a naturally occurring base in RNA and/or DNA (i.e. pyrimidine or purine base). A base modification is known to the skilled person in the art and includes, but is not limited to, a modified version of the natural purine and pyrimidine bases (e.g. adenine, uracil, guanine, cytosine, and thymine), such as hypoxanthine, pseudouracil, pseudothymine, 2-thiopyrimidine (e.g. 2-thiouracil, 2-thiothymine), 2,6-diaminopurine, 5-substituted pyrimidine (e.g. 5-halouracil, 5-methyluracil, 5-methylcytosine) 7-deazaguanine, 7-deazaadenine, 7-aza-2,6-diaminopurine, 8-aza-7-deazaguanine, 8-aza-7-deazaadenine, or 8-aza-7-deaza-2,6-diaminopurine. It is also encompassed by the invention that said oligonucleotide comprises more than one, the same or different, internucleoside linkage modification, sugar modification and/or base modification. Thus, oligonucleotides, as referred to in this invention, can consist of any combinations of the nucleotides and their modifications described above.

More preferably said one or more negatively charged macromolecules are one or more oligoribonucleotide selected from the group consisting of antisense oligonucleotides (ASO), small interference (siRNA), small hairpin RNA (shRNA), micro RNA (miRNA) and anti-miRNA. Further preferred are oligonucleotides capable of stimulating IFN-alpha production in cells, preferably in dendritic cells.

In a preferred embodiment, said one or more negatively charged macromolecules is one or more ON, wherein the total number of nucleotides of said one or more ON is about 300 or less. In another preferred embodiment, the total number of nucleotides of said one or more ON is from about 10 to about 300, preferably from about 20 to about 300, more preferably from about 40 to about 300, again more preferably from about 50 to about 300, again more preferably from about 100 to about 300, again more preferably from about 200 to about 300.

In another preferred embodiment, the total number of nucleotides of said one or more ON is from about 10 to about 300, preferably from about 10 to about 200, more preferably from about 10 to about 50, again more preferably from about 10 to about 40, again more preferably from about 10 to about 30.

In another preferred embodiment, the total number of nucleotides of said one or more ON is from about 10 to about 300, preferably from about 20 to about 200, more preferably from about 40 to about 100.

In a preferred embodiment, the total number of nucleotides of said one or more ON is about 300 or less and said ON is RNA, preferably ssRNA.

In a further preferred embodiment, said one or more ON are single stranded ON (ssON), preferably ssRNA or ssDNA, wherein said ssON jointly have a length of about 40 nts or more, preferably about 40 to about 300 nts, more preferably about 40 to about 200 nts, again more preferably about 40 to about 100 nts, again more preferably about 40 nts. In another preferred embodiment, said one or more ON are double stranded ON (dsON), preferably dsRNA or dsDNA, wherein said dsON jointly have a length of about 40 bps or more, preferably about 40 to about 300 bps, more preferably about 40 to about 200 bps, again more preferably about 40 to about 100 bps, again more preferably about 40 bps.

In a preferred embodiment, said one or more macromolecules are one or more oligonucleotides, wherein said one or more oligonucleotides are encapsulated in said nanoparticle and not accessible to DNAse hydrolysis. Therefore, in the preferred meaning, the term "encapsulated" indicates that the one or more oligonucleotides, in an encapsulated state, are not accessible to DNAse hydrolysis. More preferably, the term "encapsulated" indicates that the one or more oligonucleotides, in an encapsulated state, are not accessible to DNAse hydrolysis, wherein the DNAse is DNAse I or Benzonase. Again more preferably, the term "encapsulated" indicates that the one or more oligonucleotides, in an encapsulated state, are not accessible to Benzonase hydrolysis.

Said negatively charged macromolecule is encapsulated within the nanoparticle preferably by non-covalent bonds. Said non-covalent bonds are preferably electrostatic bonds.

Other optional reagents can be included within the nanoparticle, such as an adjuvant.

Figure 2:
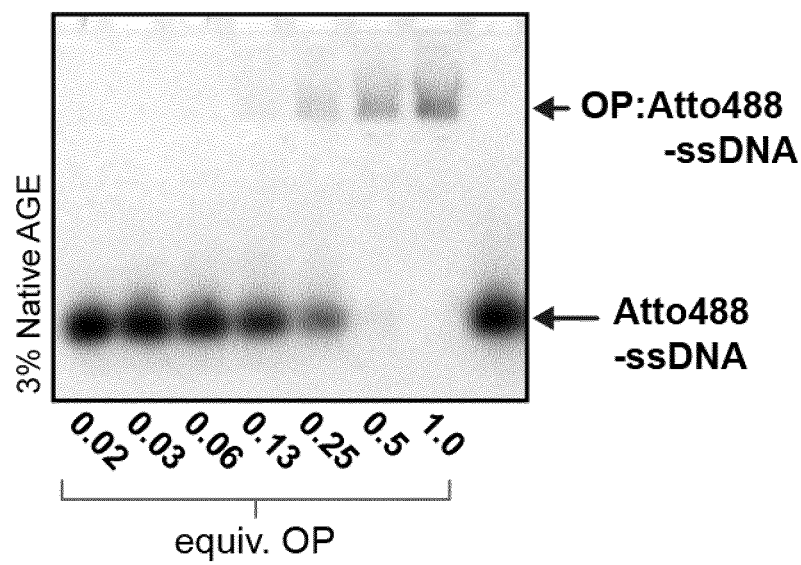
FIG. 2: (a) Electrophoretic mobility shift assay of Atto488-labeled ssDNA with OP, visualized by Atto488 fluorescence. (b) Absorbance spectra of SEC-purified OP:nucleic acid complexes. (c) Plot of $k_{obs}$ values, from fluorescence quenching of Atto488-ssDNA cargo upon addition of OP, vs. [OP] to determine $k_{on}$. (d) Plot of fluorescence recovery of Atto488-ssDNA released from OP cages induced by addition of unlabeled competitor DNA.
Figure 2:
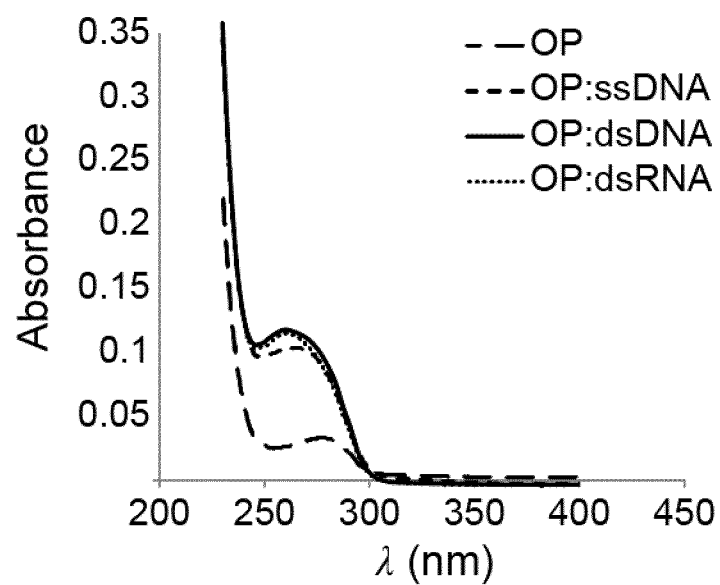
Figure 2:
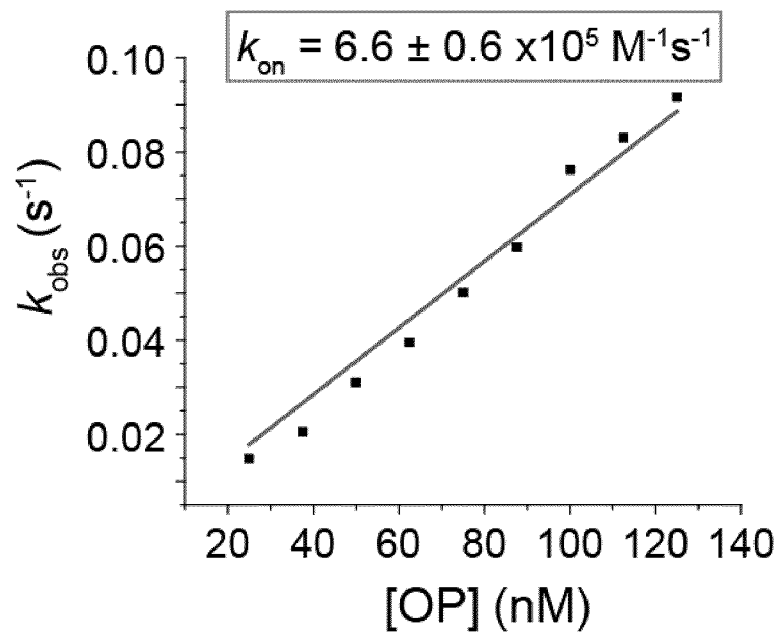
Figure 2:
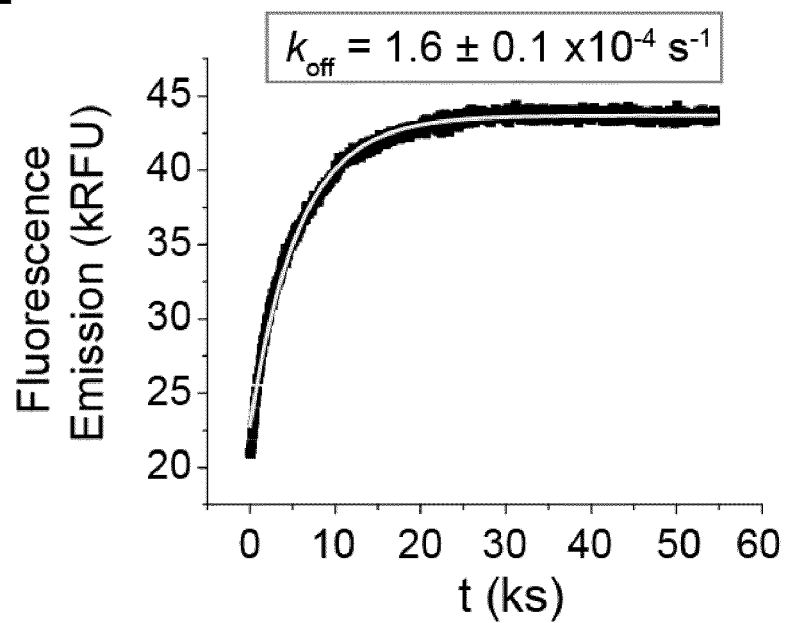

In a further preferred embodiment, said negatively charged macromolecule is an ON which is bound to the nanoparticle with an association rate constant, $k_{on}$ of $(6.6 \pm 0.6) \times 10^5$ $M^{-1}$ $s^{-1}$ (FIG. 2c). Binding kinetics are determined by measuring fluorescence quenching and fluorimetry. Data were fit to a single exponential decay (rate constants ($k_{obs}$) plotted against the ON concentration, with a linear fit).

In a further preferred embodiment, said negatively charged macromolecule is an ON which dissociates from the nanoparticle with dissociation constant, $K_d$ of $(2.4\pm0.3)\times10^{-10}$ M and dissociation rate constant, $k_{off}$ of $(1.6\pm0.1)\times10^{-4}$ s$^{-1}$. To determine the off-rate, a 100-fold excess of unlabeled DNA was used to induce slow release of encapsulated Atto488-ssDNA cargo (FIG. 2d). The data were fit to a single exponential decay providing the dissociation rate constant, k off of $(1.6\pm0.1)\times10^{-4}$ s$^{-1}$. The association and dissociation rate constants were used to calculate an equilibrium dissociation constant, $K_d$ of $(2.4\pm0.3)\times10^{-10}$ M.

In a preferred embodiment, the negatively charged macromolecule included in the complex is a nucleic acid, preferably an ON and said nanoparticle of the complex of the invention is capable of protecting said nucleic acid, preferably said ON from degradation by nucleases. In a preferred embodiment, said nucleases have a molecular weight of more than 14 kD, preferably more than 20 kD, more preferably more than 30 kD, again more preferably more than 40 kD, again more preferably more than 50 kD, and again more preferably 60 kD or more than 60 kD. In a preferred embodiment, said nucleases have a molecular weight of more than 14 kD. In a preferred embodiment, said nucleases have a molecular weight of 60 kD or more.

In a preferred embodiment, the complex or nanoparticle of the invention shows an approximately 30-fold increased cellular uptake compared to control with a naked, i.e. free Atto488-ssDNA.

In a further aspect, the invention provides a method for manufacturing the nanoparticle of the invention comprising the step of self-assembling of the polypeptide of the invention into said nanoparticle.

In a preferred embodiment, the method for manufacturing the nanoparticle of the invention comprises the steps of (i) producing the polypeptide of the invention, and (ii) self-assembling of the polypeptide of the invention into said nanoparticle. The polypeptide for manufacturing the nanoparticle of the invention is preferably produced by recombinant expression. In a preferred embodiment, said polypeptide is recombinantly expressed in bacterial cells, preferably in Escherichia coli cells. Upon expression, the polypeptide of the invention self-assembles into a well-defined nanoparticle which can be isolated.

In a preferred embodiment, the method for manufacturing the nanoparticle further comprises the step of isolating the nanoparticle. Said isolation step is preferably affinity chromatography, more preferably immobilized metal affinity chromatography. In a preferred embodiment, said isolation step is affinity chromatography using a support that comprises nickel, cobalt or copper. Most preferably, said isolation step is Ni-NTA affinity chromatography.

Due to the positively charged interior of the nanoparticle of the invention, contamination of nucleic acids originating from the host cells expressing the polypeptide of the invention is possible. These undesired cargos can be removed with high ionic strength to weaken electrostatic interactions, and RNase A to digest contaminant RNA.

Thus, in a preferred embodiment, the method for manufacturing the nanoparticle further comprises the step of treating the nanoparticle with high ionic strength buffer and/or RNase. In a preferred embodiment, said high ionic strength buffer has an ionic strength of 0-2 M. In a further preferred embodiment, said method for manufacturing the nanoparticle of the invention comprises the steps of (i) producing the polypeptide of the invention via recombinant expression, (ii) treating the expressed polypeptide in a buffer having an ionic strength of 0-2 M and comprising RNase and/or DNase, and self-assembling of the polypeptide of the invention into said nanoparticle. Preferably, said high ionic strength of 0-2 M of said buffer is regulated by addition of NaCl. Preferably, said high ionic strength buffer comprises sodium phosphate buffer, NaCl, imidazole and optionally lysozyme in addition to RNase and/or DNase. Said buffer comprises for example, about 50 mM sodium phosphate buffer (pH 7.4), about 1000 mM NaCl and imidazole supplemented with lysozyme, DNase I and RNase A. Said high ionic strength buffer contains at least 20 mM imidazole.

In a further aspect, the invention provides a method for manufacturing the complex of the invention comprising the step of mixing the nanoparticle of the invention with one or more negatively charged macromolecules. In a preferred embodiment, said step of mixing takes place in an aqueous buffer, preferably at room temperature.

In a further aspect, the invention provides a method for transfecting a cell comprising the step of contacting said cell with the complex of the invention.

As used herein the term "transfection" refers to the process of introducing negatively charged macromolecules, preferably nucleic acids, more preferably ON into cells. Preferably, said method for transfecting a cell is an in vitro process.

In a preferred embodiment, said cell is a eukaryotic cell. More preferably, said cell is an animal cell, again more preferably a mammalian cell.

In a further aspect, the invention relates to use of the complex of the invention for transfecting a cell.

EXAMPLES

Example 1—Materials and Methods

Materials and Instrumentation

All enzymes used for molecular cloning were purchased from New England BioLabs (USA). All synthetic oligonucleotides were purchased from Microsynth AG (Switzerland). Plasmid miniprep and DNA purification kits were purchased from Zymo Research (USA). Isopropyl-beta-D-thiogalactopyranoside (IPTG) was purchased from Fluorochem (UK). Lysozyme was purchased from PanReac Axon Lab AG (Switzerland). For His-tagged protein isolation, Ni-NTA Agarose from Qiagen (Germany) was used. DNase I was from Roche (Switzerland) and RNase A was from Merck (Germany). Benzonase was purchased from Merck-Millipore (USA). GeRed was purchased from Biotium, Inc. (USA). The plasmid pET29b(+)-O3-332 was kindly provided by Prof. David Baker.

DNA and protein quantification were carried out using a NanoDrop 2000c spectrophotometer from ThermoFisher Scientific Inc. (USA). All size-exclusion chromatography was carried out on an NGC™ Medium-Pressure Chromatography System from Bio-Rad Laboratories, Inc. (USA). Sodium dodecyl sulfate polyacrylamide gel electrophoresis (SDS-PAGE) was run and developed on a PhastGel system from GE Healthcare (USA). Agarose gel electrophoresis (AGE) and denaturing polyacrylamide gel electrophoresis (PAGE) were performed on Mini-Sub® cell GT and Mini-PROTEAN systems respectively, both from Bio-Rad Laboratories, Inc. (USA). Gel images were captured using an EOS 1100D from Canon (Japan). Transmission electron microscopy (TEM) images were obtained on a Morgagni 268 from FEI (USA). Fluorescence microscopy images were obtained on an Eclipse-Ti inverted microscope from Nikon (Japan). Confocal fluorescence microscopy images were obtained on an SP8-AOBS from Leica (Germany). Flow cytometry was carried out on an LSRFortessa from BD Biosciences (USA).

Molecular Modelling

The X-ray diffraction data for the original O3-33 assembly (PDB: 3VCD) (King, N. P et al., Science 2012, 336, 1171-1174) was used to choose sequence positions for mutation to arginine, which were modelled in using the Dynameomics backbone-independent rotamer library (Scouras, A. D. et al., Protein Sci. 2011, 20, 341-352) through UCSF Chimera (Pettersen, E. F. et al., J. Comput. Chem. 2004, 25, 1605-1612).

Molecular Cloning

The gene for OP was purchased from ATG:biosynthetics (Germany) and obtained as plasmid pGH-OP. The OP gene insert was excised from pGH-OP and cloned into the vector pET29b(+)-O3-33 vector (King et al., 2012, op cit.) using XhoI and NdeI restriction sites, replacing the O3-33 gene and affording plasmid pET29b(+)-OP. The gene for OP without a His6 tag was prepared by cloning in a DNA cassette coding for GS** at the XhoI site, which is immediately upstream the His6 tag. Plasmid sequences were confirmed by Sanger DNA sequencing performed by Microsynth AG (Switzerland).

Protein Expression

Proteins were expressed in E. coli strain BL21-Gold (DE3), which was transformed with either pET29b(+)-O3-33, pET29b(+)-OP or pET29b(+)-OP_NoHis6. Cells were grown at 37° C. in LB medium containing kanamycin sulfate (86 μM) until $OD_{600}$ reached 0.6-0.8, and protein overexpression was induced with IPTG (0.1 mM). After culturing for ~18 h at 25° C., cells were harvested by centrifugation (5,000×g) at 4° C. for 15 min. Cell pellets were stored at −20° C. until purification.

Cell Lysis, Ni-NTA and RNA Removal for OP

As OP is capable of loading small RNA molecules during expression in E. coli, optimized protocols were developed to isolate the empty cage in good purity. These involve using high ionic strength buffer to weaken the interaction with nucleic acids as well as extended incubation with RNase A. Each cell pellet from 800 mL of culture was resuspended in 10 mL of lysis buffer (50 mM sodium phosphate buffer (pH 7.4), 1000 mM NaCl, 20 mM imidazole) supplemented with lysozyme (0.1 mg/mL), DNase I (10 U/mL), RNase A (5 U/mL), and protease inhibitor cocktail (Sigma), and incubated at 37° C. for 1.5 h.

After lysis, sonication and centrifugation (10,000×g) at 25° C. for 25 min, the supernatant was loaded onto 5 mL of Ni-NTA resin in a gravity flow column and incubated for 15 min. After multiple washes with lysis buffer containing 20 mM and 40 mM imidazole, the target protein was eluted with elution buffer (50 mM sodium phosphate buffer (pH 7.4), 300 mM NaCl, 500 mM imidazole). Typically, between 10-20 mL were collected and supplemented with 2 U/mL RNase A, 5 mM EDTA and protease inhibitor cocktail and incubated overnight at 37° C. to digest any contaminant E. coli RNA which was not removed during the Ni-NTA purification. The protein was then ready for SEC. After this point, the storage of the protein and all experiments were at carried out at room temperature unless specified otherwise.

Lysis and Ni-NTA for O3-33

Isolation of O3-33 followed the same steps as for OP but with less stringent conditions as nucleic acid contamination is not an issue. For lysis, sonication, and Ni-NTA the buffer used was of lower ionic strength (50 mM sodium phosphate buffer (pH 7.4), 300 mM NaCl, and 20 mM imidazole). After isolation from Ni-NTA with elution buffer (50 mM sodium phosphate buffer (pH 7.4), 300 mM NaCl, 500 mM imidazole) the protein was ready for SEC.

Size-Exclusion Chromatography (SEC)

Before SEC, protein samples were buffer exchanged to 20 mM sodium phosphate buffer (pH 7.4) with 200 mM NaCl and 5 mM EDTA using an Amicon Ultra-15 centrifugal filter unit (30 k MWCO) (Merck Millipore, USA). This process also removes some of the RNase A and digested nucleic acid fragments from OP. Fully assembled 24-mer cages were then isolated by SEC using a Superose 6 Increase 10/300 GL column from GE Healthcare (USA) with a flow rate of 1.0 mL/min at room temperature. Both O3-33 and OP cages elute at 15-16 mL with an eluent of 20 mM sodium phosphate buffer (pH 7.4) containing 200 mM NaCl and 5 mM EDTA. Purified proteins were stored in the SEC eluent buffer at room temperature. Proteins were quantitated by absorbance at 280 nm. Additionally, the removal of all RNA was verified from the $A_{260}/A_{280}$ ratio and by native agarose gel stained with GelRed, which is a sensitive nucleic acid stain. Protein purity was verified by SDS-PAGE with Coomassie Blue staining.

General Characterization of Protein Cages

All native gel electrophoresis was carried out using 2% or 3% (w/v) agarose gels in Tris-acetate-EDTA buffer (40 mM Tris-HCl, 19 mM acetic acid, 1 mM EDTA, pH 8.3). Gels were cast with GelRed for the detection of unlabeled nucleic acid as needed and were stained with Coomassie Blue for protein visualization. In a typical experiment for the analysis of protein, ca. 100 or 200 pmol of capsid (with respect to monomer) was loaded per lane in 10 μL of buffer with an additional 2 μL of 70% (v/v) aqueous glycerol. The gels were run for 30 minutes at 100 V, stained with Coomassie Blue for visualization of the proteins, ONs were detected with Atto488-fluorescence.

SEC analysis was performed under the same conditions used for cage isolation. Negatively-stained transmission electron microscopy (TEM) was carried out as reported previously (Beck, T. et al., Angew. Chem. Int. Ed. 2015, 54, 937-940). For all TEM experiments, protein samples of between 3-5 M (monomer) in storage buffer (20 mM sodium phosphate buffer (pH 7.4), 200 mM NaCl and 5 mM EDTA) were used. DLS measurements were carried out on Zetasizer Nano (Malvern Instruments, UK) at 25° C. using 0.22 μm filtered samples of 150-250 μM (monomer) in storage buffer.

Melting Temperatures

Melting temperatures were obtained using the Protein Thermal Shift™ Dye Kit (Thermo Fisher Scientific, USA) on a StepOnePlus Real-Time PCR System (Applied Biosystems, USA). Proteins were measured in triplicate at 5, 10 and 20 μM in a buffer comprised of 25 mM Tris-HCl (pH 8.0), 200 mM NaCl. All data were averaged to produce the values.

TABLE 4

| Melting temperatures | |
|---|---|
| Protein | Tm (° C.) |
| O3 | 96.08 ± 0.09 |
| O3 + siRNA | 95.98 ± 0.28 |
| OP | 94.42 ± 0.33 |
| OP + siRNA | 95.80 ± 0.63 |

Table 4 shows melting temperatures Tm for O3-33 and OP proteins in the presence and absence of two equivalents of siRNA duplex.

Protein Crystallography

A Phoenix crystallization robot (Art Robbins Instruments) was used to set up sitting-drop vapor-diffusion experiments in Intelli-Plate R96-3 LV. Initial crystallization attempts were carried out at 20° C. Well-diffracting OP crystals were obtained at 20° C., in 2 M $(NH_4)_2SO_4$ and 5% 2-propanol with 3 mg/mL of the enzyme solution by using the sitting-drop vapor-diffusion method. The crystals were transferred into reservoir solutions with 20% (v/v) glycerol as a cryo-protectant, and then flash cooled at −173° C. in a nitrogen-gas stream. X-ray diffraction data sets were collected at X06SA at the Swiss Light Source (Paul Scherrer Institute, Villigen, Switzerland) using an EIGER X 16M detector. We used wavelengths of 1.0000 Å for data collection.

The diffraction data for OP was processed and scaled using the XDS program package (Kabsch W., Acta Crystallogr. D Biol. Crystallogr. 2010, 66, 125-132). The initial phase was determined by molecular replacement, using the structure of O3-33 (PDB code: 3VCD) as a search model. Molecular replacement was performed with Phaser (McCoy, A. J. et al., J. Appl. Crystallogr. 2007, 40, 658-674). The structure was modified manually with Coot (Emsley, P. et al., Acta Crystallogr. D Biol. Crystallogr. 2004, 60, 2126-2132) and refined with PHENIX (Adams, P. D. et al., Acta Crystallogr. D Biol. Crystallogr. 2010, 66, 213-221). The final crystal data and intensity statistics are summarized in Table 5.

Electrophoretic Mobility Shift Assays (EMSAs)

All EMSAs were carried out on 3% (w/v) agarose gels as described above. For Atto488-labelled ssDNA, 10 pmol of DNA was used per sample (=one gel lane) and incubated at room temperature with varying molar equivalents of protein in a total volume of 10 μL of PBS. For unlabeled dsDNA and dsRNA, 40 pmol of duplex was used per sample under the same incubation conditions and the gel was cast with GeRed for visualization.

Cargo Loading Capacity

Pure OP protein (1 nmol) was incubated overnight at room temperature with 5 equivalent of either ssDNA, dsDNA or dsRNA in a total volume of 200 μL of SEC buffer (20 mM sodium phosphate buffer (pH 7.4), 200 mM NaCl and 5 mM EDTA). The mixtures were purified by SEC and absorbance spectra were obtained. All absorbance spectra were corrected for light scattering using the ale UV-Vis-IR software. Protein and nucleic acid concentrations were determined from absorbance values at 280 and 260 nm using an equation described by Porterfield and Zlotnick (Porterfield, J. Z. et al., Virology 2010, 407, 281-288).

Encapsulation Kinetics

All kinetic measurements were carried out at room temperature in PBS. For each experiment to determine $k_{on}$, the fluorescence emission of an 800 μL solution of Atto488-labelled DNA (10 nM) was measured at 515 nm (excitation, 488 nm) and this value was taken as t=0 s. Next, a small volume of concentrated OP solution was added to give a final concentration of 5-125 nM and the drop in emission over time was monitored at intervals of 10 s. Each measurement of emission vs. time was fit to single exponential, providing $k_{obs}$ for each concentration of OP. These $k_{obs}$ values were then plotted against [OP] and $k_{on}$ was obtained from the slope of a linear fit. The values for $k_{obs}$ at low concentrations (<25 nM) of OP are unreliable due to a shift from one to two guest DNA molecules per cage (FIG. 17). As such, only $k_{obs}$ in the range from 25-125 nM were used to determine $k_{on}$ and the y-intercept for the linear fit was fixed to the determined $k_{off}$ value of 1.6×10−4 s.

For the determination of $k_{off}$, an 800 μL solution of Atto488-labelled DNA (10 nM) and OP (5 nM) was incubated until no further change in fluorescence was observed. This provides OP cages containing two ssDNA molecules, which simplifies the $k_{off}$ measurement to only one rate constant as the case of encapsulation of a second DNA molecule to a 1:1 complex is removed. Due to the high stability of the OP:DNA complex, an excess of unlabeled ssDNA was used to displace the encapsulated Atto488-DNA and recover fluorescence as it is released from the protein cage. The change on fluorescence emission at 515 nm was monitored at 60 s intervals for 16 hours after the addition of 1 μM of unlabeled ssDNA. The data was fit to a single exponential to generate $k_{off}$.

Nuclease Digestion Assay

Figure 14:
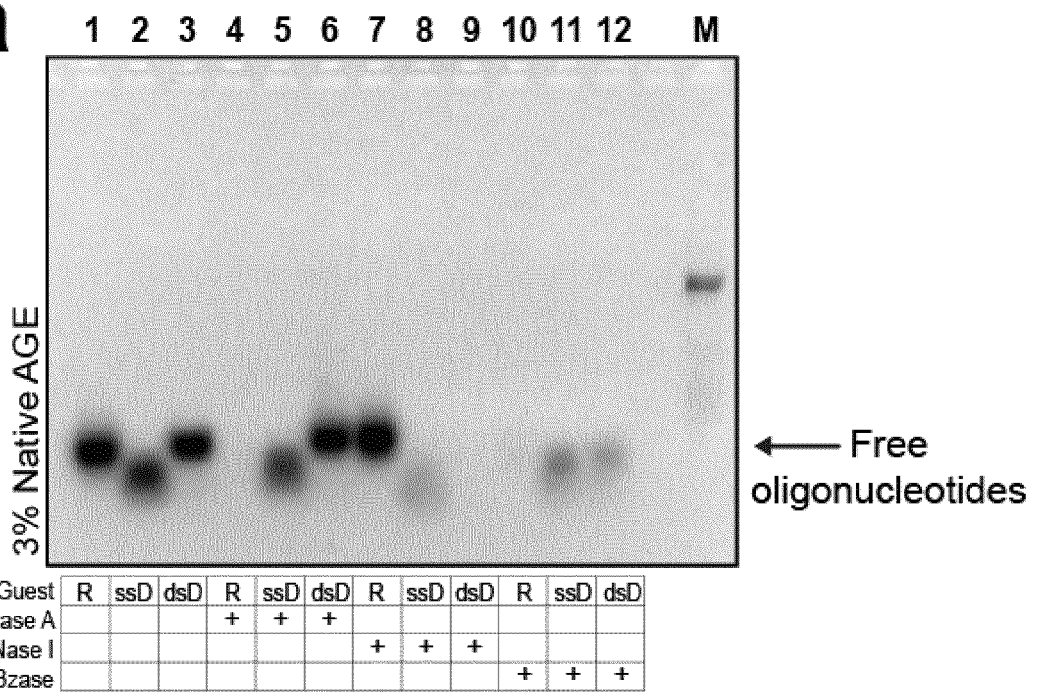
FIG. 14: Nuclease assay. Native agarose gels showing (a) free nucleic acid (R=dsRNA, ssD=ssDNA and dsD=dsDNA) treated with the nucleases indicated (Bzase=Benzonase) and (b) the same nucleic acid pre-packaged in OP cages, also treated with the nucleases indicated. Lane M contains a 300 nt ssRNA for reference. Samples were incubated with the nucleases for 18 hours at 37° C. in PBS. There is some incomplete digestion in the case of Benzonase for the DNA samples and for single-stranded DNA with DNase I (a, top gel lanes 8, 11 and 12). Nevertheless, a comparison of the encapsulated samples with those fully digested clearly reveals that OP can protect its cargo from the larger nucleases, Benzonase and DNase I, while the smaller RNase A is able to enter the cage and digest RNA cargo.
Figure 14:
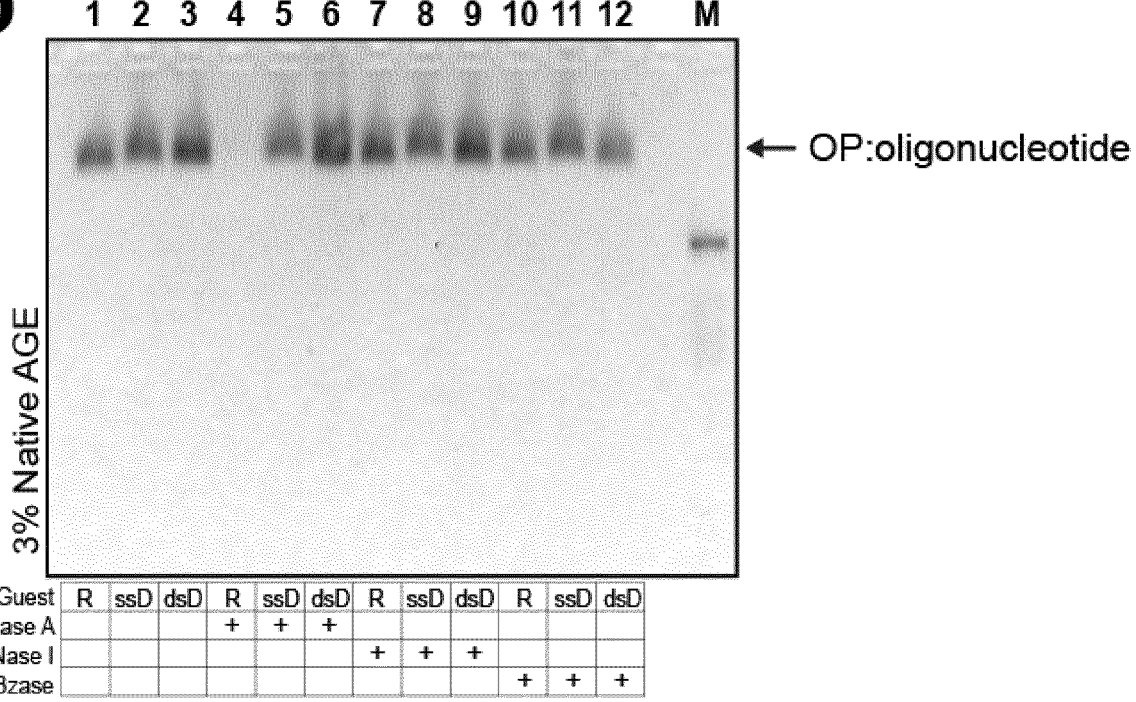

Complexes (1:1 molar ratio) of OP with either ssDNA, dsDNA or dsRNA were prepared by incubation in PBS at room temperature for 1 hour. Equivalent stocks that only contained nucleic acid were also prepared. Stocks were then divided into aliquots to provide samples for each gel lane. Each sample contained 24 pmol of OP/nucleic acid in a total volume of 10 μL PBS supplemented with $MgCl_2$ (2.5 mM), $CaCl_2$ (0.5 mM). Control samples were kept as such and nuclease samples were supplemented with 0.2 U of either RNase A, DNase I or Benzonase. All samples were then incubated at 37° C. for 18 hours before analysis by native agarose gel stained with GelRed and then Coomassie Blue (FIG. 14).

Cell Culture

HeLa and A431 cells were maintained in Dulbecco's Modified Eagle Medium (high glucose), MCF-7 and Vero cells in Iscove's Modified Dulbecco's Medium, HepG2 and HT29 in RPMI-1640 medium and CHO in Ham's F-12K medium. In all cases media was supplemented with 10% fetal bovine serum (FBS), 2 mM L-glutamine, 2 mM GlutaMAX and 1 μg/mL gentamicin. Cells were cultured in 5% $CO_2$ at 37° C. and typically split in a 1:4 ratio every 3 days. HeLa-GFP cells were maintained in the same manner as HeLa cells with the addition of 0.1 mM non-essential amino acids (NEAAs) and 10 μg/mL blasticidin (selection antibiotic) to the media. Neither NEAA nor blasticidin were added to media for experiments as it was found they had no effect within those timeframes. Cytotoxicity The cytotoxicity of OP and Lipofectamine 2000 (Thermo Fisher Scientific, USA) was assessed using the WST-8-based Cell Counting Kit-8 from Sigma according to the manufacturer's instructions. HeLa cells were seeded at a density of 5,000 cells per well in a 96-well plate in 100 μL of culture medium and allowed to recover at 37° C. and 5% $CO_2$ for 24 hours. OP (pre-sterilized by filtration through a 0.22 μm membrane) and Lipofectamine 2000 samples were prepared by serial dilution in sterile PBS. A total volume of 10 μL sample was added to each well to provide the final concentrations shown in FIG. 15. As a negative control 10 μL of 10% Triton X-100 in PBS were used per well. The positive control was just PBS. Cells were incubated for 24 h or 48 h in 5% $CO_2$ at 37° C. before addition of 10 μL of CKK-8 reagent to each well. The plate was then incubated for 4 hours at 37° C. and 5% CO2 before measuring absorbance at 450 nm. The absorbance of CKK-8 in culture media, without cells, was used for background subtraction and samples were normalized to untreated cells to provide the values shown in FIG. 15. Samples were measured in triplicate.

Cellular Uptake by Flow Cytometry

HeLa cells were seeded at a density of 30,000 cells per well in a 24-well plate in 500 μL of culture medium and allowed to recover at 37° C. and 5% $CO_2$ for 24 hours to reach 70-90% confluency. Both OP protein and Atto488-

DNA were sterilized by filtration through a 0.22 μm membrane, and stocks were prepared in sterile PBS. For each well 20 μL of sample in PBS was added to 200 μL of culture media to give a final Atto488-DNA concentration of 200 nM. Cells were incubated for 24 h in 5% $CO_2$ at 37° C. before washing with PBS and trypsinization (0.05% Trypsin-EDTA (Thermo Fisher Scientific, USA), 4 minutes at 37° C.). Cells were collected in cold culture medium and washed twice with cold PBS before resuspension in flow cytometry buffer (PBS with 5% FBS and 10 μg/mL propidium iodide).

Cellular Uptake by Confocal Fluorescence Microscopy

HeLa cells were seeded at a density of 15,000 cells per well in a slide 8-well chambered coverslip with ibiTreat surface from ibidi GmbH (Germany). Cells were incubated in 200 μL of culture medium at 37° C. and 5% $CO_2$ for 24 hours before sample addition. Both OP protein and Atto488-DNA were sterilized by filtration through a 0.22 μm membrane, and stocks were prepared in sterile PBS. For each well 10 μL of sample in PBS was added to 100 μL of culture media to give a final Atto488-DNA concentration of 200 nM. Cells were incubated for 24 h in 5% C $CO_2$ O2 at 37° C. before washing with PBS and nuclear staining with 100 μL of Hoechst 33342 solution (5 μg/mL in PBS) at 37° C. for 10 mins. Cells were then washed twice with PBS and microscopy was carried out at 37° C. in PBS containing 5% FBS.

GFP Knockdown

HeLa-GFP cells were seeded at a density of 30,000 cells per well in 500 μL of culture medium in a 24-well plate in media and allowed to recover at 37° C. and 5% CO2 for 24 hours to reach ~70% confluency. Sterile protein, RNA and Lipofectamine 2000 samples were prepared in PBS. With the exception of the Lipofectamine 2000 controls, all samples (20 μL in PBS) were added to cells in 200 μL OptiMEM and incubated for 4 hours at 37° C. and 5% $CO_2$ before the addition of 300 μL of full culture media. The cells were then further incubated at 37° C. and 5% $CO_2$ to give a total of 48 hours between sample addition and flow cytometry analysis. Although there was negligible change in the knockdown efficiency of Lipofectamine 2000 under the conditions used for all other samples, toxicity was an issue. As such, we used the minimal amount of Lipofectamine 2000 necessary, which caused the least toxicity without compromising knockdown efficiency. This was determined to be 1 μL of Lipofectamine 2000 per 40 pmol of siRNA, which is also the minimal amount recommended by the manufacturer. We then used the manufacturer's recommended protocol and incubated cells with siRNA lipoplexes (pre-prepared in PBS) in culture media for 48 hours at 37° C. and 5% $CO_2$ before flow cytometry analysis.

Figure 16:
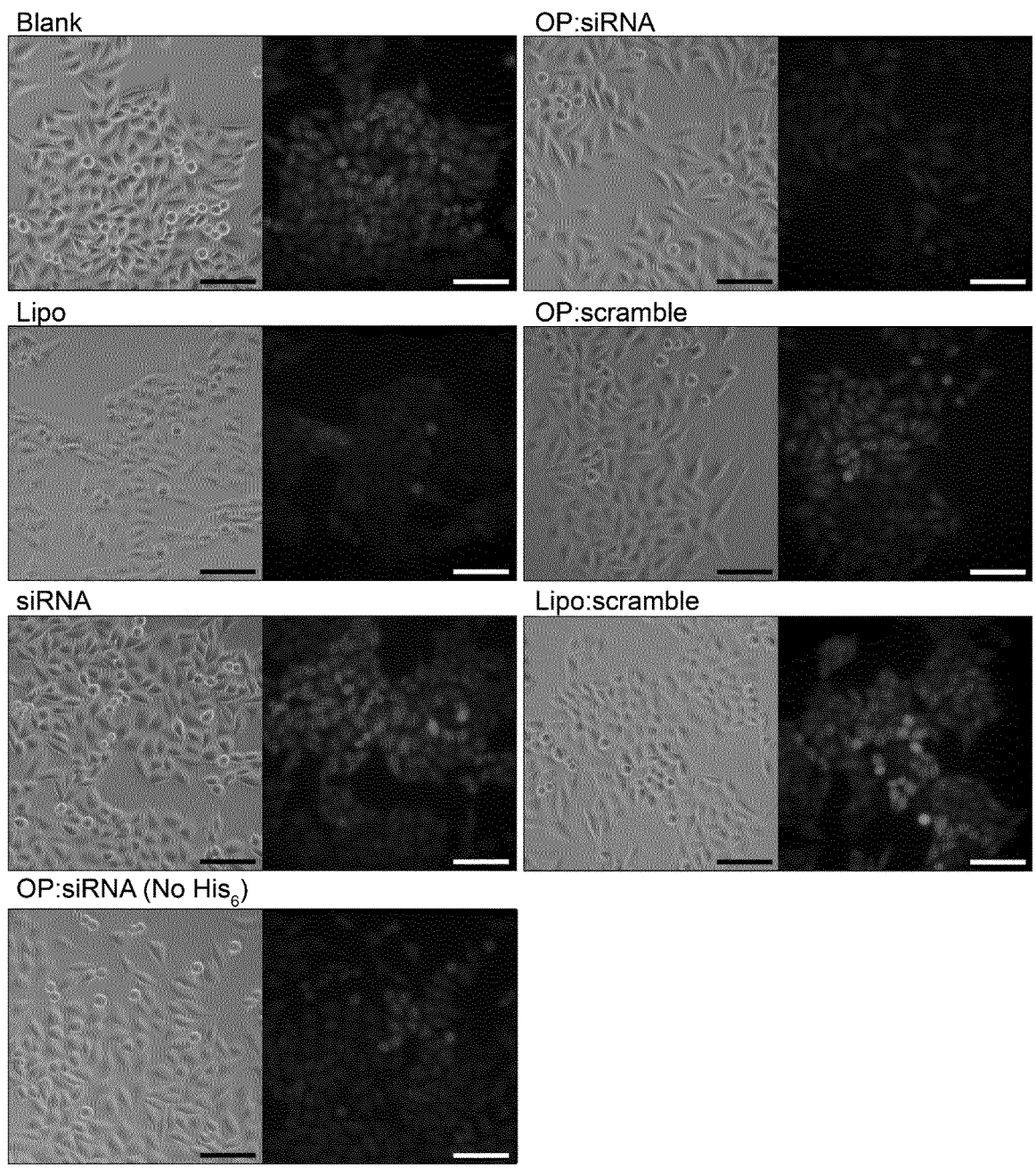
FIG. 16: Qualitative assessment of GFP knockdown by fluorescence microscopy. Knockdown of GFP expression in HeLa cells, shown in terms of relative GFP content from live-cell fluorescence microscopy. The trends seen here match well with the quantitative flow cytometry analysis (FIG. 4a). Sample names are shown above each panel pair, where left is brightfield and right is GFP fluorescence (LED excitation at 470 nm, emission filter 535/50 nm). The concentration of siRNA for each sample is 100 nM and images were obtained 46 hours after the addition of siRNA samples. Scale bars are 100 μm.
Figure 17A:
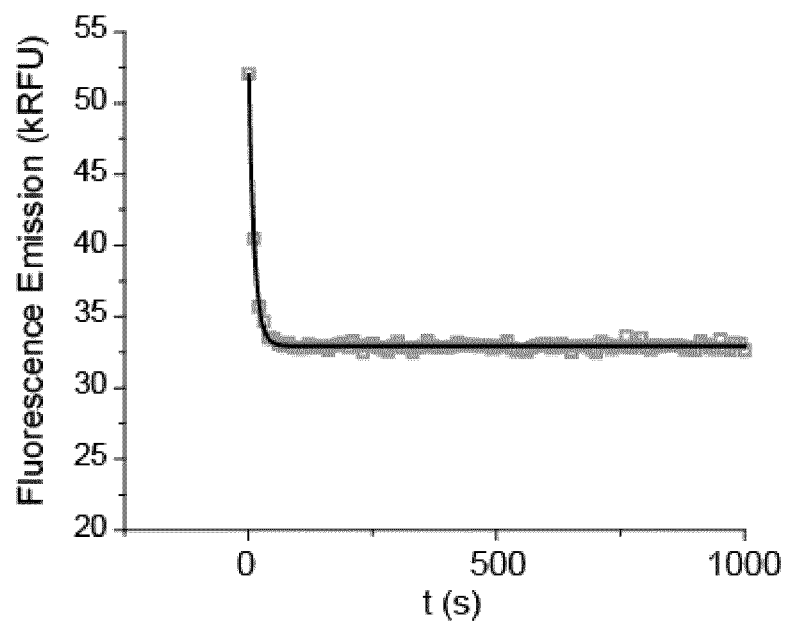
FIG. 17: Kinetics at higher DNA to OP ratios. At higher ratios of Atto488-DNA to OP, two effects are observed that are consistent with the loading of two molecules of ssDNA per OP cage. Firstly an increased quenching is observed, which is evident from the end points in (a)-(c). This is most likely due to self-quenching of the fluorophores which are at a high effective concentration in the small cavity of OP. The second effect is a transition from a single to a double exponential decay, revealing two distinct binding events. Single exponential fits are shown as solid and double exponential as dashed lines for (b) and (c).
Figure 17B:
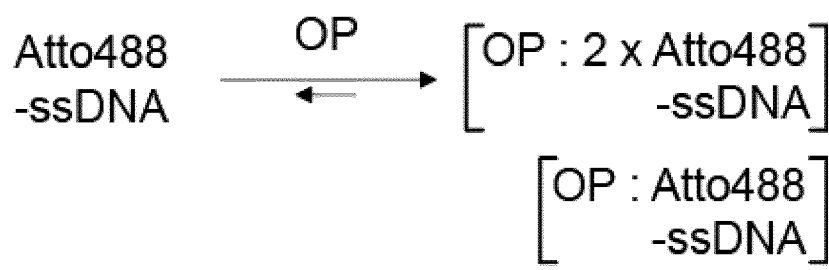
Figure 17B:
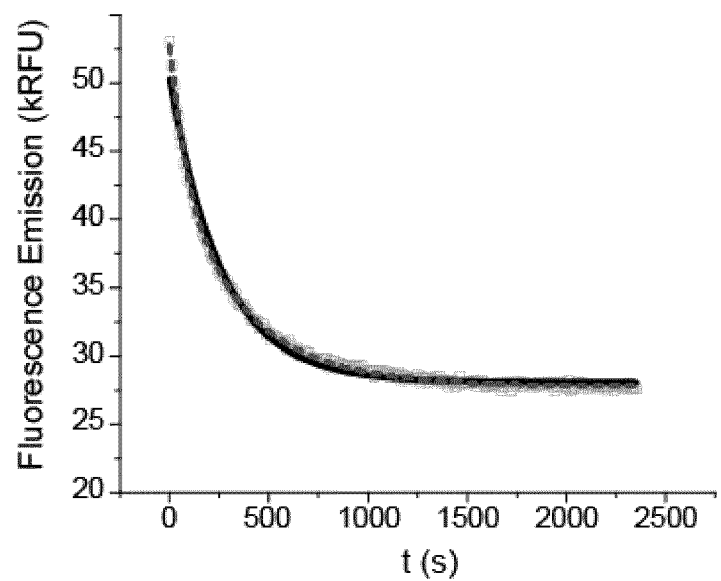
Figure 17C:
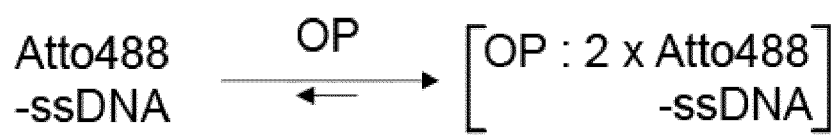
Figure 17C:
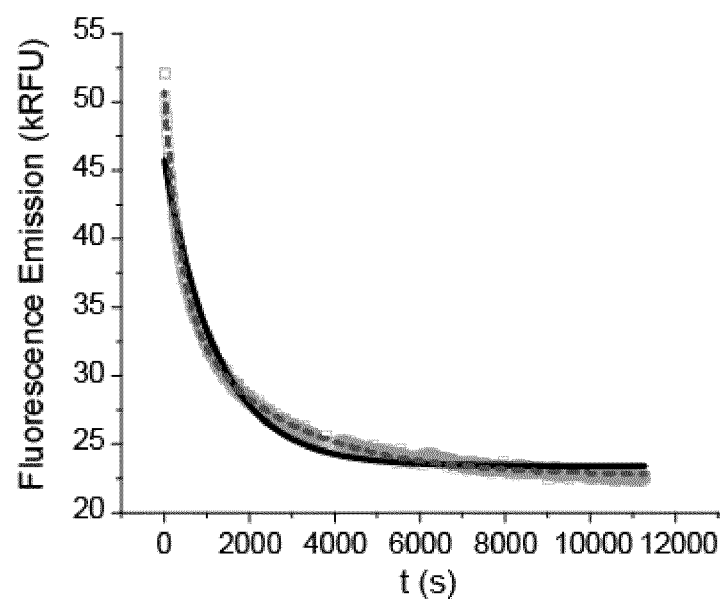
Figure 18:
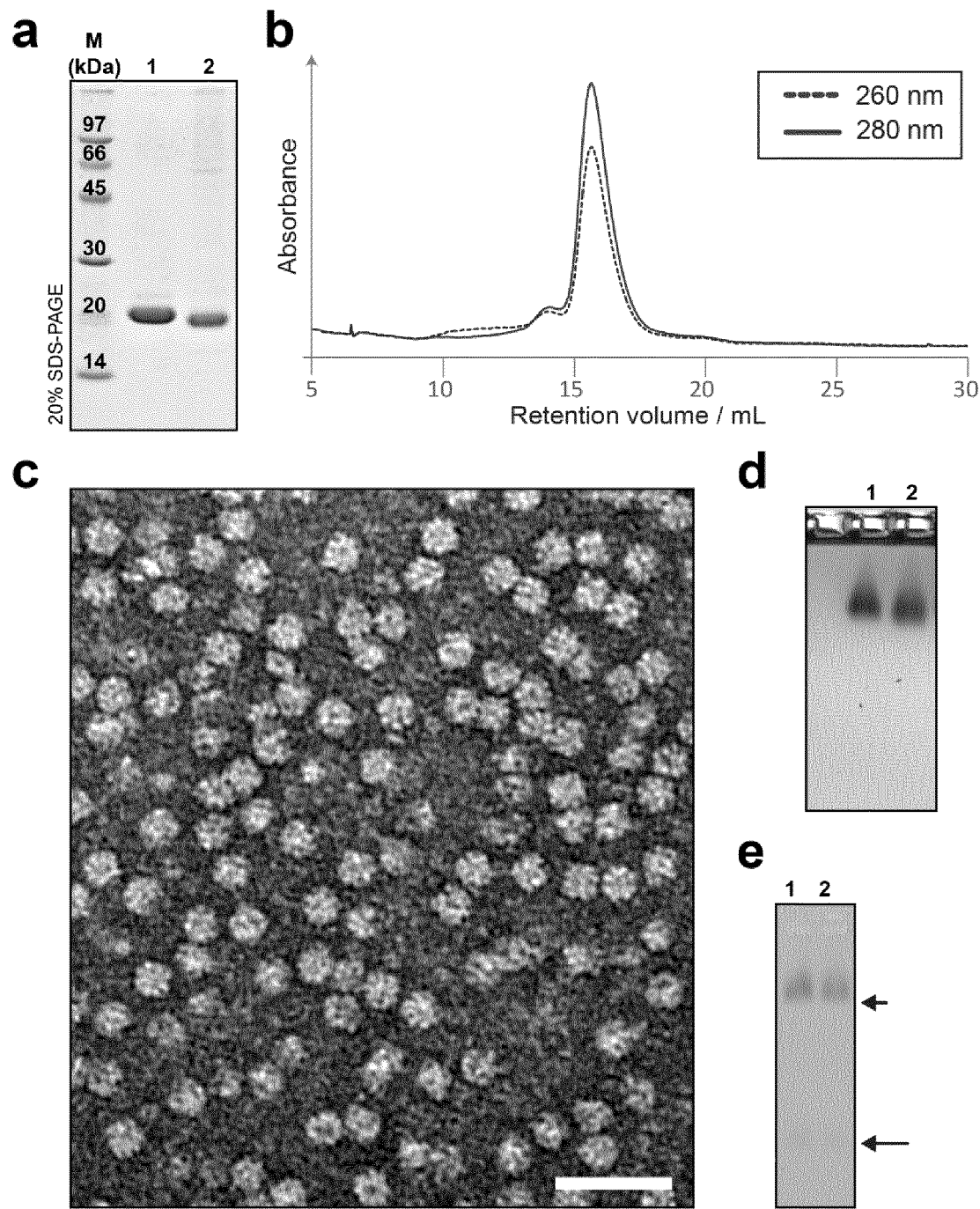
FIG. 18: Characterization of OP with no His6 tags. (a) SDS-PAGE comparison of OP (lane 1) and OP-NoHis6 (lane 2). (b) SEC of OP-NoHis6 shows a similar retention volume (16 mL) as OP. (c) Negative stain TEM of OP-NoHis6 looks consistent with OP. (d) Native AGE of lane 1: OP and Lane 2: OP-NoHis. Gel visualized with Coomassie Blue for protein. (e) Native AGE showing siRNA encapsulation at a 1:1 molar ratio in OP (lane 2) and OP-NoHis6 (lane 3). Lane 1 is the free siRNA control. Visualized with GelRed for nucleic acid. (f) SEC of OP-NoHis6 after incubation with 5 equiv. of siRNA exhibits the same retention volume as the empty cage (16 mL), but with an increased A260/A280 ratio, indicating internalization of the oligonucleotide. The peaks at 19-21 mL correspond to excess RNA.
Figure 18F:
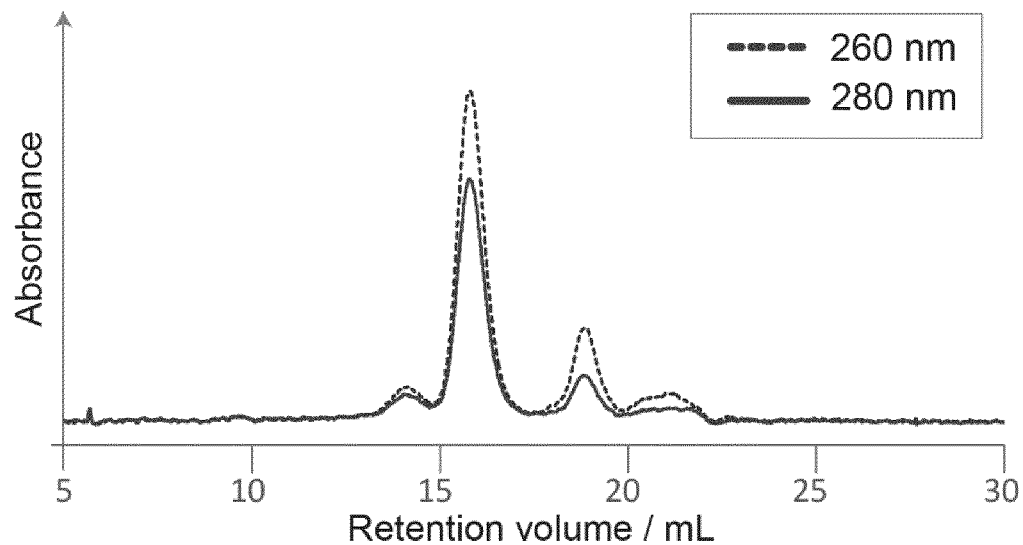

Before flow cytometry analysis, fluorescence microscopy was carried out directly on the 24-well plates to get a qualitative measure of the GFP expression level and assess cell health (FIG. 16). Cells were then washed with PBS and trypsinized. Cells were collected in cold culture media and washed twice with cold PBS before resuspension in flow cytometry buffer (PBS with 5% FBS and 10 μg/mL propidium iodide). Untreated HeLa-GFP cells, with matched media and incubation conditions as the samples, were used as a positive control and HeLa cells not expressing GFP were used as a negative control for GFP fluorescence to optimize cytometer settings. Samples were measured in at least triplicate on numerous occasions with different batches of protein and siRNA.

Purification of OP without His6 Tags

Ammonium sulfate precipitation was used as reported previously (Beck, T. et al., Angew. Chem. Int. Ed. Engl., 2015, 54, 937-940), but with modifications in order to optimize the removal of small RNA molecules. Each cell pellet from 800 mL of culture was re-suspended in 10 mL of buffer (25 mM Tris-HCl buffer (pH 8.0), 1000 mM NaCl) supplemented with lysozyme (0.1 mg/mL), DNase I (10 U/mL), RNase A (5 U/mL), and protease inhibitor cocktail (Sigma), and incubated at 37° C. for 1.5 h. After lysis, the suspension was sonicated and centrifuged (10,000×g, 25° C., 25 min.). Next, the supernatant was heated to 65° C. for 30 minutes and centrifuged (10,000×g, 4° C., 25 min.) to pellet the denatured E. coli proteins. Ammonium sulfate was added to the supernatant to 70% of its saturation concentration and the suspension was centrifuged (10,000×g, 4° C., 20 min.). The protein pellet was re-suspended in 20 mL of buffer (25 mM Tris-HCl buffer (pH 8.0), 1000 mM NaCl) and subjected to ammonium sulfate precipitation twice more. Finally, the precipitated protein was re-suspended in a lower salt buffer (25 mM Tris-HCl buffer (pH 8.0), 200 mM NaCl), supplemented with 2 U/mL RNase A, 5 mM EDTA and protease inhibitor cocktail, and then incubated overnight at 37° C. to digest any contaminant E. coli RNA. The protein was then purified by SEC, which was carried out in a buffer comprised of 25 mM 2-(N-morpholino)ethanesulfonic acid (pH 5.5), 1000 mM NaCl and 250 mM MgSO4 to weaken interactions between any remaining guest molecules and the protein cage. After this point, protein was stored in PBS buffer at room temperature.

Cargo Displacement by tRNA

Figure 4:
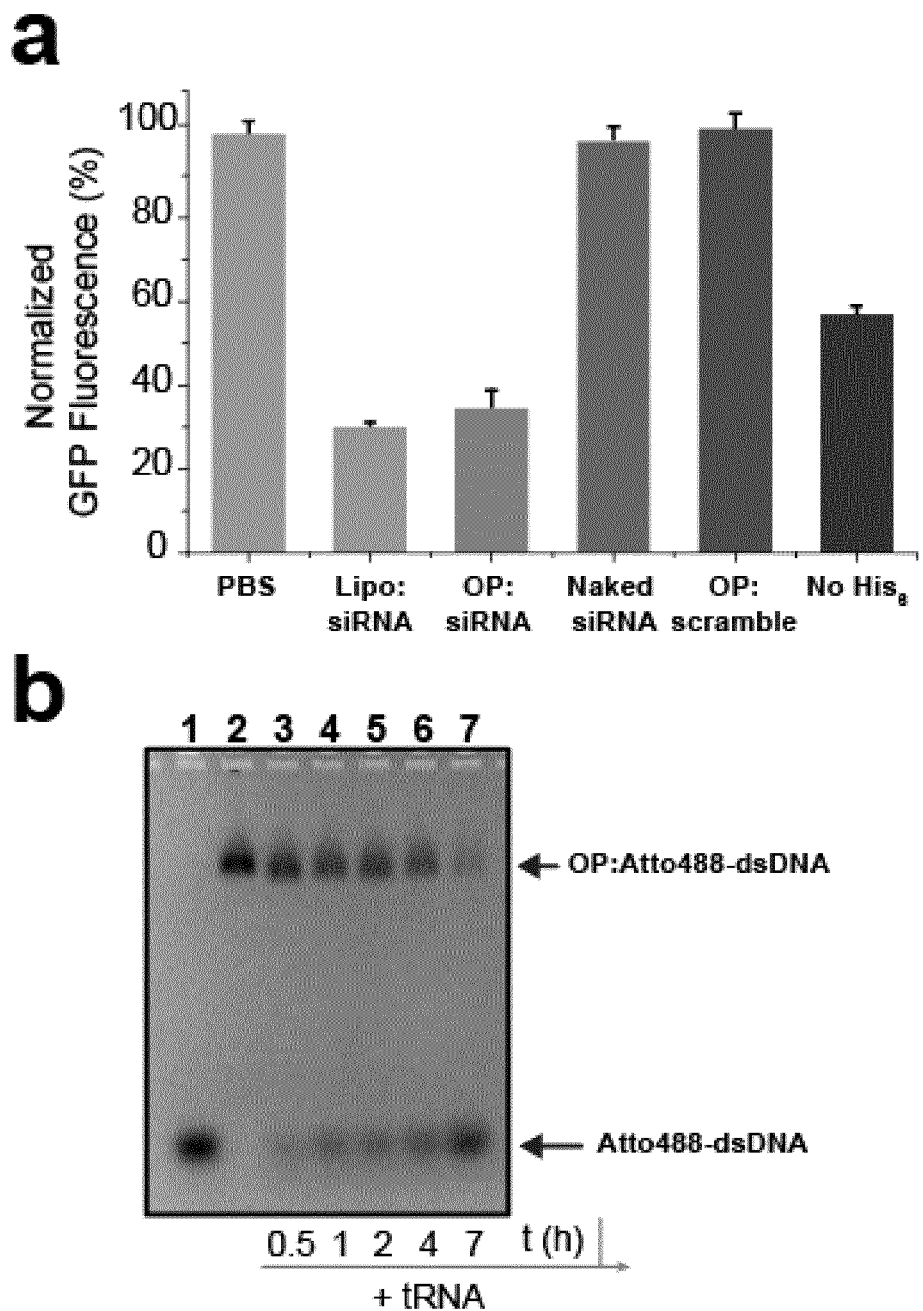
FIG. 4: (a) GFP knockdown determined by flow cytometry (n=4). OP:scramble refers to a scrambled siRNA which should not target the GFP mRNA, or any other endogenous sequences, and No His$_6$ refers to siRNA packaged in OP cages without His$_6$ tags. (b) Native AGE analysis of tRNA-induced release of dsDNA cargo from OP over time. Visualized by Atto488 fluorescence.

Firstly, the ability of OP to encapsulate tRNA was assayed by EMSA (FIG. 17). Samples were prepared with 20 pmol of tRNA (transfer RNA from wheat germ, Fluka, Germany) in 10 μL of PBS with and without OP (1.2 molar equiv.) and analyzed by native agarose gel stained with GelRed. The intracellular concentration of tRNA was calculated based on the average volume of a HeLa cell, the mass of RNA isolated from a single cell and the percentage of total RNA which is tRNA (Luby-Phelps, K. In International Review of Cytology, Eds. Walter, H., Brooks, D. E., Srere, P. A., Academic Press: 1999; Vol. 192, p 189-221; Lodish H, B. A., Zipursky SL In Molecular Cell Biology, 4th ed.; W.H. Freeman: New York, 2000). This estimate does not take into account the effect of molecular crowding within the cytoplasm, the relative fraction of free tRNA or other molecules which may also be encapsulated by OP. For the displacement assay, complexes (1:1 molar ratio) of OP with a duplex of Atto488-DNA were prepared by incubation in PBS at room temperature for 1 hour. Stocks were then divided into aliquots to provide samples for each gel lane. Each sample contained 10 pmol of OP/nucleic acid in a total volume of 10 μL PBS. Next, 2 μL of concentrated tRNA stock was added to samples at different time-points to give a final [tRNA] of 26 μM and samples were incubated at 37° C. The samples were then analyzed by native agarose gel, which was visualized by Atto488 fluorescence (FIG. 4b).

Serum Stability

Figure 22:
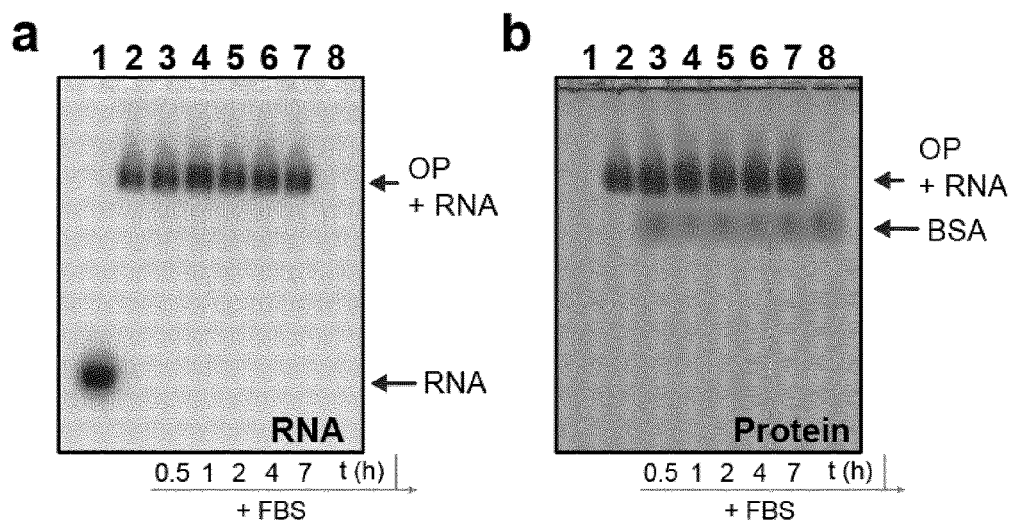
FIG. 22: Serum stability. The same native agarose gel stained with (a) GelRed for RNA and (b) Coomassie Blue for protein. Lower arrow: dsRNA, upper arrow: complex (nanoparticle plus dsRNA), middle arrow: BSA. There is no evident interaction of the dsRNA-loaded OP cage with serum proteins and no displacement or degradation of the RNA cargo. Lane 1—dsRNA, Lane 2—OP:dsRNA, Lanes 3-7—OP:dsRNA after incubation with 10% FBS at 37° C. for between 0.5, 1, 2, 4 and 7 hours, Lane 8-10% FBS only.
Figure 23:
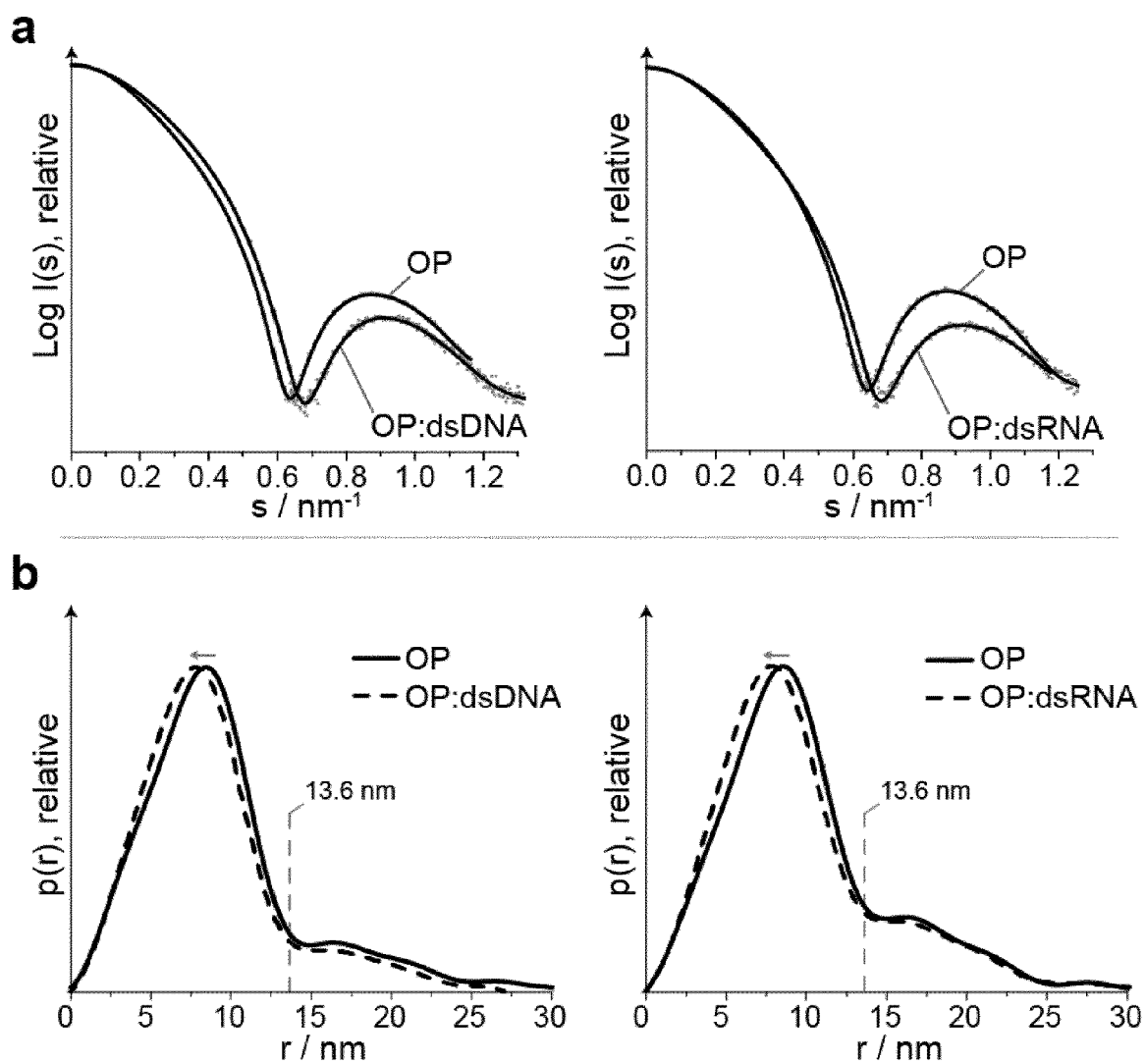
FIG. 23: Small angle X-ray scattering. (a) One-dimensional scattering curves for OP, OP:dsDNA and OP:dsRNA. Experimental data are shown as dots and the fits used to produce the distance distributions are shown as grey lines. (b) Pair distance distribution functions for OP, OP:dsDNA and OP:dsRNA calculated from the data above using AUTOGNOM.2-3 The dashed line corresponds to the particle diameter obtained from the DLS experiment (FIG. 8a), the tailing at distances above 14 nm is due to transient intermolecular interactions between individual protein cages. Upon complexation with oligonucleotides, there is no change in outer diameter of the protein cage and a shift in density from a hollow sphere-like particle towards a filled sphere. Both phenomena are consistent with internalization of the oligonucleotides inside the cavity of OP.
Figure 24:
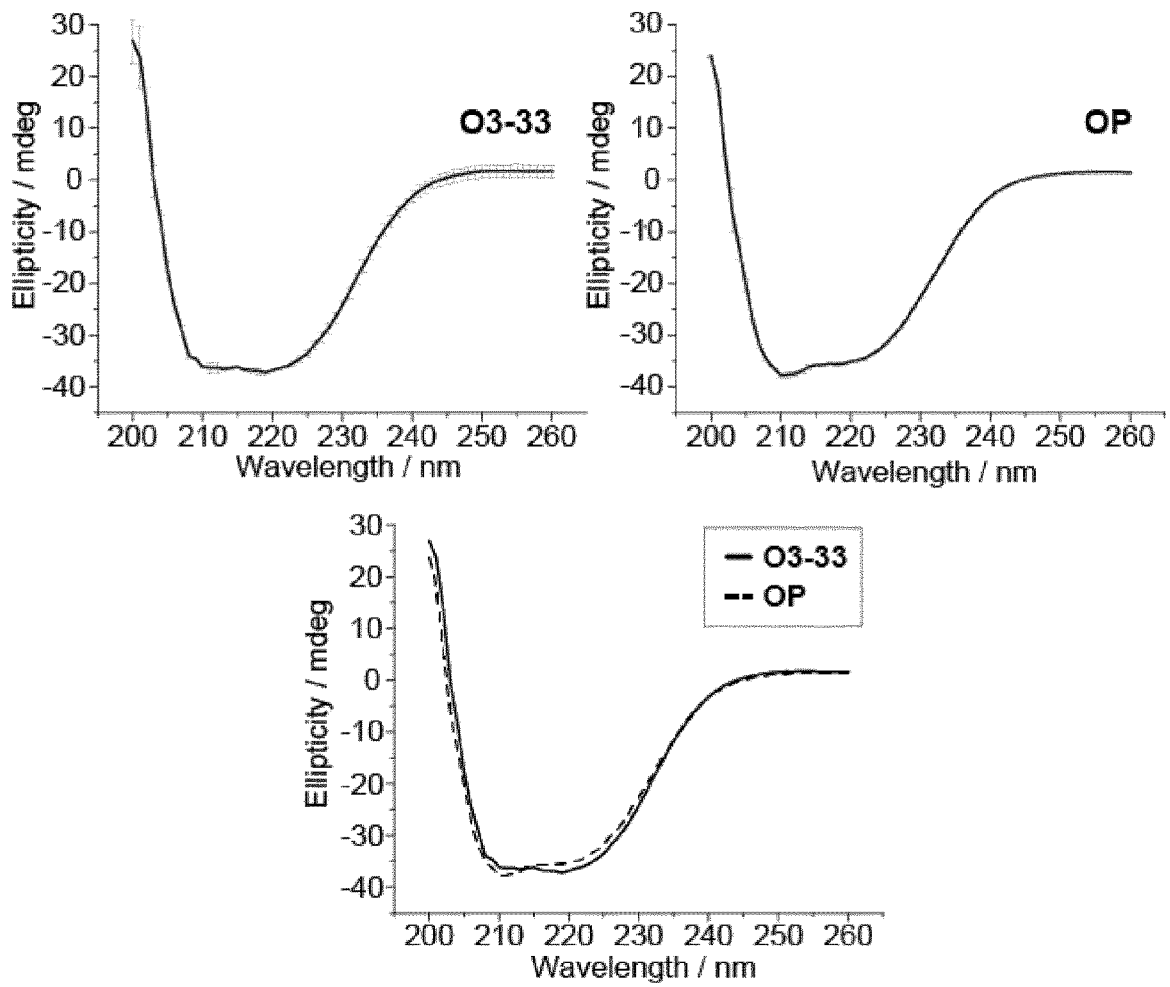
FIG. 24: Circular dichroism spectra for O3-33 and OP. Solid lines are mean values, and the error bar show the standard deviation from triplicate measurements of each protein.
Figure 25:
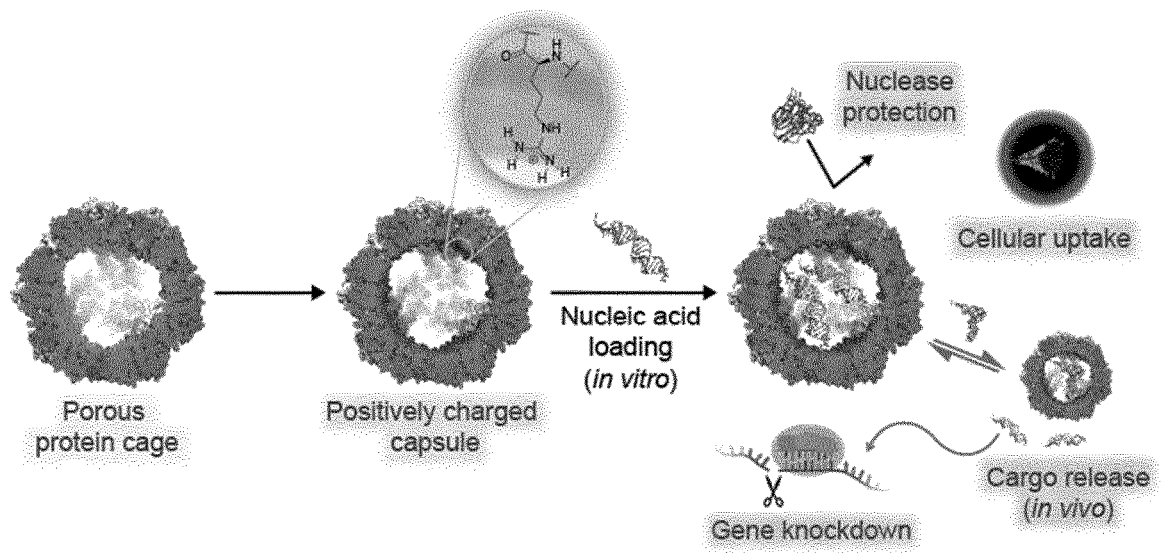
FIG. 25: Overview on preparation and utilization of the nanoparticle and complex of the invention.

Complexes (1:1 molar ratio) of OP with siRNA were prepared by incubation in PBS at room temperature for 1 hour. Stocks were then divided into aliquots to provide samples for each gel lane. Each sample contained 10 pmol of OP/nucleic acid in a total volume of 5 μL PBS. At different time points, 5 μL of 20% fetal bovine serum in PBS was added to samples and they were incubated at 37° C. The samples were then analyzed by native agarose gel, which was visualized by GelRed and Coomassie Blue (FIG. 22).

Small Angle X-Ray Scattering

SAXS data was obtained at beamline P12 of the PETRA-III synchrotron (DESY, Hamburg, Germany) where the X-ray wavelength was 1.24 Å. The Pilatus 1 M detector was positioned 2 m from the sample to collect a scattering vector range of 0.028-6.7 nm-1. Samples were measured at varying concentrations (between 0.5-5 mg/mL protein) in SAXS buffer (25 mM Tris-HCl buffer (pH 8.0), 200 mM NaCl, 5 mM EDTA and 10% glycerol) and the data from those which exhibited least aggregation and noise were used for further analysis. All samples were dialyzed against SAXS buffer to provide a well matched buffer blank. For OP:dsDNA and OP:dsRNA, protein cages were incubated overnight with 2 equivalents of duplex prior to dialysis against the SAXS buffer. Scattering curves were analyzed using PRIMUS16 and pair distance distributions were calculated using AUTOGNOM.

Dissociation of Double-Stranded DNA

For verifying that hpDNA does not dissociate, the fluorescence spectrum of 800 μL of 10 nM Atto488-hpDNA solution in PBS was measured from 450 nm to 600 nm. Subsequently, 50 nM OTR501 was added to each sample and the fluorescence decay was tracked over 600 seconds before another spectrum was recorded. The same procedure was applied to 10 nM solutions of dsDNA (Atto-488 ssDNA and Luc-g), 10 nM solution of dsDNA with 8 M urea, and a 10 nM solution of Atto-488 ssDNA and GFP-g.

Example 2—Protein and Nucleic Acid Sequences

Molecular weight (MW), isoelectropoint (pI), and extinction coefficient at 280 nm ($\varepsilon_{280}$, $M^{-1}$ $cm^{-1}$) of proteins were calculated using the SIB Bioinformatics Resource Portal tool (web.expasy.org/protparam/).

TABLE 1

Polypeptide sequences, their molecular weight (MW) and extinction coefficients at 280 nm ($\varepsilon_{280}$)

| Identity | Properties | Sequence |
|---|---|---|
| SEQ ID NO: 1 | 186 amino acids | MX$_{13}$QAIGILEL X$_1$SIAAGMELG DAMLKSAX$_{14}$VX$_{15}$ LLVSKTISX$_2$G KFLLMLGGDI X$_8$AIX$_9$X$_{12}$AIX$_{10}$TG TX$_{11}$QAGX$_3$LLVD SLVLAX$_{16}$IHPS VLPAIX$_{17}$GX$_{18}$NX$_{19}$ VX$_{20}$X$_7$X$_{21}$QAVGIV ETX$_4$SVAACIS AADX$_{22}$AVX$_{23}$GSX$_{24}$ VTLVRVHMAX$_5$ GIGGKCYMVV AGDVSDVALA VTVASSSAGA YGX$_6$LVYASLI PX$_{25}$PHX$_{26}$AMWX$_{27}$Q MVX$_{28}$GX$_{29}$E |
| OP SEQ ID NO: 2 | 192 amino acids MW = 20107 pI = 8.7 $\varepsilon_{280}$ = 10,095 | MSQAIGILELRSIAAGMELGDAMLKSANVDLLV SKTISRGKFLLMLGGDIGAIQQAIETGTSQAGRLL VDSLVLANIHPSVLPAISGLNSVDKRQAVGIVET RSVAACISAADRAVKGSNVTLVRVHMARGIGG KCYMVVAGDVSDVALAVTVASSSAGAYGRLV YASLIPRPHEAMWRQMVEGLEHHHHHH |
| OP-NoHis (no His6 tag) SEQ ID NO: 3 | 188 amino acids MW = 19428 pI = 8.7 $\varepsilon_{280}$ = 10095 | MSQAIGILELRSIAAGMELGDAMLKSANVDLLV SKTISRGKFLLMLGGDIGAIQQAIETGTSQAGRLL VDSLVLANIHPSVLPAISGLNSVDKRQAVGIVET RSVAACISAADRAVKGSNVTLVRVHMARGIGG KCYMVVAGDVSDVALAVTVASSSAGAYGRLV YASLIPRPHEAMWRQMVEGLEGS |
| OP-K93C SEQ ID NO: 4 | 192 amino acids MW = 20082 $\varepsilon_{280}$ = 10095 | MSQAIGILELRSIAAGMELGDAMLKSANVDLLV SKTISRGKFLLMLGGDIGAIQQAIETGTSQAGRLL VDSLVLANIHPSVLPAISGLNSVDCRQAVGIVET RSVAACISAADRAVKGSNVTLVRVHMARGIGG KCYMVVAGDVSDVALAVTVASSSAGAYGRLV YASLIPRPHEAMWRQMVEGLEHHHHHH |
| OP-cODC SEQ ID NO: 5 | 230 amino acids MW = 24178 $\varepsilon_{280}$ = 10220 | MSQAIGILELRSIAAGMELGDAMLKSANVDLLV SKTISRGKFLLMLGGDIGAIQQAIETGTSQAGRLL VDSLVLANIHPSVLPAISGLNSVDCRQAVGIVET RSVAACISAADRAVKGSNVTLVRVHMARGIGG KCYMVVAGDVSDVALAVTVASSSAGAYGRLV YASLIPRPHEAMWRQMVEGLEHHHHHHEFPPEV EEQDDGTLPMSCAQESGMDRHPAACASARINV |
| OTR101 SEQ ID NO: 6 | 192 amino acids MW = 20003 $\varepsilon_{280}$ = 15595 | MSQAIGILELTSIAAGMELGDAMLKSANVDLLV SKTISRGKFLLMLGGDIGAIQQAIETGTSQAGELL VDSLVLANIHPSVLPAISGLNSVDKRQAVGIVET WSVAACISAADRAVKGSNVTLVRVHMAFGIGG KCYMVVAGDVSDVALAVTVASSSAGAYGLLVY ASLIPRPHEAMWRQMVEGLEHHHHHH |
| OTR201 SEQ ID NO: 7 | 192 amino acids MW = 20012 $\varepsilon_{280}$ = 15595 | MSQAIGILELTSIAAGMELGDAMLKSANVDLLV SKTISRGKFLLMLGGDIGAIQQAIETGTSQAGELL VDSLVLANIHPSVLPAISGLNSVDKRQAVGIVET WSVAACISAADRAVKGSNVTLVRVHMARGIGG KCYMVVAGDVSDVALAVTVASSSAGAYGLLVY ASLIPRPHEAMWRQMVEGLEHHHHHH |

TABLE 1-continued

Polypeptide sequences, their molecular weight (MW) and extinction coefficients at 280 nm ($\varepsilon_{280}$)

| Identity | Properties | Sequence |
|---|---|---|
| OTR202 SEQ ID NO: 8 | 192 amino acids MW = 19969 $\varepsilon_{280}$ = 10095 | MSQAIGILELRSIAAGMELGDAMLKSANVDLLV SKTISPGKFLLMLGGDIGAIQQAIETGTSQAGELL VDSLVLANIHPSVLPAISGLNSVDKRQAVGIVET RSVAACISAADRAVKGSNVTLVRVHMAFGIGGK CYMVVAGDVSDVALAVTVASSSAGAYGLLVYA SLIPRPHEAMWRQMVEGLEHHHHHH |
| OTR203 SEQ ID NO: 9 | 192 amino acids MW = 20058 $\varepsilon_{280}$ = 15595 | MSQAIGILELRSIAAGMELGDAMLKSANVDLLV SKTISRGKFLLMLGGDIGAIQQAIETGTSQAGELL VDSLVLANIHPSVLPAISGLNSVDKRQAVGIVET WSVAACISAADRAVKGSNVTLVRVHMAFGIGG KCYMVVAGDVSDVALAVTVASSSAGAYGLLVY ASLIPRPHEAMWRQMVEGLEHHHHHH |
| OTR301 SEQ ID NO: 10 | 192 amino acids MW = 19966 $\varepsilon_{280}$ = 10095 | MSQAIGILELTSIAAGMELGDAMLKSANVDLLV SKTISPGKFLLMLGGDIGAIQQAIETGTSQAGELL VDSLVLANIHPSVLPAISGLNSVDKRQAVGIVET RSVAACISAADRAVKGSNVTLVRVHMARGIGG KCYMVVAGDVSDVALAVTVASSSAGAYGRLV YASLIPRPHEAMWRQMVEGLEHHHHHH |
| OTR302 SEQ ID NO: 11 | 192 amino acids MW = 19930 $\varepsilon_{280}$ = 15595 | MSQAIGILELRSIAAGMELGDAMLKSANVDLLV SKTISPGKFLLMLGGDIGAIQQAIETGTSQAGELL VDSLVLANIHPSVLPAISGLNSVDKRQAVGIVET WSVAACISAADRAVKGSNVTLVRVHMARGIGG KCYMVVAGDVSDVALAVTVASSSAGAYGLLVY ASLIPRPHEAMWRQMVEGLEHHHHH |
| OTR401 SEQ ID NO: 12 | 192 amino acids MW = 20037 $\varepsilon_{280}$ = 10095 | MSQAIGILELRSIAAGMELGDAMLKSANVDLLV SKTISRGKFLLMLGGDIGAIQQAIETGTSQAGELL VDSLVLANIHPSVLPAISGLNSVDKRQAVGIVET RSVAACISAADRAVKGSNVTLVRVHMARGIGG KCYMVVAGDVSDVALAVTVASSSAGAYGLLVY ASLIPRPHEAMWRQMVEGLEHHHHHH |
| OTR402 SEQ ID NO: 13 | 192 amino acids MW = 20039 $\varepsilon_{280}$ = 10095 | MSQAIGILELRSIAAGMELGDAMLKSANVDLLV SKTISPGKFLLMLGGDIGAIQQAIETGTSQAGRLL VDSLVLANIHPSVLPAISGLNSVDKRQAVGIVET RSVAACISAADRAVKGSNVTLVRVHMAFGIGGK CYMVVAGDVSDVALAVTVASSSAGAYGRLVY ASLIPRPHEAMWRQMVEGLEHHHHHH |
| OTR501 SEQ ID NO: 14 | 192 amino acids MW = 20048 $\varepsilon_{280}$ = 10095 | MSQAIGILELRSIAAGMELGDAMLKSANVDLLV SKTISPGKFLLMLGGDIGAIQQAIETGTSQAGRLL VDSLVLANIHPSVLPAISGLNSVDKRQAVGIVET RSVAACISAADRAVKGSNVTLVRVHMARGIGG KCYMVVAGDVSDVALAVTVASSSAGAYGRLV YASLIPRPHEAMWRQMVEGLEHHHHHH |
| OTR502 SEQ ID NO: 15 | 192 amino acids MW = 20137 $\varepsilon_{280}$ = 15595 | MSQAIGILELRSIAAGMELGDAMLKSANVDLLV SKTISRGKFLLMLGGDIGAIQQAIETGTSQAGRLL VDSLVLANIHPSVLPAISGLNSVDKRQAVGIVET WSVAACISAADRAVKGSNVTLVRVHMARGIGG KCYMVVAGDVSDVALAVTVASSSAGAYGRLV YASLIPRPHEAMWRQMVEGLEHHHHHH |
| OTR503 SEQ ID NO: 16 | 192 amino acids MW = 20064 $\varepsilon_{280}$ = 10095 | MSQAIGILELRSIAAGMELGDAMLKSANVDLLV SKTISRGKFLLMLGGDIGAIQQAIETGTSQAGRLL VDSLVLANIHPSVLPAISGLNSVDKRQAVGIVET RSVAACISAADRAVKGSNVTLVRVHMARGIGG KCYMVVAGDVSDVALAVTVASSSAGAYGLLVY ASLIPRPHEAMWRQMVEGLEHHHHHH |
| cODC SEQ ID NO: 17 | 38 amino acids MW = 4089 $\varepsilon_{280}$ = 125 | EFPPEVEEQDDGTLPMSCAQESGMDRHPAACAS ARINV |
| OP-His3 SEQ ID NO: 37 | 192 amino acids MW = 19696 $\varepsilon_{280}$ = 10,095 | MSQAIGILELRSIAAGMELGDAMLKSANVDLLV SKTISRGKFLLMLGGDIGAIQQAIETGTSQAGRLL VDSLVLANIHPSVLPAISGLNSVDKRQAVGIVET RSVAACISAADRAVKGSNVTLVRVHMARGIGG KCYMVVAGDVSDVALAVTVASSSAGAYGRLV YASLIPRPHEAMWRQMVEGLEHHH |

TABLE 1-continued

Polypeptide sequences, their molecular weight (MW) and extinction coefficients at 280 nm ($\varepsilon_{280}$)

| Identity | Properties | Sequence |
|---|---|---|
| OP-His9 SEQ ID NO: 38 | 192 amino acids MW = 20519 $\varepsilon_{280}$ = 10,095 | MSQAIGILELRSIAAGMELGDAMLKSANVDLLV SKTISRGKFLLMLGGDIGAIQQAIETGTSQAGRLL VDSLVLANIHPSVLPAISGLNSVDKRQAVGIVET RSVAACISAADRAVKGSNVTLVRVHMARGIGG KCYMVVAGDVSDVALAVTVASSSAGAYGRLV YASLIPRPHEAMWRQMVEGLEHHHHHHHHH |

SDS-PAGE and Coomassie blue visualization showed different mobilities that arose from the different mobilities of the proteins OP and OTR101 to OTR503. This proofs that all proteins have the same weight of about 20 kDa, and that all variants are decently pure.

TABLE 2

Oligonucleotide sequences

Figure 21:
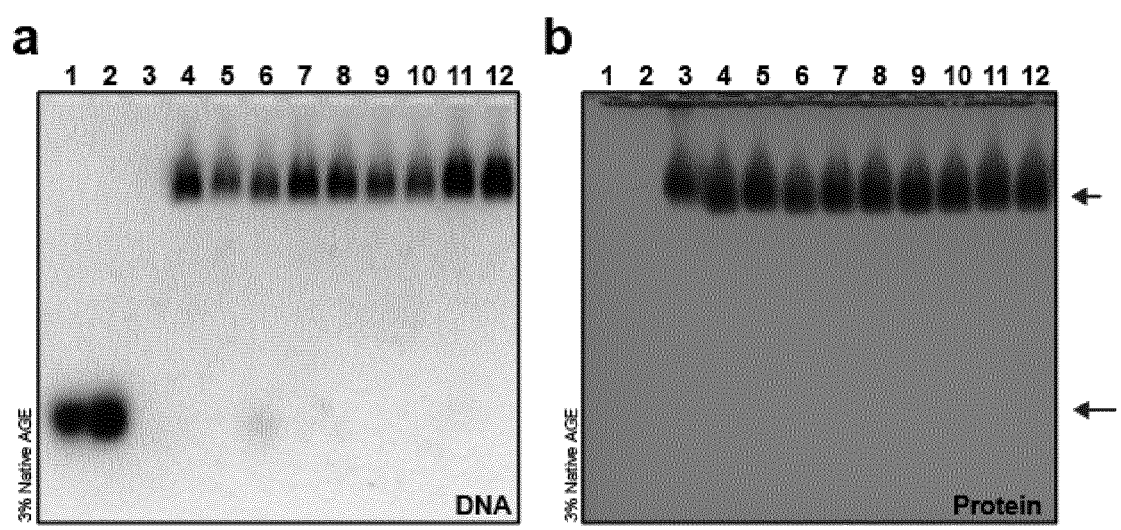
FIG. 21: Loading of different DNA sequences. The same native agarose gel (3% native AGE) stained with (a) GelRed for DNA and (b) Coomassie Blue for protein. Lower arrow: ssDNA, upper arrow: complex (nanoparticle plus ssDNA, dsDNA, dsRNA). Each sample contains a 2:1 ratio of ssDNA to capsid, where the oligonucleotides range from 18-26 nt with random sequences (provided in Table 2 below). Lane 1—18 nt ssDNA1, Lane 2—26 nt ssDNA, Lane 3—OP, Lanes 4-12—OP+2 equiv. of the different ssDNAs.

| Identity | SEQ ID NO: | Sequence | |
|---|---|---|---|
| A488-DNA | 18 | A488* TTAATTAAAGACTTCAAGCGG | Used in all assays where a fluorescent DNA probe is present |
| A488-DNA' | 19 | GCTTGAAGTCTTTAATTAATT | Complement for A488-DNA |
| GFP-g | 20 | GAACTTCAGGGTCAGCTTGGG | EMSA, displacement DNA for $k_{off}$ determination |
| GFP-p | 21 | CAAGCTGACCCTGAAGTTCTT | EMSA, displacement DNA for $k_{off}$ determination |
| GFP-siRNA-g | 22 | gaacttcagggtcagcttgGG | EMSA, nuclease stability assay, GFP knockdown |
| GFP-siRNA-p | 23 | caagctgaccctgaagttcTT | EMSA, nuclease stability assay, GFP knockdown |
| siRNA scramble-g | 24 | uaaggcuaugaagagauacTT | GFP knockdown |
| siRNA scramble-p | 25 | gua ucu uu cau agc cuu aTT | GFP knockdown |
| GSstopfw | 26 | TCGAGGGCAGCTAATGAG | GS** cassette for cloning OP without a His6 tag |
| GSstoprv | 27 | TGCACTCATTAGCTGCCC | GS** cassette for cloning OP without a His6 tag |
| ssDNA1 | 28 | CGTGGCGAGCAGCAGCGC | FIG. 21(12) (Lane 4) |
| ssDNA2 | 29 | CCTGGTGCGTGTGCACATGG | FIG. 21(12) (Lane 5) |
| ssDNA3 | 30 | GTGCTCGAGACCTTCCACCATC | FIG. 21(12) (Lane 6) |
| ssDNA4 | 31 | GGTGATGCGATGCTGAAAAGCGC | FIG. 21(12) (Lane 7) |
| ssDNA5 | 32 | GCGATTCAGCAGGCGATTGAAACC | FIG. 21(12) (Lane 8) |
| ssDNA6 | 33 | CGATTAGCGGTCTGAATAGCGTGG | FIG. 21(12) (Lane 9) |

TABLE 2-continued

Oligonucleotide sequences

| Identity | SEQ ID NO: | Sequence | | |
|---|---|---|---|---|
| ssDNA7 | 34 | GGTTTCAATCGCCTGCTGAATCGC | FIG. 21(12) | (Lane 10) |
| ssDNA8 | 35 | CCACGCTATTCAGACCGCTAATCG | FIG. 21(12) | (Lane 11) |
| ssDNA9 | 36 | GAAGGAGATATACATATGAGCCAGGC | FIG. 21(12) | (Lane 12) |

Uppercase letters denote deoxy- and lowercase denote ribonucleotides, respectively. A488 refers to the fluorophore Atto488 phosphoramidite, which is coupled during solid-phase synthesis.

Example 3—Structural Characterization of the Nanoparticle

As a starting scaffold, the inventors chose O3-33, a self-assembling protein cage computationally designed by Baker and co-workers (King, N. P. et al., Computational Design of Self-Assembling Protein Nanomaterials with Atomic Level Accuracy. Science 2012, 336, 1171-1174), which is anon-functional protein cage and a naïve computationally designed scaffold without the ability to encapsulate or deliver macromolecules intracellularly.

Figure 1:
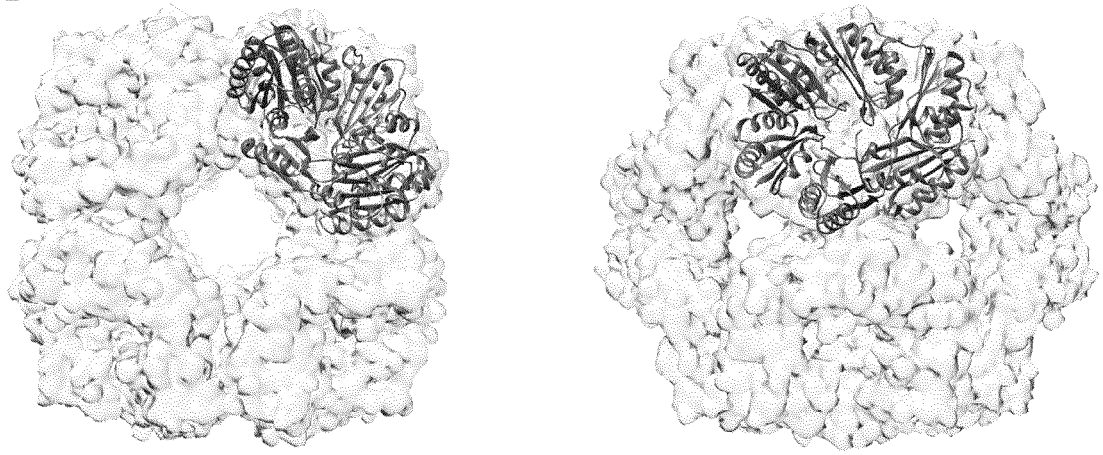
FIG. 1: (a) Surface models of the OP cage from 4-fold and 2-fold symmetry axes, with one trimer shown in ribbon form. Model generated from X-ray diffraction data. (b) Side view of one trimer with arginine insertion positions shown as black spheres. (c) Lumenal surface of a trimer with arginine positions shown as black spheres. (d) Negative stain transmission electron micrograph (TEM) of OP.
Figure 1:
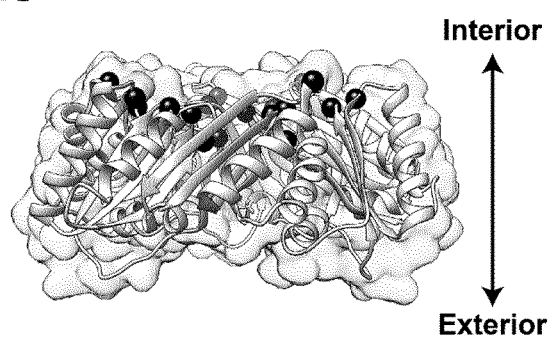
Figure 1:
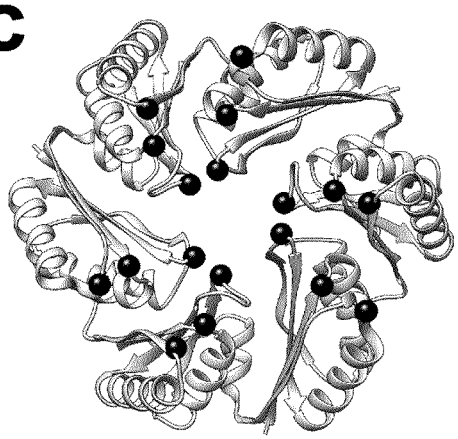
Figure 1:
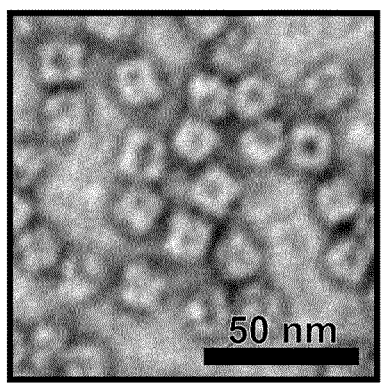
Figure 5:
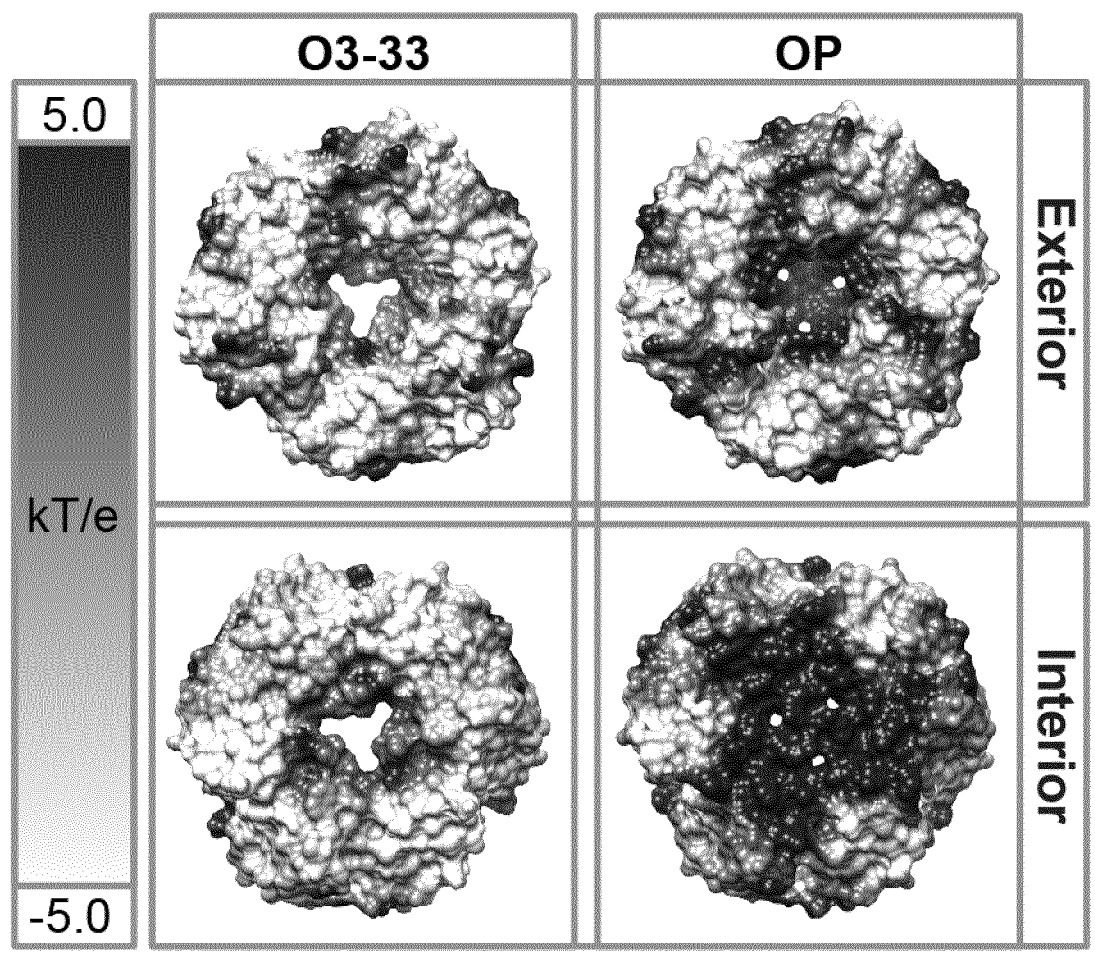
FIG. 5: Electrostatic potential surfaces. Coulombic surface comparison of trimer subunits from the crystal structures of O3-33 and OP, showing both inner and outer surfaces.
Figure 6:
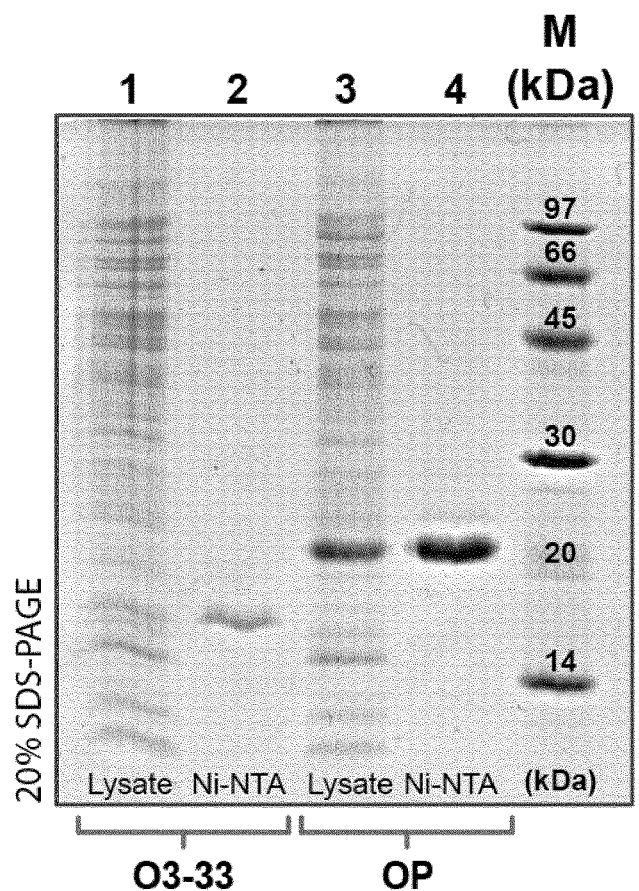
FIG. 6: SDS-PAGE. Both proteins from the crude cell lysate and products isolated from Ni-NTA are shown. The lower mobility of OP is due to the additional positively charged amino acids rather than a difference in molecular weight. The faint band above OP is removed after size-exclusion chromatography. Gel visualized with Coomassie Blue. Typical yields for OP protein after Ni-NTA are 100 mg/L of E. coli culture.

In order to allow cargo loading, the inventors introduced binding interactions to O3-33. Amino acids Thr11, Pro39, Glu66, Trp103, Phe130 and Leu163 were replaced with arginine to create an O3-33 variant, referred herein as OP, which has a highly positively charged interior cavity (FIGS. 1b, 5). The OP protein can be overexpressed in E. coli cells and isolated by Ni-NTA affinity chromatography through a C-terminal His6 tag (FIG. 6). Due to the highly positively charged interior cavity, there was significant contamination from endogenous E. coli RNA. However, these RNA contaminations were easily removed with high ionic strength buffer to weaken electrostatic interactions and RNase A to digest contaminant RNA (see Material & Methods, Cell lysis, Ni-NTA and RNA removal for OP).

Figure 7:
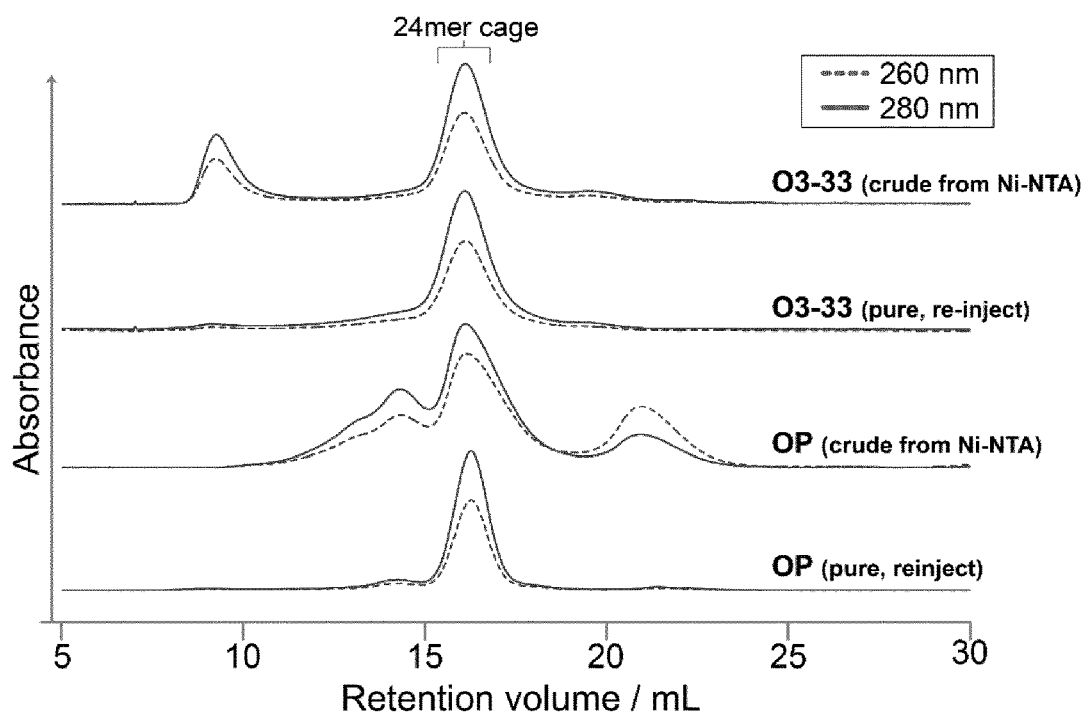
FIG. 7: SEC of O3-33 and OP. Size exclusion chromatography of O3-33 and positively charged cage-like nanoparticles, OP, of the invention. Both the crude mixtures from Ni-NTA chromatography and analytical traces of the purified assemblies are shown. Dotted lines correspond to absorbance at 260 nm (nucleic acid), and solid lines to absorbance at 280 nm (protein). Based on TEM analysis, the peaks at 12-14 mL for OP (Ni-NTA) contain dimer, timer and higher order aggregates of fully assembled cages rather than alternative quaternary assemblies. The peak at 22 mL for OP (Ni-NTA) contains nucleic acid fragments that were loaded during protein expression in E. coli and that were easily removed by SEC. The main peak at 16 mL shows the eluted fractions of the protein that were collected and further characterized. SEC of OP is representative, and OTR101 to OTR503 show a comparable elution volume around 16 mL.
Figure 8:
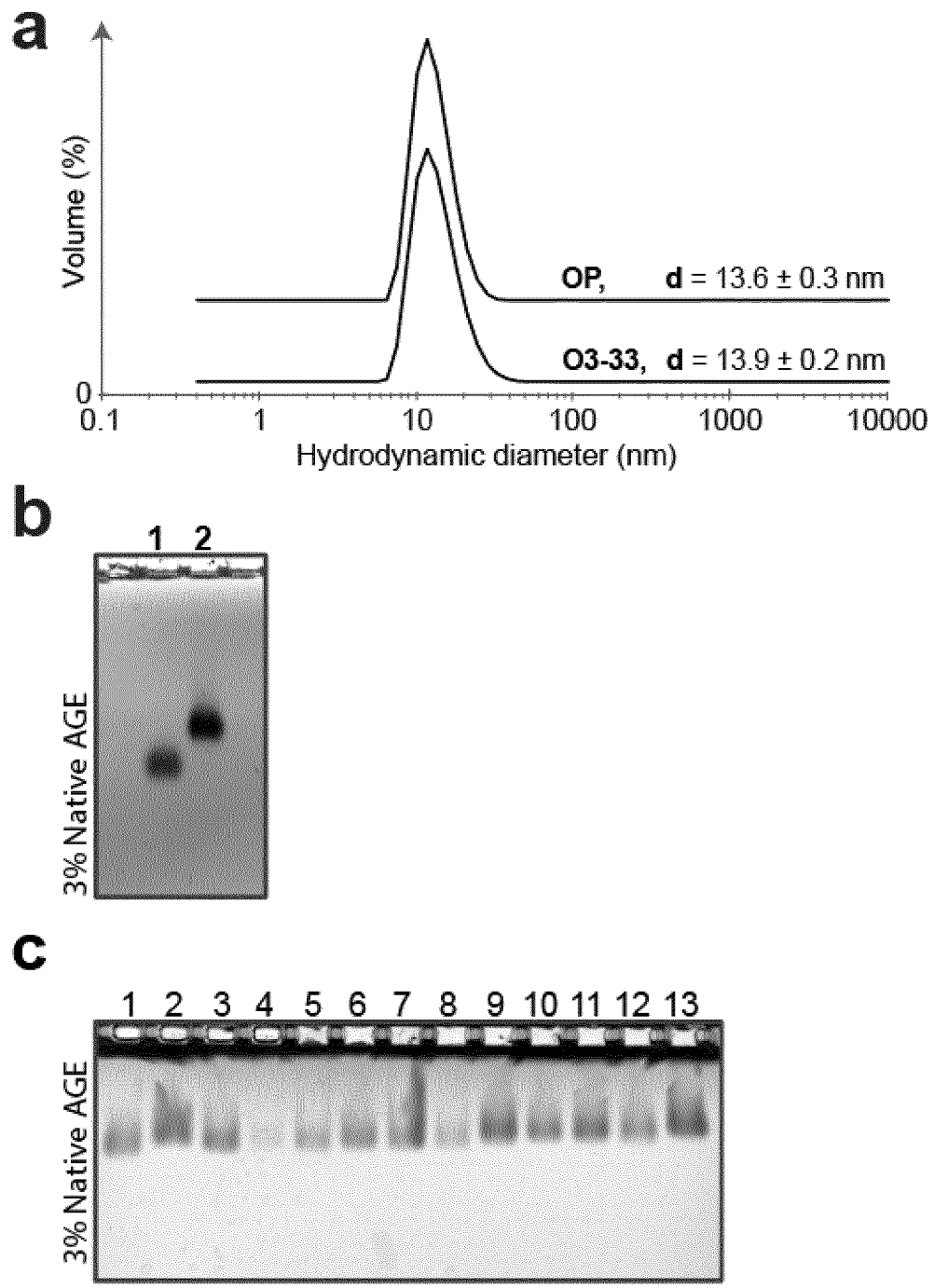
FIG. 8: DLS and AGE of O3-33 and OP (a) Dynamic light scattering (DLS) of original (O3-33) and positively charged (OP) cage variants. (b) Native agarose gel electrophoresis (AGE) (3%); Lane 1: O3-33, Lane 2: OP, stained with Coomassie Blue. Given the SEC, DLS, TEM and X-ray diffraction data, the decreased mobility of OP compared to O3-33 is due to the increased positive charge rather than a change in size. (c) 3% AGE of OP variants, stained with Coomassie Blue for protein. Differences in mobility are due to overall charge rather than change in size. The smearing is caused by the high amount of protein loaded, and not from degradation of the cage. Lane 1: O3-33. Lane 2: OTR101. Lane 3: OTR201. Lane 4: OTR202. Lane 5: OTR203. Lane 6: OTR301. Lane 7: OTR302. Lane 8: OTR401. Lane 9: OTR402. Lane 10: OTR501. Lane 11: OTR502. Lane 12: OTR503. Lane 13: OP. All proteins have comparable electrophoretic mobility; slight deviations are caused by the increased number of positively charged arginine residues, since both SEC and TEM show that the particles have the same size. Together, these characterization approaches support the hypothesis that the structure of all variants is the same as for OP.
Figure 9:
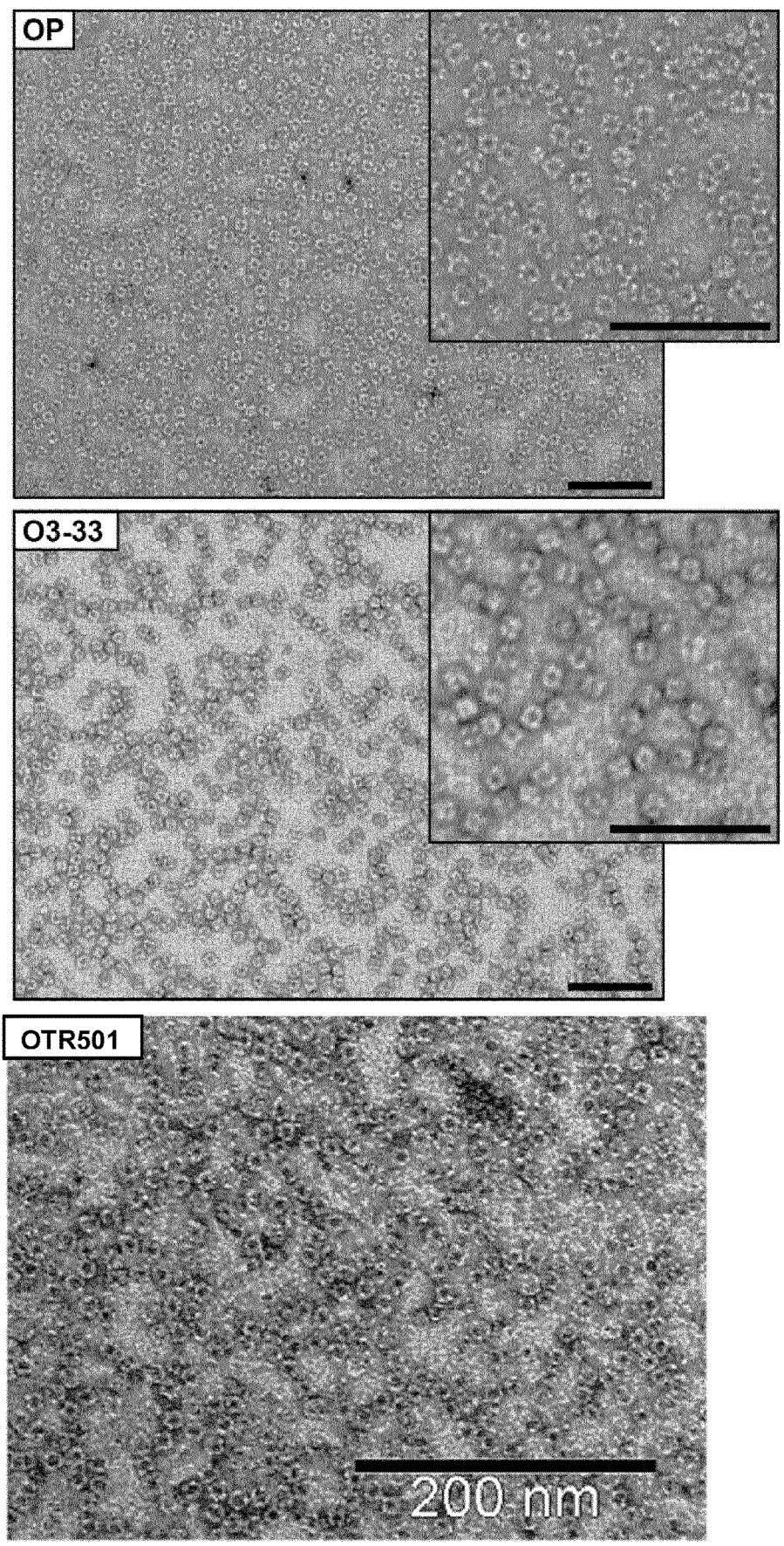
FIG. 9: Transmission electron microscopy (TEM) images. Scale bars for OP and O3-33 are 100 nm, and 200 nm for OTR501. Negatively stained transmission electron microscopy images were obtained for OP and OTR101 to OTR503. SEC shown herein are representative for OP and all variants OTR101 to OTR503. These images suggest a uniform distribution of the variant's capsid and morphology consistent with OP.

The ability of OP to form the desired cage-like quaternary structure (FIG. 1a) was assessed by size-exclusion chromatography (SEC), dynamic light scattering (DLS) and native agarose gel electrophoresis (AGE) (FIGS. 7, 8). All data were consistent with the formation of an assembly with the same size as O3-33 cage. Furthermore, OP and O3-33 were indistinguishable by TEM (FIGS. 1c, 9), and X-ray diffraction confirmed that the addition of 144 arginines to the ~8 nm diameter cavity had negligible effect on monomer fold and cage structure (FIG. 1d). Root-mean square deviations were 0.5-0.7 Å for all Cα atoms of each monomer.

Furthermore, characterization of the OP variants OTR101 to OTR503 by SEC, AGE and TEM showed that the structure of all OP variants is the same as for OP.

Example 4—Nucleic Acid Cargo Loading

Figure 10:
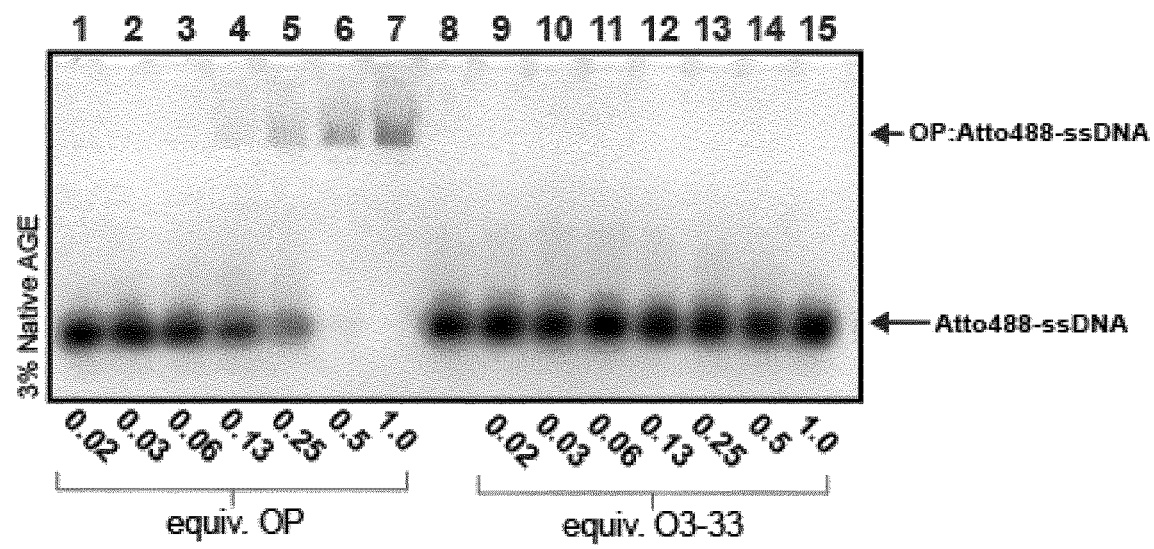
FIG. 10: EMSA of O3-33 and OP with ssDNA. Electrophoretic mobility shift assay of Atto488-labelled ssDNA with increasing equivalents of OP or O3-33. Lanes 1-7: Atto488-ssDNA+OP, Lane 8: Atto488-ssDNA; Lanes 9-15: Atto488-ssDNA+O3-33. Gel visualized by Atto488 fluorescence.
Figure 11:
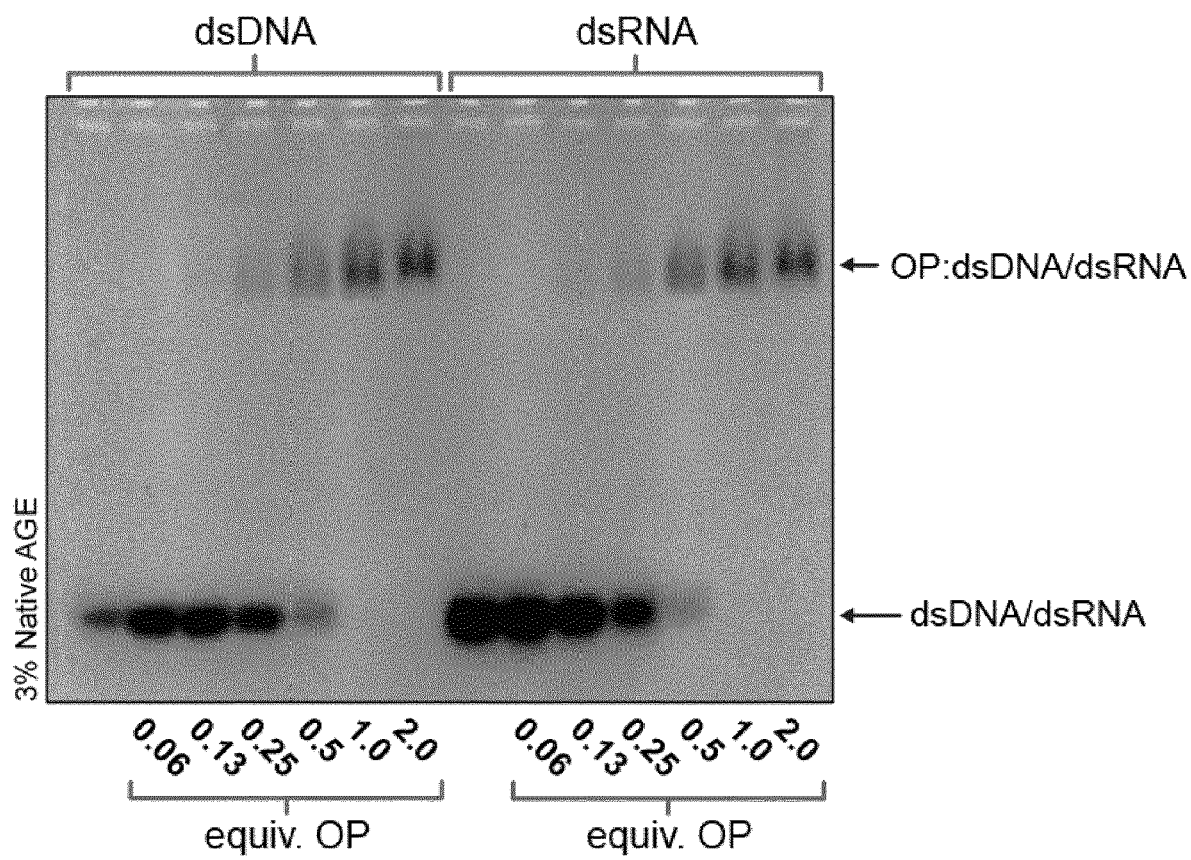
FIG. 11: EMSA of OP with dsDNA and dsRNA. Electrophoretic mobility shift of (a) dsDNA and (b) dsRNA with increasing molar equivalents of OP cage, both 21 bp in length. The faint band of free nucleic acid at 0.5 equivalents of OP are due to the non-equilibrium conditions during electrophoresis and represents a small fraction of the total nucleic acid. As there are 144 arginine residues per capsid, charge neutrality would be achieved upon encapsulation of only 144 nucleotides, which equates to 3.6 duplexes (21 bp) per capsid. The maximum loading capacity of two duplexes observed here can be rationalized in terms of RNA-RNA charge repulsion, the physical constraints imposed by the spherical container, and the requirement for accessible arginine residues to contribute favorable binding interactions. Stained for nucleic acid with GelRed.
Figure 12:
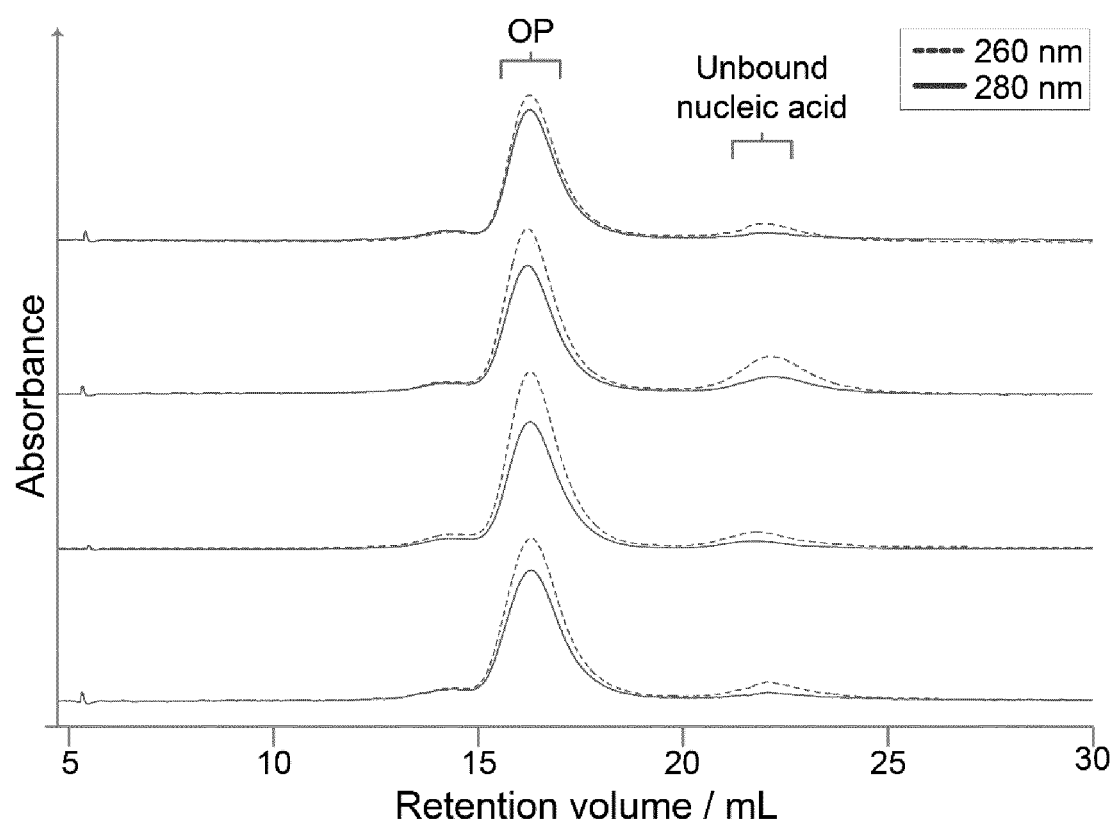
FIG. 12: SEC of nucleic acid encapsulation. Size exclusion chromatography of empty OP cage compared to OP after incubation with 5 equivalents per cage of either ssDNA, dsDNA or dsRNA (all 21 nt in length). Dotted lines correspond to absorbance at 260 nm (nucleic acid), and solid lines to absorbance at 280 nm (protein). No nucleic acid-mediated aggregation is observed. All complexes exhibit the same retention volume as the empty OP cage, but with an increased A260/A280 ratio, indicating internalization of the oligonucleotides.

With the structural integrity of the empty protein cage established, nucleic acid cargo loading was investigated in vitro. DNA and RNA duplexes, which are 2 nm in diameter, are able to pass through the ~3.5 nm diameter pores, allowing encapsulation. An electrophoretic mobility shift assay (EMSA) revealed that the parent O3-33 cage had no effect on the electrophoretic mobility of Atto488-ssDNA, a 21 nt Atto488-labeled single-stranded (ss) DNA (FIG. 10). In contrast, co-localization of protein and DNA bands was observed for OP (FIG. 2a). The binding of double-stranded (ds) DNA and dsRNA with OP was also assessed (FIG. 11), providing results analogous to ssDNA. In all cases, near complete binding of the oligo-nucleotides was observed upon addition of 0.5 equivalents of OP, suggesting two guests per cage. This stoichiometry was confirmed from the $A_{26}/A_{280}$ ratio of SEC-purified complexes of OP with ssDNA, dsDNA or dsRNA (FIGS. 2b and 12, Table 3).

TABLE 3

Absorbance of SEC-purified OP:nucleic acid complexes and calculated number of guests per cage

| Sample | $A_{260}/A_{280}$ ratio | Guests per cage |
|---|---|---|
| OP | 0.64 | —/— |
| OP:ssDNA | 1.21 | 2.05 |
| OP:dsDNA | 1.29 | 1.98 |
| OP:dsRNA | 1.40 | 1.97 |

Example 5—Binding Kinetics

Figure 13:
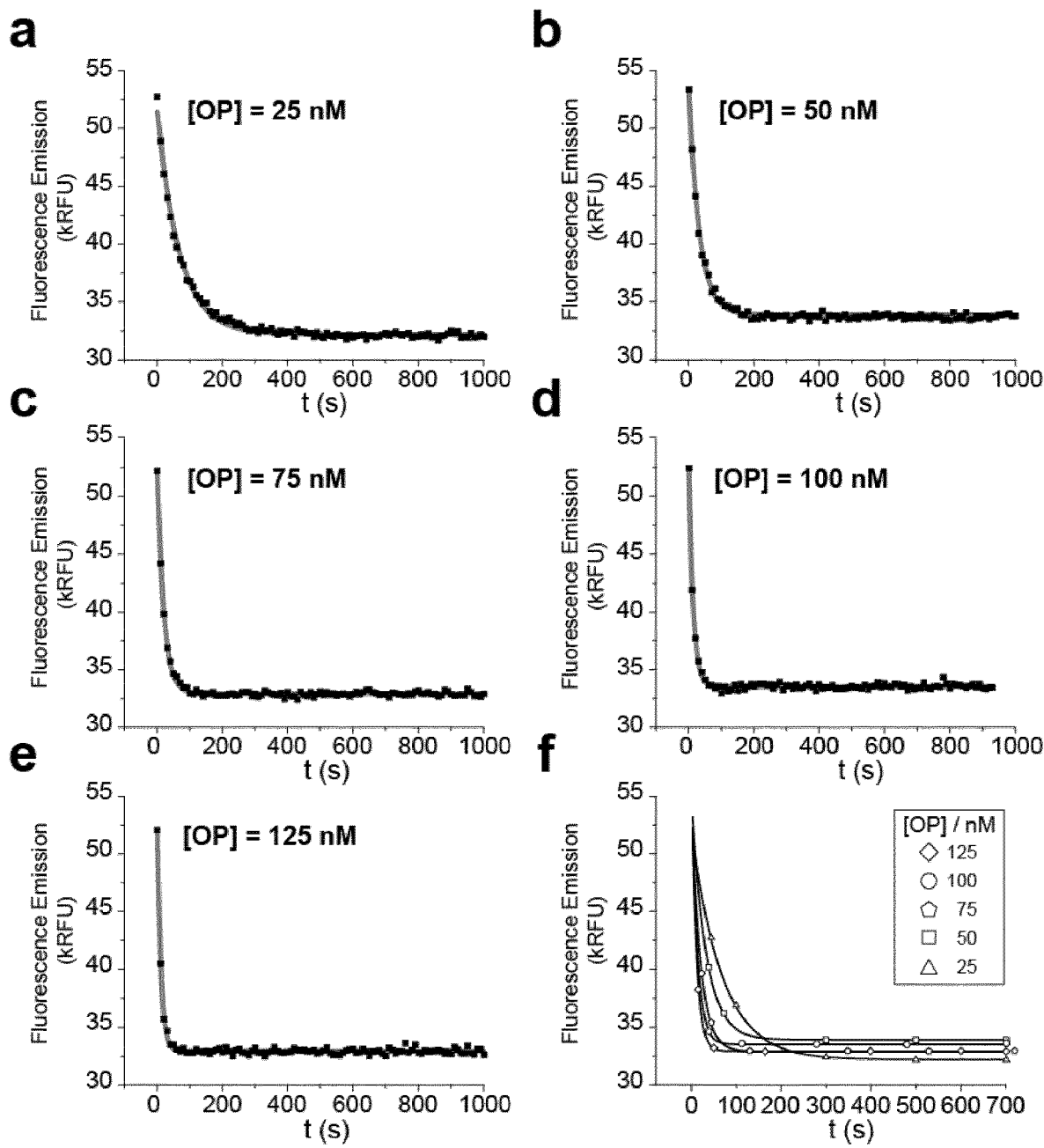
FIG. 13: Kinetic measurements. A representative dataset for determining the 1:1 encapsulation kinetics of ssDNA in OP cages. As evident from the band intensities seen in the EMSA (FIG. 10), encapsulation of Atto488-ssDNA by OP results in quenching of the fluorophore, which was exploited for the time-resolved binding assays shown here. The Atto488 fluorophore was excited at 488 nm and emission was measured at 515 nm. In each experiment (a-e) the concentration of Atto488-ssDNA is 10 nM and the concentration of OP added at t=0 is shown on the plot. (f) Comparison, without any normalization, of the single exponential fits (shown in a-e) for these five concentration points.

Encapsulation-induced fluorescence quenching of the DNA-conjugated fluorophore Atto488 was used to determine binding kinetics by fluorimetry (FIG. 13). The association rate constant, $k_{on}=(6.6\pm0.6)\times10^5$ $M^{-1}s^{-1}$ (FIG. 2c) and dissociation rate constant, $k_{off}=(1.6\pm0.1)\times10^{-4}$ $s^{-1}$ (FIG. 2d) were used to calculate a dissociation constant, Kd= $(2.4\pm0.3)\times10^{-10}$ M, for this protein-DNA complex. This Kd value is two orders of magnitude lower than those reported for RNA-protein interactions in viruses ($10^{-8}$-$10^{-7}$ M) and in the range of the tightest binding transcription factors ($10^{-15}$-$10^{-10}$ M). It must be noted that a crucial difference in this artificial system is the lack of sequence specificity, which is advantageous for a delivery device, as it allows packaging of any desired nucleotide sequence, and oligo-nucleotide chemical modifications that retain negative charge.

An important role of any nucleic acid delivery system is to protect its cargo from nuclease degradation. As such, digestion assays with three nucleases were conducted: DNase I (30 kDa), RNase A (14 kDa) and benzonase50 (60 kDa). AGE (FIG. 14) revealed protection from the larger enzymes. Only RNase A was able to enter the cage and digest the cargo. These nuclease assay data corroborate the kinetic studies suggesting that guests are tightly bound in the inner cavity with a negligible dissociation rate.

Figure 15:
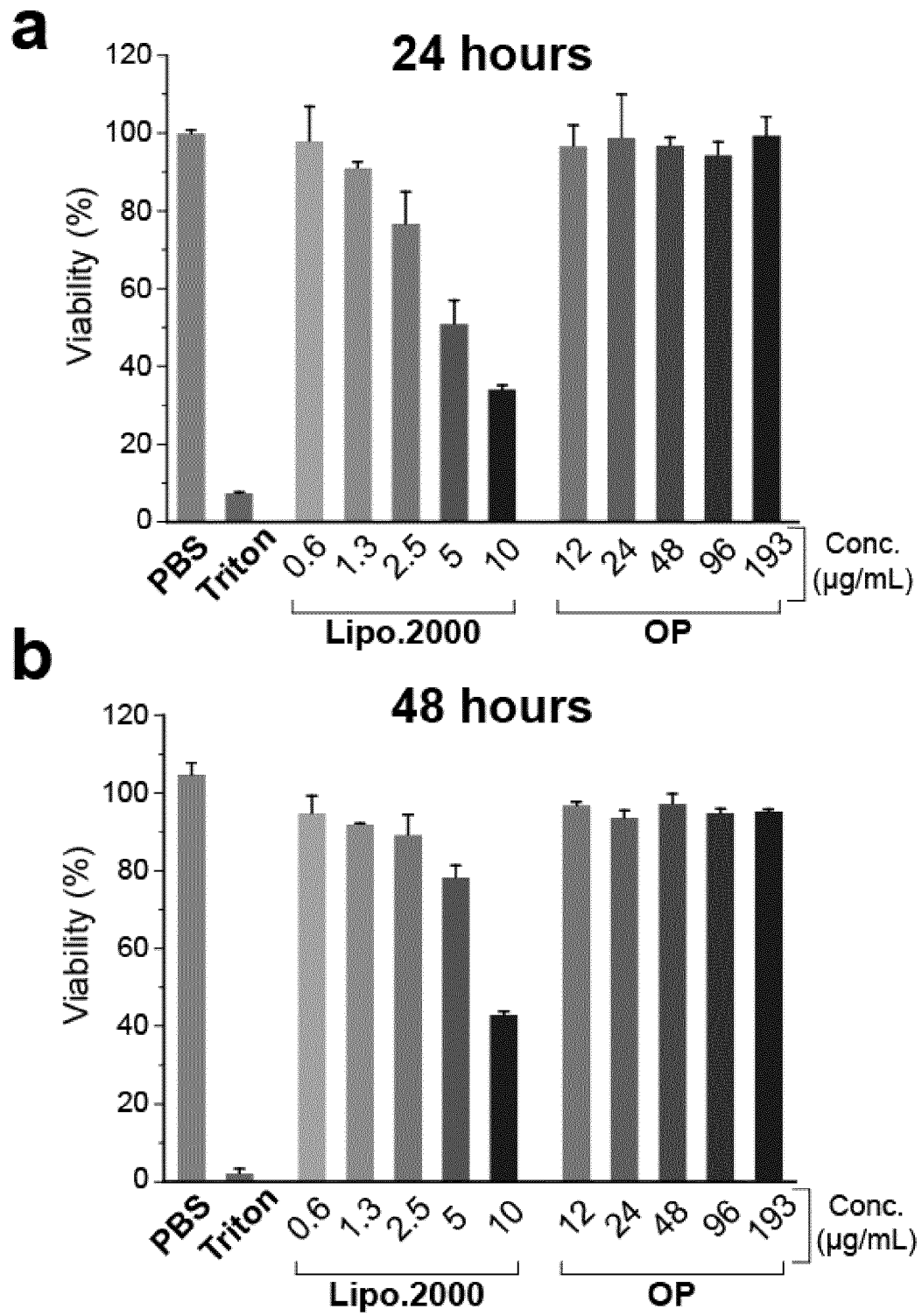
FIG. 15: Cytotoxicity of OP and Lipofectamine 2000 at various concentrations in HeLa cells after (a) 24 hour and (b) 48 hour incubation. Controls: PBS or 1% Triton X-100 surfactant (n=3).

With many nucleic acid delivery vectors, such as cationic lipids and polymers, a compromise must be made between transfection efficiency and cytotoxicity. In vitro cytotoxicity was measured in HeLa cells over 24 hours using WST-8 to quantify dehydrogenase activity (FIG. 15, Table 6). OP showed negligible toxicity up to 400 nM cage (193 µg/mL protein). These results compare favorably with the commonly used transfection reagent Lipofectamine 2000, a cationic lipid, which reduced cell viability to 35%-45% at 19-fold lower concentrations by mass (10 µg/mL) under assay conditions described above.

TABLE 6

Cytotoxicity of OP and Lipofectamine 2000 at various concentrations in HeLa cells

| Sample | Concentration (µg/mL) | Viability (%) |
| --- | --- | --- |
| PBS | n/a | 100.0 ± 0.8 |
| Triton | n/a | 7.4 ± 0.2 |
| Lipofectamine | 0.6 | 98.1 ± 8.7 |
| Lipofectamine | 1.3 | 91.2 ± 1.4 |
| Lipofectamine | 2.5 | 76.8 ± 8.1 |
| Lipofectamine | 5 | 51.0 ± 5.9 |
| Lipofectamine | 10 | 34.2 ± 0.9 |
| OP | 12 | 96.7 ± 5.4 |
| OP | 24 | 99.0 ± 10.9 |
| OP | 48 | 96.9 ± 2.0 |
| OP | 96 | 94.6 ± 3.2 |
| OP | 193 | 99.5 ± 4.8 |

Example 6—Cellular Uptake and Cargo Release

Figure 3A:
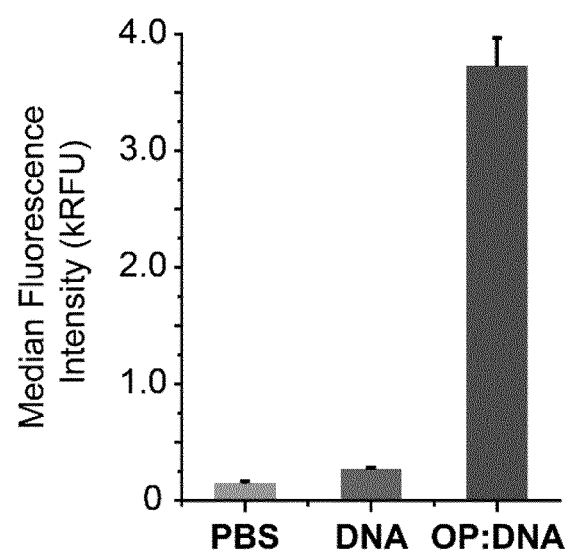
FIG. 3: (a) Cellular uptake of Atto488-DNA with or without OP, determined by flow cytometry (n=3). (b) Confocal fluorescence microscopy of HeLa cells treated with Atto488-DNA or OP:Atto488-DNA (OP with Atto488-ssDNA cargo). Hoechst refers to nuclear staining. (c) Flow cytometry analysis of cellular uptake across different cell lines. Median fluorescence intensities of seven different cell types after treatment with 200 nM of Atto488-DNA or OP:Atto488-DNA for 18 hours. Median fluorescence intensities were obtained from 10,000 cells. MCF-7—breast cancer, HepG2—liver cancer, A431—skin cancer, HT-29—colon cancer, CHO-K1—hamster ovary (non-cancerous), Vero—African green monkey kidney (non-cancerous).
Figure 3B:
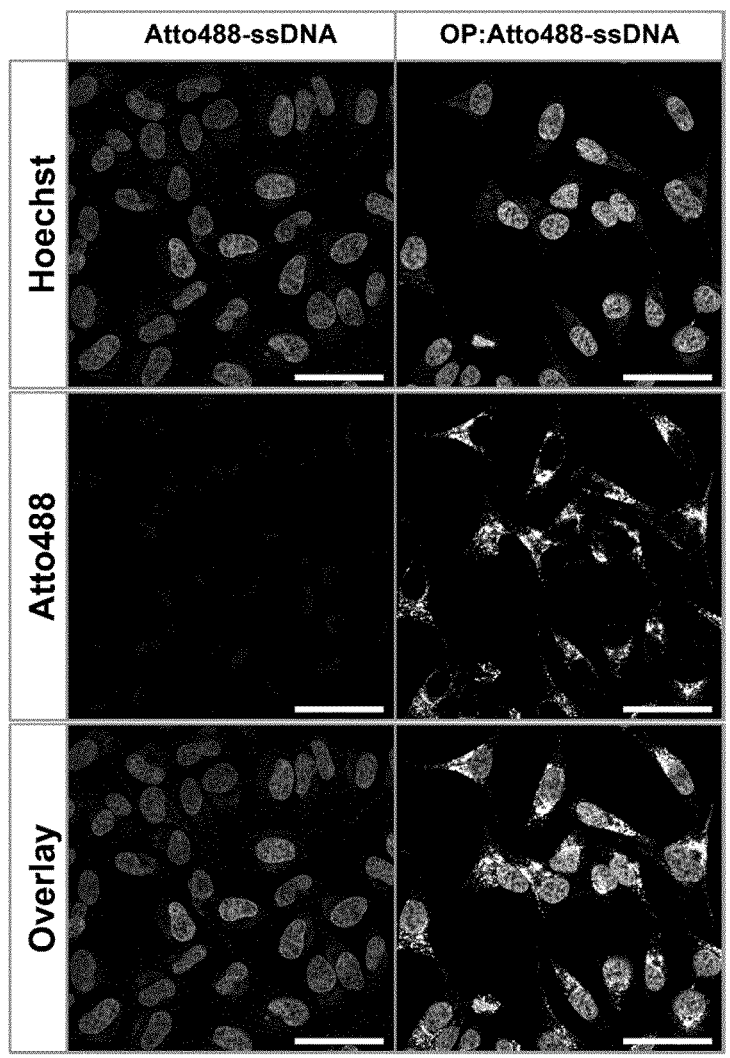
Figure 3C:
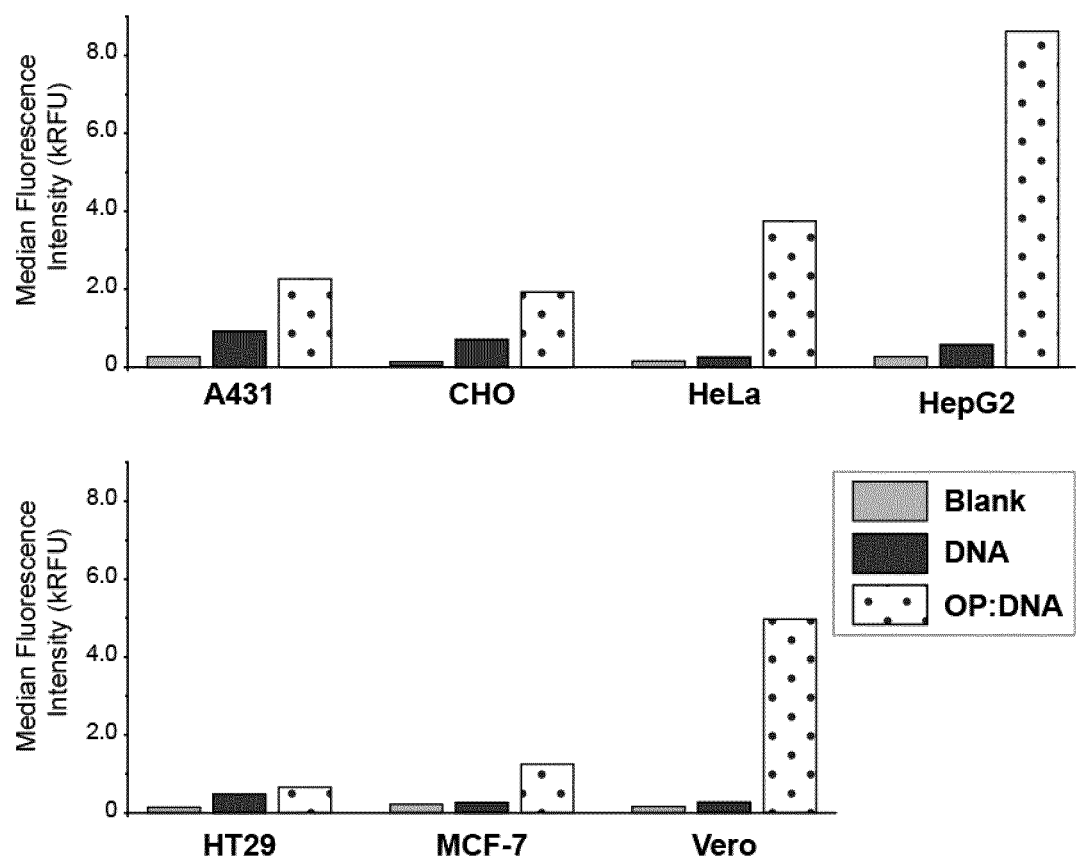

Further, the ability of the nanoparticle of the invention to enter cells and deliver its nucleic acid cargo was investigated using flow cytometry and confocal fluorescence microscopy (CFM), with Atto488-ssDNA cargo as the probe. Seven different cell lines including HeLa cells were treated with 200 nM of either free Atto488-ssDNA or Atto488-ssDNA packaged within OP cages, and the cellular fluorescence was measured by flow cytometry. A plot of median fluorescence intensity shows efficient cellular uptake of OP cages in six out of the seven cell lines tested (FIG. 3a-c). In HeLa cells, almost 30-fold increase in cellular uptake of ssDNA these cells over background, with delivery to more than 90% of the HeLa cells was shown. An even larger effect was seen with Vero and HepG2 cells. To confirm this finding, CFM was carried out on cells treated with either free Atto488-ssDNA or Atto488-ssDNA-loaded OP cages (FIG. 16). Cells treated with free Atto488-DNA exhibited no appreciable fluorescence, while cells treated with OP:Atto488-DNA had intracellular fluorescence localized in many intense foci, corroborating the high uptake efficiency (FIG. 3b). These punctate structures are suggestive of endocytosis, which is often observed for nanoparticles in this size regime.

Example 7—Modulation of Gene Expression

Reports of non-viral delivery systems that can deliver functional nucleic acid cargo without the need for an additional transfection agent are rare. With the high cellular uptake of OP cages confirmed, the ability of the cages to deliver siRNA and modulate gene expression was tested using HeLa cells that stably express green fluorescent protein (GFP) as a model to measure protein expression. Using Lipofectamine 2000 as a positive control, GFP-expressing HeLa cells were treated with naked siRNA, OP-encapsulated siRNA, empty OP cage and OP cages loaded with a scrambled sequence siRNA. To determine gene knock-down efficiency, GFP fluorescence was measured qualitatively, by fluorescence microscopy (FIG. 16), and quantitatively, by flow cytometry (FIG. 4a). After treatment with 20 pmol of OP packaged siRNA and 48 hour incubation 70% reduction was observed in GFP fluorescence, an efficacy within the range of Lipofectamine 2000. Moreover, due to the significantly lower toxicity of OP, cell viability was improved with respect to the commercial reagent (FIG. 16), which was at a concentration of 2.5 µg/mL in these assays. The lack of effect of OP cages loaded with a scrambled sequence siRNA confirmed that expression levels were not due to induction of the antiviral interferon pathway machinery but were target mRNA specific.

Example 8—His6 Tags and High Cytosolic Concentrations of RNA Contribute to ON Delivery Efficiency Successful induction of RNAi requires delivery of siRNA to the cytoplasm. Thus, above-mentioned data suggest that OP cages can achieve endosomal escape and release their cargo. Without being bound by any theory, the inventors suggest two explanations:

First, the ability of histidine-rich peptides to facilitate endosomal escape has been well-documented, both due to the proton sponge effect and the ability of protonated histidine to permeabilize endosomal membranes. As each OP monomer has a His6 tag, the complete 24-mer cage presents a total of 144 histidyl residues on its exterior. To test whether this affected siRNA delivery, the inventors produced a variant of OP that has no His6 tag and assayed it for RNAi activity (Materials & Methods, Purification of OP without His6 tags). Under the same experimental conditions, only a ~40% reduction was observed in GFP fluorescence (FIG. 4a), indicating that the His6 tags indeed contribute to delivery efficiency.

Figure 19:
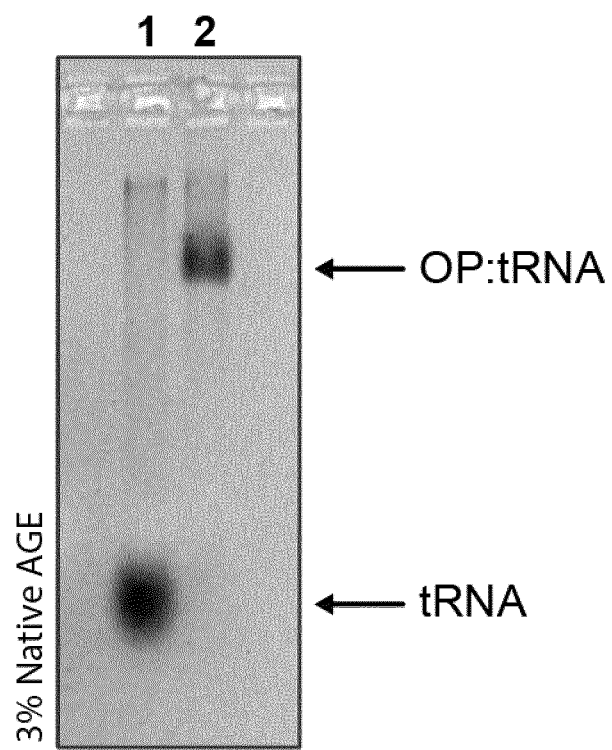
FIG. 19: Encapsulation of tRNA. Native agarose gel analysis showing complete binding of tRNA in the presence of 1.2 equiv. of OP cage. Lane 1—tRNA, Lane 2—tRNA+OP. Stained with GelRed.
Figure 20:
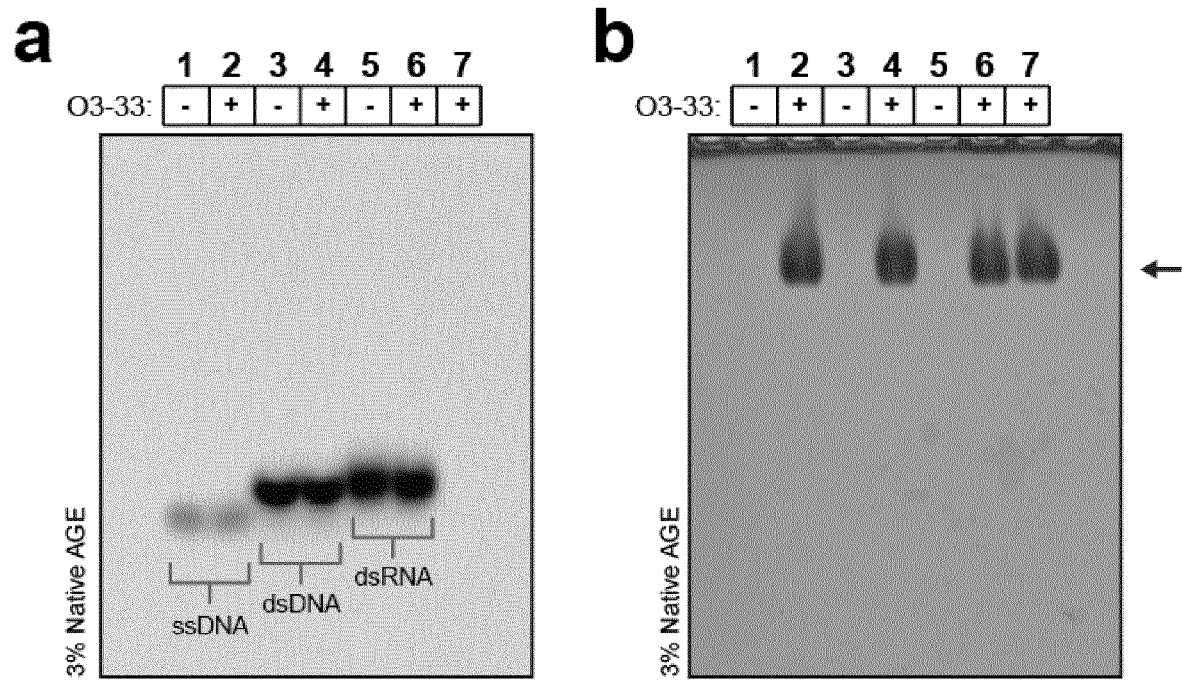
FIG. 20: EMSA of O3-33 with oligonucleotides. The same native agarose gel stained with (a) GelRed for nucleic acid and (b) Coomassie Blue for protein. Arrow: complex (nanoparticle plus ssDNA). Unlabeled ssDNA, dsDNA and dsRNA were analyzed after incubation with two equivalents of O3-33. There is no interaction between the protein cage and any of the oligonucleotides.

Secondly, the release of cargo molecules in the cytoplasm can be explained in terms of the kinetic parameters shown in FIG. 2d. While OP-nucleic acid complexes are stable, encapsulation is reversible in the presence of high concentrations of competing guest molecules. Thus, the inventors expected that high cytosolic concentrations of tRNA could provide a location-specific release mechanism for the siRNA cargo, liberating it for RNAi induced gene knockdown. This hypothesis was validated in vitro: OP cages containing A488-dsDNA were treated with intracellular concentrations of tRNA (26 µM) in PBS at 37° C. and observed time-dependent release of the cargo over 6 hours (FIGS. 4b and 19). For oligonucleotides that act upon mRNA in the cytoplasm, taking advantage of cytosolic physicochemical properties offers a simple solution for cargo release.

Conversely, the same experiment carried out with 10% fetal bovine serum showed no release or degradation of cargo (FIG. 22).

Example 9—Protein Crystallography of Nanoparticles

TABLE 5

Data collection and refinement statistics

| | OP |
| --- | --- |
| Data collection | |

TABLE 5-continued

Data collection and refinement statistics

| | OP |
|---|---|
| Space group | H32 |
| Cell dimensions | |
| a, b, c (Å) | 136.9, 136.9, 559.1 |
| Resolution (Å) | 50.0-3.62 |
| | (3.84-3.62)* |
| $R_{merge}$ | 30.8 (189.2) |
| I/σI | 5.3 (0.9) |
| CC (½) (%) | 98.9 (34.1) |
| Completeness (%) | 98.9 (97.4) |
| Redundancy | 6.0 (6.0) |
| Refinement | |
| Resolution (Å) | 47.6-3.62 |
| No. reflections | 44319 |
| $R_{work}/R_{free}$ | 22.5/28.8 |
| No. atoms | |
| Protein | 10624 |
| B-factors | |
| Protein | 143.7 |
| R.m.s. deviations | |
| Bond lengths (Å) | 0.003 |
| Bond angles (°) | 0.598 |

*One crystal was used for data collection.
*Values in parentheses are for highest-resolution shell.

Example 10—OP and its Variants OTR101 to OTR503

In Vitro Studies of Single-Stranded DNA Loading

Figure 26:
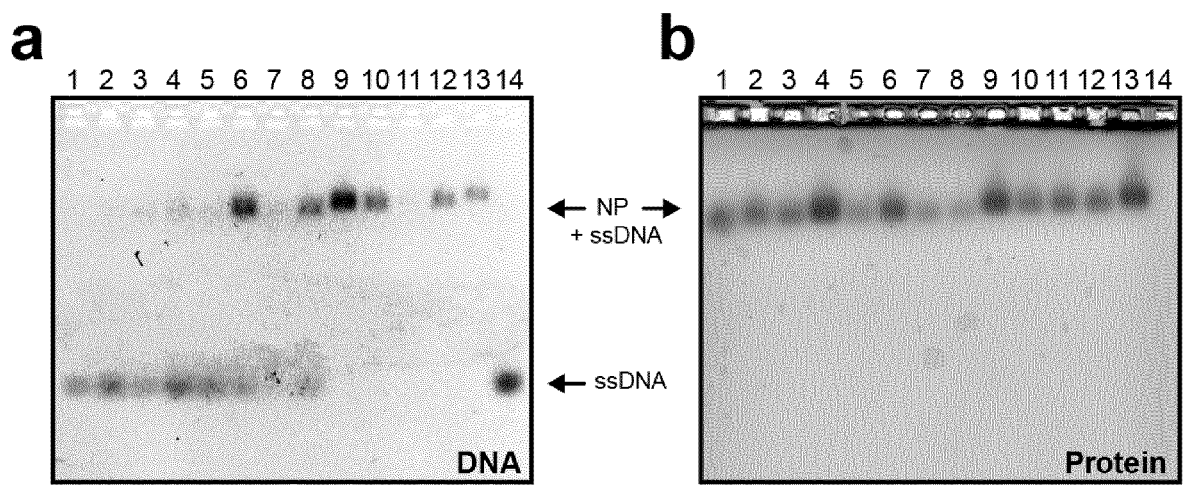
FIG. 26: ssDNA loading into nanoparticles (NP) investigated by an electrophoretic shift assay (EMSA). (a) 2% native gel visualized with Atto488-absorbance by UV transillumination. Lane 1: O3-33. Lane 2: OTR101. Lane 3: OTR201. Lane 4: OTR202. Lane 5: OTR203. Lane 6: OTR301. Lane 7: OTR302. Lane 8: OTR401. Lane 9: OTR402. Lane 10: OTR501. Lane 11: OTR502. Lane 12.

In order to test whether the different variants of OP, OTR101 to OTR503 can load ssDNA, their interaction with ssDNA was investigated in an electrophoretic shift assay (EMSA). Thereby, it is expected that co-localization of the DNA and the protein bands would be observed for binding variants, whilst the ssDNA band mobility would not be affected by non-binding variants. As seen in FIG. 26, this co-localization is observed for all investigated variants that contain a minimum of three arginine mutations per monomer, whilst all investigated variants containing one or two arginines per monomer, as well as O3-33, did not lead to any shift of the Atto488-ssDNA band.

Binding Kinetics of Variants Compared to OP

It was investigated whether the results obtained from the EMSA could be verified in the framework of the fluorescence assay. As displayed in FIG. 27, it can indeed be concluded that the variants with two or fewer arginines do not bind ssDNA. Furthermore, it can be seen that the relative drop in fluorescence, which corresponds to the quenching effect of the capsid, increases with increasing electrostatic contribution.

The kinetic parameters for the binding of ssDNA by all variants with three or more arginine mutations per monomer are shown in Table 7 below.

TABLE 7

Summary of the kinetic parameters for the binding of ssDNA

| Variant | $k_{on}$ [M$^{-1}$ s$^{-1}$] | $k_{off}$ [s$^{-1}$] | $K_d$ [M] |
|---|---|---|---|
| OTR301 | (5.62 ± 0.51) × 10$^4$ | (1.19 ± 0.41) × 10$^{-4}$ | (2.12 ± 0.76) × 10$^{-9}$ |
| OTR302 | (2.10 ± 0.38) × 10$^4$ | (1.80 ± 0.73) × 10$^{-4}$ | (8.59 ± 3.81) × 10$^{-9}$ |
| OTR401 | (1.43 ± 0.03) × 10$^4$ | (2.29 ± 0.52) × 10$^{-4}$ | (1.61 ± 0.37) × 10$^{-8}$ |
| OTR402 | (1.01 ± 0.03) × 10$^6$ | (2.50 ± 0.84) × 10$^{-4}$ | (2.48 ± 0.84) × 10$^{-10}$ |
| OTR501 | (9.88 ± 0.36) × 10$^5$ | (1.28 ± 0.15) × 10$^{-4}$ | (1.30 ± 0.57) × 10$^{-10}$ |
| OTR502 | (7.56 ± 0.43) × 10$^5$ | (2.18 ± 0.56) × 10$^{-4}$ | (2.89 ± 0.76) × 10$^{-10}$ |
| OTR503 | (2.63 ± 0.32) × 10$^5$ | (1.60 ± 0.55) × 10$^{-4}$ | (6.09 ± 2.22) × 10$^{-10}$ |
| OP | (6.60 ± 0.10) × 10$^5$ | (1.60 ± 0.10) × 10$^{-4}$ | (2.42 ± 0.15) × 10$^{-10}$ |

In Vitro Studies of Double-Stranded DNA Loading

Having shown that OP protein variants with three, four or five arginines are capable of loading ssDNA, the loading capacity for dsDNA would be of interest, especially because double-stranded siRNA is more relevant for biomedical applications. For all dsDNA measurements, hairpin DNA (hpDNA) was used, which contains a loop region of four nucleobases between the two complementary strands. hpDNA was chosen in order to avoid dissociation of the two complementary strands in dsDNA.

Before developing a fluorimetry-based assay, cargo loading was investigated by EMSA for all variants that bind ssDNA (FIG. 28). It was found that variants OTR402, OTR501, OTR502, OTR503 and OP bind hpDNA, whereas this is not the case for OTR301, OTR302 and OTR401. Thus, only capsid variants with a maximal binding affinity of 10$^{-10}$ M$^{-1}$ for ssDNA can bind dsDNA/hpDNA as well.

The kinetic parameters for the binding of hpDNA by all variants with 5 or more arginine mutations per monomer are shown in Table 8 below.

TABLE 8

Summary of the kinetic parameters. The association rate constant $k_{on}$ and the dissociation rate constant $k_{off}$ were used to determine the dissociation constant $K_d$.

| Variant | $k_{on}$ [M$^{-1}$ s$^{-1}$] | $k_{off}$ [s$^{-1}$] | $K_d$ [M] |
|---|---|---|---|
| OTR501 | (4.51 ± 1.32) × 10$^5$ | (1.76 ± 0.65) × 10$^{-4}$ | (3.90 ± 1.84) × 10$^{-10}$ |
| OTR502 | (4.05 ± 0.96) × 10$^5$ | (2.77 ± 1.99) × 10$^{-4}$ | (6.84 ± 5.17) × 10$^{-10}$ |
| OTR503 | (2.59 ± 0.22) × 10$^5$ | (4.77 ± 0.71) × 10$^{-5}$ | (1.84 ± 0.32) × 10$^{-10}$ |
| OP | (2.78 ± 0.42) × 10$^5$ | (3.37 ± 1.50) × 10$^{-4}$ | (1.21 ± 0.60) × 10$^{-9}$ |

Example 11—Variation of Externally Displayed Histidine-Rich Peptide

The OP cage bearing one hexa-histidine tag per monomer protein at the C-terminus has been shown to efficiently escape endosomal trapping and thereby successfully release its siRNA cargo to the cytoplasm of a cell for gene knockdown. Variants of the OP cage bearing histidine tags comprising of 3, 6 or 9 histidines fused to the C-terminus were produced and assayed for gene knockdown activity with reference to the OP cage containing a 6 histidine tag. As shown in FIG. 29, all three variants show the same capability to deliver an siRNA into mammalian cells and reduce expression level of a target protein, in this case GFP. Additionally, the importance of the position of the hexa-histidine tag was investigated by testing variant OP-cODC for gene silencing activity. OP-cODC contains a C-terminal appendage of 38 amino acids after the hexa-histidine tag. As shown in FIG. 29, this abolishes the gene knockdown capability of the siRNA containing OP cage, presumable by interfering with the endosomal escape mechanism of the hexa-histidine tag.

Example 12—Immunogenicity of the OP Cage in Mice

Two groups of four BALB/c mice received 1 or 10 μg of OP particles in PBS by tail vein injections on days 0, 16 and 38, and blood was collected on days 0, 14, 29, 52 and 73. Assessment of OP-specific IgG1, IgG2a and IgG2b in serum was carried out by enzyme-linked immunosorbent assay (ELISA). Briefly, a two-fold dilution series of mouse serum samples were applied onto OP-coated multi-well immune plate (Sigma M9410), then detected by biotinylated anti-murine antibodies against the different IgG isotypes (Abcam ab97238/ab97243/ab97248). The development was done colorimetric, using streptavidin-HRP (Biolegend 405210), and 3,3',5,5'-tetramethylbenzidine (TMB, Biolegend 77247/77248) as chromogenic substrate. The optical density of the chromogenic substrate is measured at 450 nm and plotted against the dilution of the serum samples (FIG. 30). 1/2000 dilution was chosen for comparison of the immune response at each time point (FIG. 31). After all injections, elevated anti-OP IgG titers were determined alongside with a dose-dependent response (FIG. 31). By day 72, one month after the second boost immunization, the IgG titers showed a slight retraction. This investigation shows that OP particles induce a specific immune response.

The invention claimed is:

1. A polypeptide comprising an amino acid sequence I, wherein said amino acid sequence I is an amino acid sequence selected from the group consisting of SEQ ID NO: 2 to 5 and SEQ ID NO: 10 to 16, 37 and 38.

2. The polypeptide of claim 1, wherein said amino acid sequence I is an amino acid sequence selected from the group consisting of SEQ ID NO: 2 to 5 and SEQ ID NO: 10 to 16.

3. The polypeptide of claim 1, wherein said polypeptide further comprises a histidine tag, wherein said histidine tag consists of at least two consecutively linked histidines (His tag).

4. The polypeptide of claim 3, wherein said His tag consists of 6 consecutively linked histidines (His6 tag).

5. The polypeptide of claim 1, wherein said amino acid sequence I is the amino acid sequence of SEQ ID NO: 2.

6. The polypeptide of claim 1, wherein said amino acid sequence I is the amino acid sequence of SEQ ID NO: 4.

7. The polypeptide of claim 1, wherein said amino acid sequence I is the amino acid sequence of SEQ ID NO: 5.

8. The polypeptide of claim 1, wherein said amino acid sequence I is the amino acid sequence of SEQ ID NO: 10.

9. The polypeptide of claim 1, wherein said amino acid sequence I is the amino acid sequence of SEQ ID NO: 12.

10. The polypeptide of claim 1, wherein said amino acid sequence I is the amino acid sequence of SEQ ID NO: 13.

11. The polypeptide of claim 1, wherein said amino acid sequence I is the amino acid sequence of SEQ ID NO: 14.

12. The polypeptide of claim 1, wherein said amino acid sequence I is the amino acid sequence of SEQ ID NO: 15.

13. The polypeptide of claim 1, wherein said amino acid sequence I is the amino acid sequence of SEQ ID NO: 16.

14. A nucleic acid sequence encoding the polypeptide of claim 1.

15. A nanoparticle comprising at least one polypeptide according to claim 1.

16. A complex comprising the nanoparticle of claim 15 and one or more cargo molecules, wherein said one or more cargo molecules are encapsulated in said nanoparticle.

17. The complex of claim 16, wherein said one or more cargo molecules are one or more oligonucleotides.

18. The complex of claim 17, wherein said one or more oligonucleotides encapsulated in said nanoparticle are not accessible to DNAse hydrolysis.

19. The complex of claim 17, wherein said one or more oligonucleotides are RNA selected from the group consisting of antisense oligonucleotides (ASO), small interference RNA (siRNA), small hairpin RNA (shRNA), micro RNA (miRNA) and anti-miRNA.

20. A method for transfecting a cell comprising the step of contacting said cell with the complex of claim 16.

* * * * *

UNITED STATES PATENT AND TRADEMARK OFFICE
CERTIFICATE OF CORRECTION

Page 1 of 1

PATENT NO. : 12,410,213 B2
APPLICATION NO. : 17/265765
DATED : September 9, 2025
INVENTOR(S) : Thomas George Watt Edwardson and Donald Hilvert It is certified that error appears in the above-identified patent and that said Letters Patent is hereby corrected as shown below:

On the Title Page

Item (73) Assignee, replace "ETH ZËRICH" with -- ETH ZÜRICH --

Signed and Sealed this
Sixteenth Day of December, 2025

John A. Squires
*Director of the United States Patent and Trademark Office*